United States Patent
Arulanantham et al.

(10) Patent No.: US 9,012,609 B2
(45) Date of Patent: Apr. 21, 2015

(54) ANTI-SERUM ALBUMIN BINDING VARIANTS

(75) Inventors: Haren Arulanantham, Cambridge (GB); Thil Dinuk Batuwangala, Cambridge (GB); Elena De Angelis, Cambridge (GB); Carolyn Enever, Cambridge (GB); Haiqun Liu, Cambridge (GB); Oliver Schon, Cambridge (GB)

(73) Assignee: GlaxoSmithKline Intellectual Property Development Limited (GB)

( * ) Notice: Subject to any disclaimer, the term of this patent is extended or adjusted under 35 U.S.C. 154(b) by 0 days.

(21) Appl. No.: 13/816,515

(22) PCT Filed: Aug. 12, 2011

(86) PCT No.: PCT/EP2011/063999
§ 371 (c)(1),
(2), (4) Date: Feb. 12, 2013

(87) PCT Pub. No.: WO2012/020143
PCT Pub. Date: Feb. 16, 2012

(65) Prior Publication Data
US 2013/0202597 A1    Aug. 8, 2013

Related U.S. Application Data

(60) Provisional application No. 61/373,397, filed on Aug. 13, 2010.

(51) Int. Cl.
*C07K 16/18* (2006.01)
*C07K 16/28* (2006.01)
*A61K 39/395* (2006.01)

(52) U.S. Cl.
CPC .............. *C07K 16/18* (2013.01); *C07K 16/2878* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/569* (2013.01); *C07K 2317/90* (2013.01); *C07K 2317/92* (2013.01); *C07K 2317/94* (2013.01); *C07K 2319/00* (2013.01); *C07K 2319/21* (2013.01); *C07K 2319/41* (2013.01)

(58) Field of Classification Search
None
See application file for complete search history.

(56) References Cited

U.S. PATENT DOCUMENTS

2009/0259026 A1 * 10/2009 Tomlinson et al. ........ 530/387.3

FOREIGN PATENT DOCUMENTS

| WO | WO 2008/096158 A2 | 8/2008 |
|----|----|----|
| WO | 2008149149 | * 12/2008 |
| WO | WO 2008/149146 A2 | 12/2008 |
| WO | WO 2010/063818 A2 | 6/2010 |
| WO | WO 2010/094722 A2 | 8/2010 |
| WO | WO 2011/006915 A2 | 1/2011 |
| WO | WO 2011/039096 A1 | 4/2011 |

OTHER PUBLICATIONS

Wu et al., J Mol Biol 294: 151-162, 1999.*
Colman et al., in Research in Immunology (145(1):33-36, 1994.*
Holt, L. J., et al., Trends in Biotechnology, vol. 21, No. 11, Nov. 1, 2003, pp. 484-490.
T. Tanaka, et al., Journal of Biological Chemistry, vol. 286, No. 85, Feb. 4, 2011, pp. 3707-3716.
Wark, K. L., et al., Advanced Drug Delivery Reviews, vol. 58, No. 5-6, Aug. 7, 2006, pp. 657-670.
Koide, et al., Journal of Molecular Biology, vol. 373, No. 4, Oct. 3, 2007, pp. 941-953.
De Genst, Erwin, et al., Journal of Biological Chemistry, vol. 279, No. 51, Dec. 17, 2004, pp. 53593-53601.

* cited by examiner

*Primary Examiner* — Phuong Huynh
(74) *Attorney, Agent, or Firm* — Jason C. Fedon; William T. Han

(57) ABSTRACT

The invention relates to improved variants of the anti-serum albumin immunoglobulin single variable domains, as well as ligands and drug conjugates comprising such variants, compositions, nucleic acids, vectors and hosts.

17 Claims, 37 Drawing Sheets

Figure 1A

| human | kinetics based on DOM7h-14 and DOM7h-11 lineage (ranges supported by data) | | |
|---|---|---|---|
| | overall range KD: 1 to 10000 Kd:1.5e-4 to 0.1 ; Ka:2e6 to 1e4 | | |
| therapeutic ranges | chronic | intermediate | acute |
| | high affinity KD: 0.1-400 Kd:1.5e-4 to 8e-3 ; Ka:1e6 to 5e4 | medium affinity KD: 400-2000 Kd: 8e-3 to 0.08 ; Ka: 2e4 to 5e4 | low affinity KD: 2000-10000 Kd:0.08 to 0.1 ; Ka: 5e4 to 1e4 |
| optional ranges | KD: 1-200 Kd:3e-4 to 2e-3; Ka: 1e6 to 5e4 | KD: 400-1500 Kd:8e-3 to 0.08; Ka: 2e4 to 6e4 | KD: 2000-6000 Kd:0.08 to 0.1 ; Ka: 5e4 to 2e4 |
| Examples | DOM7h-11-15, DOM7h-14, DOM7h-14-10, DOM7h-14-18, DOM7h-14-19, DOM7h-11-18, DOM7h-11-19 DMS7321, DMS7322; DMS7324, DMS7327 | DMS7325, DMS7326; DMS7323 | DOM7h-11 |

Figure 2A

| Cyno | | | overall range | | |
|---|---|---|---|---|---|
| | | | KD: 1 to 10000 | | |
| | | | Kd:1.5e-4 to 0.1 ; Ka:2e6 to 1e4 | | |
| therapeutic ranges | chronic | | intermediate | | acute |
| | high affinity | | medium affinity | | low affinity |
| | KD: 0.1-400 | | KD: 400-2000 | | KD: 2000-10000 |
| | Kd:1.5e-4 to 8e-3 ; Ka:2e6 to 2e4 | | Kd: 8e-3 to 0.08 ; Ka: 2e4 to 5e4 | | Kd:0.08 to 0.1 ; Ka: 5e4 to 1e4 |
| optional ranges | KD: 1-200 | | KD: 400-1500 | | KD: 2000-6000 |
| | Kd:3e-4 to 2e-3; Ka: 1e6 to 1e4 | | Kd:2e-3 to 0.05; Ka: 2e4 to 1e4 | | Kd:0.08 to 0.1 ; Ka: 5e4 to 2e4 |
| Examples | DMS7327; DOM7h-11-15; DOM7h-14; DOM7h-14-10; DOM7h-14-18; DOM7h-14-19, DOM7h-14-28, DOM7h-14-36 DMS7321; DMS7322 | | DOM7h-11; DMS7326; DMS7324; | | DOM7h11-12, DOM7h-11-18 DMS7325 |

Figure 2B

| Rat | | overall range | |
|---|---|---|---|
| | | KD: 1 to 10000 | |
| | | Kd: 2e-3 to 0.15 ; Ka: 2e6 to 1e4 | |
| therapeutic ranges | chronic | intermediate | acute |
| | high affinity | medium affinity | low affinity |
| | KD: 1-300 | KD: 300-2000 | KD: 2000-10000 |
| | Kd:2e-3 to 5e-2 ; Ka:2e6 to 2e5 | Kd:5e-2 to 0.09 ; Ka:2e5 to 4.5e4 | Kd:0.09 to 0.15 ; Ka: 4.5e4 to 1.5e4 |
| optional ranges | KD: 20-200 | KD: 400-1800 | KD: 2000-6000 |
| | Kd:9e-3 to 2e-2 ; Ka: 1e6 to 1e5 | Kd: 4e-2 to 0.09; Ka:1e5 to 5e4 | Kd: 0.1 to 0.14 ; Ka: 5e4 to 3e4 |
| Examples | DOM7h-11-15; DOM7h-11-12; DOM7h-11-18, DOM7h-11-19, DOM7h-14-28, DOM7h-14-36, DOM7h-14 DMS7327; DMS7322 | DOM7h-14-18; DOM7h-14-19; DMS7321; DMS7323, DMS7324, DMS7326;, | DMS7325; DOM7h-11; |

Figure 2C

| Mouse | | | | |
|---|---|---|---|---|
| | | overall range KD: 1 to 10000 | | |
| | | Kd: 2e-3 to 0.15 ; Ka: 2e6 to 1e4 | | |
| therapeutic ranges | chronic | | intermediate | acute |
| | high affinity KD: 1-100 | | medium affinity KD: 100-2000 | low affinity KD: 2000-10000 |
| | Kd: 2e-3 to 1e-2 ; Ka: 2e6 to 1e5 | | Kd: 1e-2 to 0.07 ; Ka: 1e5 to 3e4 | Kd: 0.08 to 0.15; Ka: 4e4 to 1.5e4 |
| optional ranges | KD: 1 to 80 | | KD: 120-2000 | KD: 4000-10000 |
| | Kd:2e-3 to 1e-2 ; Ka: 2e6 to 1.5e5 | | Kd: 9e-3 to 0.07 ; Ka: 1.3e5 to 3e4 | Kd:0.1 to 0.15 ; Ka: 2.5e4 to 1.5e4 |
| Examples | DOM7h-11-15;; DOM7h-14; DOM7h-14-10, DOM7h-14-18, DOM7h-14-19, DOM7h-11-18, DOM7h-11-19, DOM7h-14-28, DOM7h-14-36 DMS7322, DMS7327 | | DMS7321; DMS7323; DMS7324; DOM7h-11-12; DMS7326 | DMS7325; DOM7h-11 |

DOM7h-11-3 Epitope

```
         10        20        30        40        50        60        70        80        90       100
....|....|....|....|....|....|....|....|....|....|....|....|....|....|....|....|....|....|....|....|
DAHKSEVAHRFKDLGEENFKALVLIAFAQYLQQCPFEDHVKLVNEVTEFAKTCVADESAENCDKSLHTLFGDKLCTVATLRETYGEMADCCAKQEPERNE
        110       120       130       140       150       160       170       180       190       200
....|....|....|....|....|....|....|....|....|....|....|....|....|....|....|....|....|....|....|....|
CFLQHKDDNPNLPRLVRPEVDVMCTAFHDNEETFLKKYLYEIARRHPFYAPELLFFAKRYKAAFTECCQAADKAACLLPKLDELRDEGKVSSAKQRLKC
        210       220       230       240       250       260       270       280       290       300
....|....|....|....|....|....|....|....|....|....|....|....|....|....|....|....|....|....|....|....|
ASLQKFGERAFKAWAVARLSQRFPKAEFAEVSKLVTDLTKVHTECCHGDLLECADDRADLAKYICENQDSISSKLKECCEKPLLEKSHCIAEVENDEMPA
        310       320       330       340       350       360       370       380       390       400
....|....|....|....|....|....|....|....|....|....|....|....|....|....|....|....|....|....|....|....|
DLPSLAADFVESKDVCKNYAEAKDVFLGMFLYEYARRHPDYSVVLLLRLAKTYETTLEKCCAAADPHECYAKVFDEFKPLVEEPQNLIKQNCELFEQLGE
        410       420       430       440       450       460       470       480       490       500
....|....|....|....|....|....|....|....|....|....|....|....|....|....|....|....|....|....|....|....|
YKFQNALLVRYTKKVPQVSTPTLVEVSRNLGKVGSKCCKHPEAKRMPCAEDYLSVVLNQLCVLHEKTPVSDRVTKCCTESLVNRRPCFSALEVDETYVPK
        510       520       530       540       550       560       570       580
....|....|....|....|....|....|....|....|....|....|....|....|....|....|....|....|
EFNAETFTFHADICTLSEKERQIKKQTALVELVKHKPKATKEQLKAVMDDFAAFVEKCCKADDKETCFAEEGKKLVAASQAALGL
```

DOM7h-14-10 Epitope

```
         10        20        30        40        50        60        70        80        90       100
....|....|....|....|....|....|....|....|....|....|....|....|....|....|....|....|....|....|....|....|
DAHKSEVAHRFKDLGEENFKALVLIAFAQYLQQCPFEDHVKLVNEVTEFAKTCVADESAENCDKSLHTLFGDKLCTVATLRETYGEMADCCAKQEPERNE
        110       120       130       140       150       160       170       180       190       200
....|....|....|....|....|....|....|....|....|....|....|....|....|....|....|....|....|....|....|....|
CFLQHKDDNPNLPRLVRPEVDVMCTAFHDNEETFLKKYLYEIARRHPFYAPELLFFAKRYKAAFTECCQAADKAACLLPKLDELRDEGKVSSAKQRLKC
        210       220       230       240       250       260       270       280       290       300
....|....|....|....|....|....|....|....|....|....|....|....|....|....|....|....|....|....|....|....|
ASLQKFGERAFKAWAVARLSQRFPKAEFAEVSKLVTDLTKVHTECCHGDLLECADDRADLAKYICENQDSISSKLKECCEKPLLEKSHCIAEVENDEMPA
        310       320       330       340       350       360       370       380       390       400
....|....|....|....|....|....|....|....|....|....|....|....|....|....|....|....|....|....|....|....|
DLPSLAADFVESKDVCKNYAEAKDVFLGMFLYEYARRHPDYSVVLLLRLAKTYETTLEKCCAAADPHECYAKVFDEFKPLVEEPQNLIKQNCELFEQLGE
        410       420       430       440       450       460       470       480       490       500
....|....|....|....|....|....|....|....|....|....|....|....|....|....|....|....|....|....|....|....|
YKFQNALLVRYTKKVPQVSTPTLVEVSRNLGKVGSKCCKHPEAKRMPCAEDYLSVVLNQLCVLHEKTPVSDRVTKCCTESLVNRRPCFSALEVDETYVPK
        510       520       530       540       550       560       570       580
....|....|....|....|....|....|....|....|....|....|....|....|....|....|....|....|
EFNAETFTFHADICTLSEKERQIKKQTALVELVKHKPKATKEQLKAVMDDFAAFVEKCCKADDKETCFAEEGKKLVAASQAALGL
```

DOM7r-92-4 Epitope

```
         10        20        30        40        50        60        70        80        90       100
....|....|....|....|....|....|....|....|....|....|....|....|....|....|....|....|....|....|....|....|
DAHKSEVAHRFKDLGEENFKALVLIAFAQYLQQCPFEDHVKLVNEVTEFAKTCVADESAENCDKSLHTLFGDKLCTVATLRETYGEMADCCAKQEPERNE
        110       120       130       140       150       160       170       180       190       200
....|....|....|....|....|....|....|....|....|....|....|....|....|....|....|....|....|....|....|....|
CFLQHKDDNPNLPRLVRPEVDVMCTAFHDNEETFLKKYLYEIARRHPFYAPELLFFAKRYKAAFTECCQAADKAACLLPKLDELRDEGKVSSAKQRLKC
        210       220       230       240       250       260       270       280       290       300
....|....|....|....|....|....|....|....|....|....|....|....|....|....|....|....|....|....|....|....|
ASLQKFGERAFKAWAVARLSQRFPKAEFAEVSKLVTDLTKVHTECCHGDLLECADDRADLAKYICENQDSISSKLKECCEKPLLEKSHCIAEVENDEMPA
        310       320       330       340       350       360       370       380       390       400
....|....|....|....|....|....|....|....|....|....|....|....|....|....|....|....|....|....|....|....|
DLPSLAADFVESKDVCKNYAEAKDVFLGMFLYEYARRHPDYSVVLLLRLAKTYETTLEKCCAAADPHECYAKVFDEFKPLVEEPQNLIKQNCELFEQLGE
        410       420       430       440       450       460       470       480       490       500
....|....|....|....|....|....|....|....|....|....|....|....|....|....|....|....|....|....|....|....|
YKFQNALLVRYTKKVPQVSTPTLVEVSRNLGKVGSKCCKHPEAKRMPCAEDYLSVVLNQLCVLHEKTPVSDRVTKCCTESLVNRRPCFSALEVDETYVPK
        510       520       530       540       550       560       570       580
....|....|....|....|....|....|....|....|....|....|....|....|....|....|....|....|
EFNAETFTFHADICTLSEKERQIKKQTALVELVKHKPKATKEQLKAVMDDFAAFVEKCCKADDKETCFAEEGKKLVAASQAALGL
```

Figure 6

```
              10        20        30        40        50        60        70        80        90       100
          ....|....|....|....|....|....|....|....|....|....|....|....|....|....|....|....|....|....|....|....|....
DOM7h-11  DIQMTQSPSSLSASVGDRVTITCRASRPIGTTLSWYQQKPGKAPKLLIWFGSRLQSGVPSRFSGSGSGTDFTLTISSLQPEDFATYYCAQAGTHPTTFGQGTKVEIKR
DOM7h-11-15 ................................M................LAF................................................
DOM7h-11-3  ...................................................LWN................................................
Paratope                                  GTM              LAF R              S                       A  H
                                          ‾‾‾‾‾            ‾‾‾‾‾‾‾                                    ‾‾‾‾‾‾‾
                                          CDR1              CDR2                                      CDR3
```

Figure 10

DOMAIN 2 OF HSA AMINO ACID SEQ ID 79

EGKVSSAKQRLKCASLQKFGERAFKAWAVARLSQRFPKAEFAEVSKLVTDLTKVHT
ECCHGDLLECADDRADLAKYICENQDSISSKLKECCEKPLLEKSHCIAEVENDEMPA
DLPSLAADFVESKDVCKNYAEAKDVFLGMFLYEYARRHPDYSVVLLLRLAKTYETT
LEKCCAAADPHECYAKVFDEFKPLVEEP

DOMAIN 2 OF HSA NUCLEIC ACID SEQ ID 80

GAAGGGAAGGTTTCGTCTGCCAAACAGAGACTCAAGTGTGCCAGTCTCCAAAAA
TTTGGAGAAAGAGCTTTCAAAGCATGGGCAGTAGCTCGCCTGAGCCAGAGATTT
CCCAAAGCTGAGTTTGCAGAAGTTTCCAAGTTAGTGACAGATCTTACCAAAGTCC
ACACGGAATGCTGCCATGGAGATCTGCTTGAATGTGCTGATGACAGGGCGGACC
TTGCCAAGTATATCTGTGAAAATCAAGATTCGATCTCCAGTAAACTGAAGGAATG
CTGTGAAAAACCTCTGTTGGAAAAATCCCACTGCATTGCCGAAGTGGAAAATGA
TGAGATGCCTGCTGACTTGCCTTCATTAGCTGCTGATTTTGTTGAAAGTAAGGAT
GTTTGCAAAAACTATGCTGAGGCAAAGGATGTCTTCCTGGGCATGTTTTTGTATG
AATATGCAAGAAGGCATCCTGATTACTCTGTCGTGCTGCTGCTGAGACTTGCCAA
GACATATGAAACCACTCTAGAGAAGTGCTGTGCCGCTGCAGATCCTCATGAATG
CTATGCCAAAGTGTTCGATGAATTTAAACCTCTTGTGGAAGAGCCT

FULL LENGTH HSA AMINO ACID SEQ ID 81

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGL

FULL LENGTH HSA NUCLEIC ACID SEQ ID 82

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT

Figure 10 Cont.

CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCAAAGCTGAGTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCAAAAACTATGCTGAGGCAAAGGATGTCTTCCTGGGC
ATGTTTTTGTATGAATATGCAAGAAGGCATCCTGATTACTCTGTCGTGCTGCTGCT
GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC
CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTA

DOM 7H-14-10 AMINO ACID SEQ ID 83

DIQMTQSPSSLSASVGDRVTITCRASQWIGSQLSWYQQKPGKAPKLLIMWRSSLQSG
VPSRFSGSGSGTDFTLTISSLQPEDFATYYCAQGLRHPKTFGQGTKVEIKR

DOM 7H-14-10 NUCLEIC ACID SEQ ID 84

TCGACGGACATCCAGATGACCCAGTCTCCATCCTCCCTGTCTGCATCTGTAGGAG
ACCGTGTCACCATCACTTGCCGGGCAAGTCAGTGGATTGGGTCTCAGTTATCTTG
GTACCAGCAGAAACCAGGGAAAGCCCCTAAGCTCCTGATCATGTGGCGTTCCTC
GTTGCAAAGTGGGGTCCCATCACGTTTCAGTGGCAGTGGATCTGGGACAGATTTC
ACTCTCACCATCAGCAGTCTGCAACCTGAAGATTTTGCTACGTACTACTGTGCTC
AGGGTTTGAGGCATCCTAAGACGTTCGGCCAAGGGACCAAGGTGGAAATCAAAC
GG

Figure 10 Cont.

PRIMER TB147 SEQ ID 85

TAACAAGAATAATGGGATCCACCGGCGATGCACACAAGAGTGAGGTTGCTCATCGG

PRIMER TB148 SEQ ID 86

GCGCGCGCGCGCTTCAAGCTTTCATTAATGGTGATGGTGATGATGTAAGCCTAAGGCAGCTTGACTTGCAGCAACAAGTTTTTTACCC

PRIMER TB153 SEQ ID 87

GAGCCAGAGATTTCCCGCCGCTGAGTTTGCAGAAG

PRIMER TB154 SEQ ID 88

CTTCTGCAAACTCAGCGGCGGGAAATCTCTGGCTC

PRIMER TB155 SEQ ID 89

GAGATTTCCCAAAGCTGCCTTTGCAGAAGTTTCCAAG

PRIMER TB156 SEQ ID 90

CTTGGAAACTTCTGCAAAGGCAGCTTTGGGAAATCTC

PRIMER TB157 SEQ ID 91

CCAAAGCTGAGTTTGCAGCCGTTTCCAAGTTAGTGAC

PRIMER TB158 SEQ ID 92

GTCACTAACTTGGAAACGGCTGCAAACTCAGCTTTGG

PRIMER TB159 SEQ ID 93

GATTTTGTTGAAAGTAAGGCCGTTTGCAAAAACTATG

PRIMER TB160 SEQ ID 94

CATAGTTTTTGCAAACGGCCTTACTTTCAACAAAATC

PRIMER TB161 SEQ ID 95

GAAAGTAAGGATGTTTGCGCCAACTATGCTGAGGCAAAGG

PRIMER TB162 SEQ ID 96

CCTTTGCCTCAGCATAGTTGGCGCAAACATCCTTACTTTC

Figure 10 Cont.

PRIMER TB163 SEQ ID 97

GCTGAGGCAAAGGATGCCTTCCTGGGCATGTTTTTG

PRIMER TB164 SEQ ID 98

CAAAAACATGCCCAGGAAGGCATCCTTTGCCTCAGC

PRIMER TB165 SEQ ID 99

GGATGTCTTCCTGGGCGCCTTTTTGTATGAATATG

PRIMER TB166 SEQ ID 100

CATATTCATACAAAAAGGCGCCCAGGAAGACATCC

PRIMER TB167 SEQ ID 101

GCTGCTGCTGAGACTTGCCGCCACATATGAAACCACTCTAG

PRIMER TB168 SEQ ID 102

CTAGAGTGGTTTCATATGTGGCGGCAAGTCTCAGCAGCAGC

HSA-His6 WT SEQ ID 103

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGLHHHHHH

HSA-His6 K225A SEQ ID 104

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
AAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE

Figure 10 Cont.

DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGLHHHHHH

HSA-His6 E227A SEQ ID 105

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAAFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGLHHHHHH

HSA-His6 E230A SEQ ID 106

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAEFAAVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGLHHHHHH

HSA-His6 D314A SEQ ID 107

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAEFAEVSKLVTDLTKVHTECCHGDLLECADDRADLAKYICENQDSISSKLKECCEK
PLLEKSHCIAEVENDEMPADLPSLAADFVESKAVCKNYAEAKDVFLGMFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF

Figure 10 Cont.

TFHADICTLSEKERQIKKQTALVELVKHKPKATKEQLKAVMDDFAAFVEKCCKADD
KETCFAEEGKKLVAASQAALGLHHHHHH

HSA-His6 K317A  SEQ ID 108

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAEFAEVSKLVTDLTKVHTECCHGDLLECADDRADLAKYICENQDSISSKLKECCEK
PLLEKSHCIAEVENDEMPADLPSLAADFVESKDVCANYAEAKDVFLGMFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGLHHHHHH

HSA-His6 V325A  SEQ ID 109

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAEFAEVSKLVTDLTKVHTECCHGDLLECADDRADLAKYICENQDSISSKLKECCEK
PLLEKSHCIAEVENDEMPADLPSLAADFVESKDVCKNYAEAKDAFLGMFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGLHHHHHH

HSA-His6 M329A  SEQ ID 110

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGAFLYEYARR
HPDYSVVLLLRLAKTYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGLHHHHHH

Figure 10 Cont.

HSA-His6 K351A SEQ ID 111

DAHKSEVAHRFKDLGEENFKALVLIAFAQYLQQCPFEDHVKLVNEVTEFAKTCVAD
ESAENCDKSLHTLFGDKLCTVATLRETYGEMADCCAKQEPERNECFLQHKDDNPNL
PRLVRPEVDVMCTAFHDNEETFLKKYLYEIARRHPYFYAPELLFFAKRYKAAFTECC
QAADKAACLLPKLDELRDEGKVSSAKQRLKCASLQKFGERAFKAWAVARLSQRFP
KAEFAEVSKLVTDLTKVHTECCHGDLLECADDRADLAKYICENQDSISSKLKECCEK
PLLEKSHCIAEVENDEMPADLPSLAADFVESKDVCKNYAEAKDVFLGMFLYEYARR
HPDYSVVLLLRLAATYETTLEKCCAAADPHECYAKVFDEFKPLVEEPQNLIKQNCEL
FEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADD
KETCFAEEGKKLVAASQAALGLHHHHHH

HSA-His6 WT SEQ ID 112

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAACATGTGTTGCT
GATGAGTCAGCTGAAAATTGTGACAAATCACTTCATACCCTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCAAAGCTGAGTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCAAAAACTATGCTGAGGCAAAGGATGTCTTCCTGGGC
ATGTTTTTGTATGAATATGCAAGAAGGCATCCTGATTACTCTGTCGTGCTGCTGCT
GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC
CAAATGCTGCACAGAATCCTTGGTGAACAGGCGACCATGCTTTTCAGCTCTGGAA

Figure 10 Cont.

GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT

HSA-His6 K225A SEQ ID 113

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCGCCGCTGAGTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCAAAAACTATGCTGAGGCAAAGGATGTCTTCCTGGGC
ATGTTTTTGTATGAATATGCAAGAAGGCATCCTGATTACTCTGTCGTGCTGCTGCT
GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC
CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT

Figure 10 Cont.

HSA-His6 E227A SEQ ID 114

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCAAAGCTGCCTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCAAAAACTATGCTGAGGCAAAGGATGTCTTCCTGGGC
ATGTTTTTGTATGAATATGCAAGAAGGCATCCTGATTACTCTGTCGTGCTGCTGCT
GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC
CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT

HSA-His6 E230A SEQ ID 115

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTTGGAGACAAAT
TATGCACAGTTGCAACTCTTCGTGAAACCTATGGTGAAATGGCTGACTGCTGTGC

Figure 10 Cont.

```
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCAAAGCTGAGTTTGCAGCCGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCAAAAACTATGCTGAGGCAAAGGATGTCTTCCTGGGC
ATGTTTTTGTATGAATATGCAAGAAGGCATCCTGATTACTCTGTCGTGCTGCTGCT
GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC
CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT
```

HSA-His6 D314A SEQ ID 116

```
GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
```

Figure 10 Cont.

AGCCAGAGATTTCCCAAAGCTGAGTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGCCGTTTGCAAAAACTATGCTGAGGCAAAGGATGTCTTCCTGGGC
ATGTTTTTGTATGAATATGCAAGAAGGCATCCTGATTACTCTGTCGTGCTGCTGCT
GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAACGCCAGTAAGTGACAGAGTCAC
CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT

HSA-His6 K317A SEQ ID 117

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCAAAGCTGAGTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCGCCAACTATGCTGAGGCAAAGGATGTCTTCCTGGGC
ATGTTTTTGTATGAATATGCAAGAAGGCATCCTGATTACTCTGTCGTGCTGCTGCT

Figure 10 Cont.

GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC
CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT

HSA-His6 V325A SEQ ID 118

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCAAAGCTGAGTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCAAAAACTATGCTGAGGCAAAGGATGCCTTCCTGGGC
ATGTTTTTGTATGAATATGCAAGAAGGCATCCTGATTACTCTGTCGTGCTGCTGCT
GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC

Figure 10 Cont.

CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT

HSA-His6 M329A  SEQ ID 119

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCAAAGCTGAGTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCAAAAACTATGCTGAGGCAAAGGATGTCTTCCTGGGC
GCCTTTTTGTATGAATATGCAAGAAGGCATCCTGATTACTCTGTCGTGCTGCTGCT
GAGACTTGCCAAGACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC
CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT

Figure 10 Cont.

HSA-His6 K351A SEQ ID 120

GATGCACACAAGAGTGAGGTTGCTCATCGGTTTAAAGATTTGGGAGAAGAAAAT
TTCAAAGCCTTGGTGTTGATTGCCTTTGCTCAGTATCTTCAGCAGTGTCCATTTGA
AGATCATGTAAAATTAGTGAATGAAGTAACTGAATTTGCAAAAACATGTGTTGCT
GATGAGTCAGCTGAAAATTGTGACAAATCACTTCATACCCTTTTTGGAGACAAAT
TATGCACAGTTGCAACTCTTCGTGAAACCTATGGTGAAATGGCTGACTGCTGTGC
AAAACAAGAACCTGAGAGAAATGAATGCTTCTTGCAACACAAAGATGACAACCC
AAACCTCCCCCGATTGGTGAGACCAGAGGTTGATGTGATGTGCACTGCTTTTCAT
GACAATGAAGAGACATTTTTGAAAAAATACTTATATGAAATTGCCAGAAGACAT
CCTTACTTTTATGCCCCGGAACTCCTTTTCTTTGCTAAAAGGTATAAAGCTGCTTT
TACAGAATGTTGCCAAGCTGCTGATAAAGCTGCCTGCCTGTTGCCAAAGCTCGAT
GAACTTCGGGATGAAGGGAAGGTTTCGTCTGCCAAACAGAGACTCAAGTGTGCC
AGTCTCCAAAAATTTGGAGAAAGAGCTTTCAAAGCATGGGCAGTAGCTCGCCTG
AGCCAGAGATTTCCCAAAGCTGAGTTTGCAGAAGTTTCCAAGTTAGTGACAGATC
TTACCAAAGTCCACACGGAATGCTGCCATGGAGATCTGCTTGAATGTGCTGATGA
CAGGGCGGACCTTGCCAAGTATATCTGTGAAAATCAAGATTCGATCTCCAGTAA
ACTGAAGGAATGCTGTGAAAAACCTCTGTTGGAAAAATCCCACTGCATTGCCGA
AGTGGAAAATGATGAGATGCCTGCTGACTTGCCTTCATTAGCTGCTGATTTTGTT
GAAAGTAAGGATGTTTGCAAAAACTATGCTGAGGCAAAGGATGTCTTCCTGGGC
ATGTTTTTGTATGAATATGCAAGAAGGCATCCTGATTACTCTGTCGTGCTGCTGCT
GAGACTTGCCGCCACATATGAAACCACTCTAGAGAAGTGCTGTGCCGCTGCAGA
TCCTCATGAATGCTATGCCAAAGTGTTCGATGAATTTAAACCTCTTGTGGAAGAG
CCTCAGAATTTAATCAAACAAAATTGTGAGCTTTTTGAGCAGCTTGGAGAGTACA
AATTCCAGAATGCGCTATTAGTTCGTTACACCAAGAAAGTACCCCAAGTGTCAAC
TCCAACTCTTGTAGAGGTCTCAAGAAACCTAGGAAAAGTGGGCAGCAAATGTTG
TAAACATCCTGAAGCAAAAAGAATGCCCTGTGCAGAAGACTATCTATCCGTGGT
CCTGAACCAGTTATGTGTGTTGCATGAGAAAACGCCAGTAAGTGACAGAGTCAC
CAAATGCTGCACAGAATCCTTGGTGAACAGGCGACCATGCTTTTCAGCTCTGGAA
GTCGATGAAACATACGTTCCCAAAGAGTTTAATGCTGAAACATTCACCTTCCATG
CAGATATATGCACACTTTCTGAGAAGGAGAGACAAATCAAGAAACAAACTGCAC
TTGTTGAGCTTGTGAAACACAAGCCCAAGGCAACAAAAGAGCAACTGAAAGCTG
TTATGGATGATTTCGCAGCTTTTGTAGAGAAGTGCTGCAAGGCTGACGATAAGGA
GACCTGCTTTGCCGAGGAGGGTAAAAAACTTGTTGCTGCAAGTCAAGCTGCCTTA
GGCTTACATCATCACCATCACCATT

DOM 7H-11-13 SEQ ID 121

STDIQMTQSPSSLSASVGDRVTITCRASRPIGTTLSWYQQKPGKAPKLLILWNSRLQS
GVPSRFSGSGSGTDFTLTISSLQPEDFATYYCAQAGTHPTTFGQGTKVEIKRAAA

Figure 10 Cont.

DOM 7H-11-13 SEQ ID 122

TCGACGGACATCCAGATGACCCAGTCTCCATCCTCCCTGTCTGCATCTGTAGGAG
ACCGTGTCACCATCACTTGCCGGGCAAGTCGTCCGATTGGGACGACGTTAAGTTG
GTACCAGCAGAAACCAGGGAAAGCCCCTAAGCTCCTGATCCTTTGGAATTCCCGT
TTGCAAAGTGGGGTCCCATCACGTTTCAGTGGCAGTGGATCTGGGACAGATTTCA
CTCTCACCATCAGCAGTCTGCAACCTGAAGATTTTGCTACGTACTACTGTGCGCA
GGCTGGGACGCATCCTACGACGTTCGGCCAAGGGACCAAGGTGGAAATCAAACG
GGCGGCCGCA

DOM7h-14 SEQ ID NO: 123

DIQMTQSPSSLSASVGDRVTITCRASQWIGSQLSWYQQKPGKAPKLLIMWRSSLQSG
VPSRFSGSGSGTDFTLTISSLQPEDFATYYCAQGAALPRTFGQGTKVEIKR

DOM7h-14 SEQ ID NO: 124

GACATCCAGATGACCCAGTCTCCATCCTCCCTGTCTGCATCTGTAGGAGACCGTG
TCACCATCACTTGCCGGGCAAGTCAGTGGATTGGGTCTCAGTTATCTTGGTACCA
GCAGAAACCAGGGAAAGCCCCTAAGCTCCTGATCATGTGGCGTTCCTCGTTGCA
AAGTGGGGTCCCATCACGTTTCAGTGGCAGTGGATCTGGGACAGATTTCACTCTC
ACCATCAGCAGTCTGCAACCTGAAGATTTTGCTACGTACTACTGTGCTCAGGGTG
CGGCGTTGCCTAGGACGTTCGGCCAA GGGACCAAGGTGGAAATCAAACGG

DOM7h-11 SEQ ID 125

DIQMTQSPSSLSASVGDRVTITCRASRPIGTTLSWYQQKPGKAPKLLIWFGSRLQSGV
PSRFSGSGSGTDFTLTISSLQPEDFATYYCAQAGTHPTTFGQGTKVEIKR

DOM7h-11 SEQ ID 126

GACATCCAGATGACCCAGTCTCCATCCTCCCTGTCTGCATCTGTAGGAGACCGTG
TCACCATCACTTGCCGGGCAAGTCGTCCGATTGGGACGACGTTAAGTTGGTACCA
GCAGAAACCAGGGAAAGCCCCTAAGCTCCTGATCTGGTTTGGTTCCCGGTTGCAA
AGTGGGGTCCCATCACGTTTCAGTGGCAGTGGATCTGGGACAGATTTCACTCTCA
CCATCAGCAGTCTGCAACCTGAAGATTTTGCTACGTACTACTGTGCGCAGGCTGG
GACGCATCCTACGACGTTCGGCCAA GGGACCAAGGTGGAAATCAAACGG

Figure 11

Table 17

| (A) | Incubation Time (Seconds) | | | | | | |
|---|---|---|---|---|---|---|---|
| Peptide | 30 | 100 | 300 | 1000 | 3000 | 10000 | Average |
| 189-198 | 9% | -7% | 7% | -1% | -2% | 6% | 2% |
| 189-200 | 2% | 5% | 3% | 3% | -2% | 2% | 2% |
| 203-210 | -2% | 2% | 0% | 0% | 5% | 0% | 1% |
| 203-213 | 8% | 5% | 1% | 1% | -1% | 6% | 3% |
| 213-219 | -9% | -25% | -32% | -35% | -39% | -32% | -29% |
| 216-219 | -12% | -20% | -28% | -36% | -43% | -42% | -30% |
| 220-228 | -35% | -31% | -31% | -18% | -19% | -8% | -24% |
| 222-228 | -38% | -36% | -40% | -26% | -15% | -3% | -26% |
| 231-238 | -17% | -41% | -51% | -54% | -58% | -33% | -42% |
| 231-250 | Not detected | Not detected | Not detected | Not detected | Not detected | Not detected | Not detected |
| 237-250 | -4% | -8% | -5% | -3% | -1% | -1% | -4% |
| 237-251 | 0% | -5% | -8% | -4% | -1% | 3% | -3% |
| 237-252 | -1% | -5% | -4% | -4% | -1% | -2% | -3% |
| 253-260 | 10% | -6% | 5% | -3% | -1% | -1% | 1% |
| 266-284 | Not detected | Not detected | Not detected | Not detected | Not detected | Not detected | Not detected |
| 269-289 | Not detected | Not detected | Not detected | Not detected | Not detected | Not detected | Not detected |
| 269-292 | Not detected | Not detected | Not detected | Not detected | Not detected | Not detected | Not detected |
| 292-302 | -2% | -5% | -2% | -3% | 2% | -9% | -3% |
| 292-305 | 5% | 5% | 1% | 3% | -1% | -5% | 1% |
| 295-305 | -2% | -2% | 0% | 4% | -2% | 2% | 0% |
| 301-305 | 2% | -1% | -11% | -1% | -1% | 6% | -1% |
| 311-318 | -24% | -18% | -10% | -1% | 0% | 0% | -9% |
| 311-326 | -24% | -24% | -27% | -19% | -13% | -7% | -19% |
| 312-326 | -28% | -24% | -29% | -18% | -15% | -9% | -21% |
| 321-326 | -20% | -20% | -29% | -25% | -23% | -17% | -22% |
| 329-330 | -1% | -7% | -18% | -29% | -46% | -56% | -26% |
| 329-331 | -4% | -8% | -9% | -26% | -39% | -48% | -22% |
| 332-333 | 2% | 5% | -4% | -2% | -14% | -27% | -7% |
| 334-342 | -8% | -20% | -15% | -22% | -31% | -31% | -21% |
| 336-345 | 0% | -2% | -8% | -12% | -9% | -11% | -7% |
| 344-346 | -2% | 4% | -1% | -9% | -5% | -8% | -4% |
| 345-346 | 2% | 0% | 1% | -7% | -6% | -15% | -4% |
| 347-349 | Not detected | Not detected | Not detected | Not detected | Not detected | Not detected | Not detected |
| 348-349 | -10% | -18% | -30% | -31% | -30% | -20% | -23% |
| 348-357 | -24% | -33% | -41% | -39% | -37% | -28% | -34% |
| 349-357 | -27% | -33% | -43% | -41% | -40% | -30% | -36% |
| 373-384 | 2% | 1% | 0% | 3% | -2% | 6% | 2% |
| 376-384 | 4% | 3% | 1% | -1% | 1% | 3% | 2% |
| 380-384 | -5% | -2% | -4% | 8% | -3% | 5% | 0% |

| Peptide | Incubation Time (Seconds) | | | | | | |
|---|---|---|---|---|---|---|---|
| | 30 | 100 | 300 | 1000 | 3000 | 10000 | Average |
| 189-198 | -6% | 2% | 6% | 9% | -4% | 8% | 3% |
| 189-200 | -4% | 3% | 4% | 6% | -6% | 4% | 1% |
| 203-210 | -4% | 1% | 4% | 6% | -6% | 3% | 1% |
| 203-213 | 1% | 3% | 5% | 5% | -6% | 4% | 2% |
| 213-219 | -14% | -26% | -32% | -50% | -51% | -49% | -37% |
| 216-219 | -17% | -28% | -36% | -55% | -60% | -65% | -44% |
| 220-228 | -63% | -47% | -47% | -51% | -42% | -25% | -46% |
| 222-228 | -62% | -55% | -52% | -55% | -40% | -26% | -48% |
| 231-238 | -23% | -28% | -43% | -56% | -55% | -48% | -42% |
| 231-250 | -4% | -15% | -15% | -23% | -26% | -22% | -18% |
| 237-250 | -9% | -3% | -1% | -3% | -4% | 3% | -3% |
| 237-251 | -3% | -1% | -2% | -1% | -6% | 2% | -2% |
| 237-252 | -5% | -4% | -4% | 5% | -1% | 5% | -1% |
| 253-260 | -5% | 1% | -1% | -7% | -5% | 7% | -2% |
| 266-284 | -13% | -7% | 2% | 5% | -2% | 10% | -1% |
| 269-289 | -9% | -4% | -8% | 0% | -7% | 4% | -4% |
| 269-292 | 0% | 2% | -3% | 6% | -3% | 3% | 1% |
| 292-302 | -9% | -4% | -3% | 12% | -5% | 6% | -1% |
| 292-305 | -5% | 1% | -4% | 5% | -5% | 3% | -1% |
| 295-305 | -7% | -1% | -1% | 13% | -8% | 7% | 1% |
| 301-305 | 5% | -3% | 1% | 10% | -2% | -5% | 1% |
| 311-318 | -27% | -23% | -17% | -5% | -7% | 7% | -12% |
| 311-326 | -30% | -26% | -25% | -19% | -19% | -7% | -21% |
| 312-326 | -27% | -22% | -22% | -18% | -20% | -9% | -20% |
| 321-326 | -9% | -13% | -18% | -13% | -18% | -11% | -14% |
| 329-330 | -5% | -15% | -13% | -35% | -43% | -67% | -30% |
| 329-331 | -3% | -7% | -10% | -23% | -31% | -56% | -22% |
| 332-333 | -2% | 0% | -2% | -14% | -18% | -55% | -15% |
| 334-342 | -7% | -7% | -11% | -18% | -23% | -35% | -17% |
| 336-345 | -5% | -7% | -5% | -9% | -15% | -13% | -9% |
| 344-346 | 4% | 5% | -1% | -7% | -9% | -14% | -4% |
| 345-346 | 3% | -2% | 2% | -2% | -8% | -29% | -6% |
| 347-349 | -11% | -15% | -15% | -41% | -47% | -50% | -30% |
| 348-349 | -7% | -18% | -20% | -40% | -43% | -35% | -27% |
| 348-357 | -28% | -36% | -43% | -60% | -50% | -44% | -44% |
| 349-357 | -31% | -33% | -41% | -62% | -57% | -54% | -46% |
| 373-384 | -5% | -1% | -1% | 5% | -5% | 7% | 0% |
| 376-384 | -1% | 1% | 4% | 9% | -4% | 4% | 2% |
| 380-384 | -3% | -2% | -2% | 8% | -7% | 0% | -1% |

| Peptide | 30 | 100 | 300 | 1000 | 3000 | 10000 | Average |
|---|---|---|---|---|---|---|---|
| 189-198 | Not detected | Not detected | Not detected | Not detected | Not detected | Not detected | Not detected |
| 189-200 | 1% | -6% | -4% | 1% | -2% | -1% | -2% |
| 203-210 | -20% | -21% | -12% | -16% | -16% | -14% | -17% |
| 203-213 | Not detected | Not detected | Not detected | Not detected | Not detected | Not detected | Not detected |
| 213-219 | -5% | -9% | -15% | -21% | -28% | -32% | -18% |
| 216-219 | -8% | -11% | -16% | -24% | -24% | -30% | -19% |
| 220-228 | Not detected | Not detected | Not detected | Not detected | Not detected | Not detected | Not detected |
| 222-228 | -29% | -28% | -22% | -16% | -3% | -5% | -17% |
| 231-238 | -1% | 2% | -6% | -8% | -11% | -13% | -6% |
| 231-250 | Not detected | Not detected | Not detected | Not detected | Not detected | Not detected | Not detected |
| 237-250 | 2% | 4% | 3% | 0% | -1% | 1% | 2% |
| 237-251 | Not detected | Not detected | Not detected | Not detected | Not detected | Not detected | Not detected |
| 237-252 | 0% | -4% | -2% | -4% | 1% | -2% | -2% |
| 253-260 | 1% | -11% | 2% | -6% | -3% | 4% | -2% |
| 266-284 | Not detected | Not detected | Not detected | Not detected | Not detected | Not detected | Not detected |
| 269-289 | Not detected | Not detected | Not detected | Not detected | Not detected | Not detected | Not detected |
| 269-292 | Not detected | Not detected | Not detected | Not detected | Not detected | Not detected | Not detected |
| 292-302 | 1% | -5% | -10% | -6% | 6% | 5% | -2% |
| 292-305 | -4% | 0% | 2% | 15% | -4% | -4% | 1% |
| 295-305 | 6% | -1% | -4% | -4% | -4% | 3% | -1% |
| 301-305 | -8% | -4% | 8% | 8% | 4% | -12% | -1% |
| 311-318 | -25% | -19% | -9% | -6% | -8% | -1% | -11% |
| 311-326 | -26% | -28% | -23% | -21% | -9% | -6% | -19% |
| 312-326 | -24% | -25% | -20% | -15% | -7% | -6% | -16% |
| 321-326 | -14% | -22% | -27% | -30% | -16% | -15% | -21% |
| 329-330 | -26% | -23% | -19% | -36% | -33% | -47% | -31% |
| 329-331 | -7% | -7% | -8% | -10% | -18% | -44% | -16% |
| 332-333 | -1% | 5% | -4% | 4% | -1% | -15% | -2% |
| 334-342 | 14% | 9% | 2% | -5% | 4% | -6% | 3% |
| 336-345 | 2% | 4% | -3% | 3% | -1% | 0% | 1% |
| 344-346 | Not detected | Not detected | Not detected | Not detected | Not detected | Not detected | Not detected |
| 345-346 | 4% | 4% | 3% | 3% | 4% | -11% | 1% |
| 347-349 | Not detected | Not detected | Not detected | Not detected | Not detected | Not detected | Not detected |
| 348-349 | 2% | -8% | -14% | 2% | -2% | -13% | -6% |
| 348-357 | Not detected | Not detected | Not detected | Not detected | Not detected | Not detected | Not detected |
| 349-357 | -1% | -7% | -2% | -3% | -2% | -6% | -4% |
| 373-384 | 6% | 0% | 4% | 6% | 3% | 5% | 4% |
| 376-384 | 2% | 1% | -1% | 3% | 0% | -3% | 0% |
| 380-384 | Not detected | Not detected | Not detected | Not detected | Not detected | Not detected | Not detected |

Incubation Time (Seconds)

SEQUENCE LISTING

```
<160> NUMBER OF SEQ ID NOS: 158

<210> SEQ ID NO 1
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
            20                  25                  30

Leu Ser Trp Tyr Gln Gln Lys Pro Gly Lys Ala Pro Lys Leu Leu Ile
        35                  40                  45

Leu Ala Phe Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105

<210> SEQ ID NO 2
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Thr
            20                  25                  30
```

```
Leu Ser Trp Tyr Gln Gln Lys Pro Gly Lys Ala Pro Lys Leu Leu Ile
            35                  40                  45

Leu Trp Asn Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Ala Gly Thr His Pro Thr
                 85                  90                  95

Thr Phe Gly Gln Gly Thr Lys Val Glu Ile Lys Arg
            100                 105
```

<210> SEQ ID NO 3
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 3

```
gacatccaga tgacccagtc tccatcctcc ctgtctgcat ctgtaggaga ccgtgtcacc    60
atcacttgcc gggcaagtcg tccgattggg acgatgttaa gttggtacca gcagaaacca   120
gggaaagccc ctaagctcct gatccttgct ttttcccgtt tgcaaagtgg ggtcccatca   180
cgtttcagtg gcagtggatc tgggacagat ttcactctca ccatcagcag tctgcaacct   240
gaagattttg ctacgtacta ctgcgcgcag gctgggacgc atcctacgac gttcggccaa   300
gggaccaagg tggaaatcaa acgg                                           324
```

<210> SEQ ID NO 4
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 4

```
gacatccaga tgacccagtc tccatcctcc ctgtctgcat ctgtaggaga ccgtgtcacc    60
atcacttgcc gggcaagtcg tccgattggg acgacgttaa gttggtacca gcagaaacca   120
gggaaagccc ctaagctcct gatcctttgg aattcccgtt tgcaaagtgg ggtcccatca   180
cgtttcagtg gcagtggatc tgggacagat ttcactctca ccatcagcag tctgcaacct   240
gaagattttg ctacgtacta ctgtgcgcag gctgggacgc atcctacgac gttcggccaa   300
gggaccaagg tggaaatcaa acgg                                           324
```

<210> SEQ ID NO 5
<211> LENGTH: 163
<212> TYPE: PRT
<213> ORGANISM: mus musculus

<400> SEQUENCE: 5

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Pro Ser Gly Gly Gly Gly Ser Gly Gly Gly
            35                  40                  45

Gly Ser Gly Gly Gly Gly Ser Asp Ile Gln Met Thr Gln Ser Pro Ser
```

```
Ser Leu Ser Ala Ser Val Gly Asp Arg Val Thr Ile Thr Cys Arg Ala
 65                  70                  75                  80

Ser Gln Trp Ile Gly Ser Gln Leu Ser Trp Tyr Gln Gln Lys Pro Gly
                 85                  90                  95

Lys Ala Pro Lys Leu Leu Ile Met Trp Arg Ser Ser Leu Gln Ser Gly
            100                 105                 110

Val Pro Ser Arg Phe Ser Gly Ser Gly Ser Gly Thr Asp Phe Thr Leu
        115                 120                 125

Thr Ile Ser Ser Leu Gln Pro Glu Asp Phe Ala Thr Tyr Tyr Cys Ala
    130                 135                 140

Gln Gly Ala Ala Leu Pro Arg Thr Phe Gly Gln Gly Thr Lys Val Glu
145                 150                 155                 160

Ile Lys Arg

<210> SEQ ID NO 6
<211> LENGTH: 489
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 6
catggtgaag gaacatttac cagtgacttg tcaaaacaga tggaagagga ggcagtgcgg     60
ttatttattg agtggcttaa gaacggagga ccaagtagcg gggcacctcc gccatcgggt   120
ggtggaggcg gttcaggcgg aggtggcagc ggcggtggcg ggtcggacat ccagatgacc   180
cagtctccat cctccctgtc tgcatctgta ggagaccgtg tcaccatcac ttgccgggca   240
agtcagtgga ttgggtctca gttatcttgg taccagcaga accagggaa agcccctaag   300 ctcctgatca tgtggcgttc ctcgttgcaa agtggggtcc catcacgttt cagtggcagt   360
ggatctggga cagatttcac tctcaccatc agcagtctgc aacctgaaga ttttgctacg   420
tactactgtg ctcagggtgc ggcgttgcct aggacgttcg gccaagggac caaggtggaa   480
atcaaacgg                                                           489

<210> SEQ ID NO 7
<211> LENGTH: 163
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 7

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Ser Gly Gly Gly Gly Ser Gly Gly Gly
         35                  40                  45

Gly Ser Gly Gly Gly Ser Asp Ile Gln Met Thr Gln Ser Pro Ser
 50                  55                  60

Ser Leu Ser Ala Ser Val Gly Asp Arg Val Thr Ile Thr Cys Arg Ala
 65                  70                  75                  80

Ser Gln Trp Ile Gly Ser Gln Leu Ser Trp Tyr Gln Gln Lys Pro Gly
                 85                  90                  95
```

Lys Ala Pro Lys Leu Leu Ile Met Trp Arg Ser Ser Leu Gln Ser Gly
                100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
130                 135                 140

Gln Gly Leu Arg His Pro Lys Thr Phe Gly Gln Gly Thr Lys Val Glu
145                 150                 155                 160

Ile Lys Arg

<210> SEQ ID NO 8
<211> LENGTH: 489
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 8
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcagtgga ttgggtctca gttatcttgg taccagcaga accagggaa agcccctaag      300 ctcctgatca tgtggcgttc ctcgttgcaa agtggggtcc catcacgttt cagtggcagt     360
ggatctggga cagatttcac tctcaccatc agcagtctgc aacctgaaga ttttgctacg     420
tactactgtg ctcagggttt gaggcatcct aagacgttcg gccaagggac caaggtggaa     480
atcaaacgg                                                            489

<210> SEQ ID NO 9
<211> LENGTH: 163
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Gly Ser Gly Gly Gly
        35                  40                  45

Gly Ser Gly Gly Gly Gly Ser Asp Ile Gln Met Thr Gln Ser Pro Ser
50                  55                  60

Ser Leu Ser Ala Ser Val Gly Asp Arg Val Thr Ile Thr Cys Arg Ala
65                  70                  75                  80

Ser Arg Pro Ile Gly Thr Thr Leu Ser Trp Tyr Gln Gln Lys Pro Gly
                85                  90                  95

Lys Ala Pro Lys Leu Leu Ile Trp Phe Gly Ser Arg Leu Gln Ser Gly
                100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
    130                 135                 140

Gln Ala Gly Thr His Pro Thr Thr Phe Gly Gln Gly Thr Lys Val Glu
145                 150                 155                 160

Ile Lys Arg

<210> SEQ ID NO 10
<211> LENGTH: 489
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 10
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcgtccga ttgggacgac gttaagttgg taccagcaga aaccagggaa agcccctaag     300
ctcctgatct ggtttggttc ccggttgcaa agtggggtcc catcacgttt cagtggcagt     360
ggatctggga cagatttcac tctcaccatc agcagtctgc aacctgaaga ttttgctacg     420
tactactgtg cgcaggctgg gacgcatcct acgacgttcg gccagggac caaggtggaa     480 atcaaacgg                                                             489

<210> SEQ ID NO 11
<211> LENGTH: 163
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 11

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Ser Gly Gly Gly Gly Ser Gly Gly Gly
         35                  40                  45

Gly Ser Gly Gly Gly Gly Ser Asp Ile Gln Met Thr Gln Ser Pro Ser
 50                  55                  60

Ser Leu Ser Ala Ser Val Gly Asp Arg Val Thr Ile Thr Cys Arg Ala
 65                  70                  75                  80

Ser Arg Pro Ile Gly Thr Met Leu Ser Trp Tyr Gln Gln Lys Pro Gly
                 85                  90                  95

Lys Ala Pro Lys Leu Leu Ile Leu Ala Phe Ser Arg Leu Gln Ser Gly
            100                 105                 110

Val Pro Ser Arg Phe Ser Gly Ser Gly Ser Gly Thr Asp Phe Thr Leu
        115                 120                 125

Thr Ile Ser Ser Leu Gln Pro Glu Asp Phe Ala Thr Tyr Tyr Cys Ala
    130                 135                 140

Gln Ala Gly Thr His Pro Thr Thr Phe Gly Gln Gly Thr Lys Val Glu
145                 150                 155                 160

Ile Lys Arg

<210> SEQ ID NO 12
<211> LENGTH: 489
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 12

```
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcgtccga ttgggacgat gttaagttgg taccagcaga accagggaaa gcccctaag     300
ctcctgatcc ttgcttttcc cgtttgcaa agtgggtcc catcacgttt cagtggcagt     360
ggatctggga cagatttcac tctcaccatc agcagtctgc aacctgaaga ttttgctacg     420
tactactgcg cgcaggctgg gacgcatcct acgacgttcg gccaaggac caaggtggaa     480
atcaaacgg                                                             489
```

<210> SEQ ID NO 13
<211> LENGTH: 114
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 13

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Gln
             20                  25                  30

Leu Ser Trp Tyr Gln Gln Lys Pro Gly Lys Ala Pro Lys Leu Leu Ile
         35                  40                  45

Met Trp Arg Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Arg Gly Gly Gly Gly
            100                 105                 110

Ser Cys
```

<210> SEQ ID NO 14
<211> LENGTH: 345
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 14

```
gacatccaga tgacccagtc tccatcctcc ctgtctgcat ctgtaggaga ccgtgtcacc      60
atcacttgcc gggcaagtca gtggattggg tctcagttat cttggtacca gcagaaacca    120
```

```
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggc atcctaagac gttcggccaa    300
gggaccaagg tggaaatcaa acggggtggc ggagggggtt cctgt                    345
```

<210> SEQ ID NO 15
<211> LENGTH: 115
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 15

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Trp Ile Gly Ser Gln
             20                  25                  30

Leu Ser Trp Tyr Gln Gln Lys Pro Gly Lys Ala Pro Lys Leu Leu Ile
         35                  40                  45

Met Trp Arg Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Arg Thr Val Ala Ala
            100                 105                 110

Pro Ser Cys
        115
```

<210> SEQ ID NO 16
<211> LENGTH: 345
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 16

```
gacatccaga tgacccagtc tccatcctcc ctgtctgcat ctgtaggaga ccgtgtcacc    60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggc atcctaagac gttcggccaa    300
gggaccaagg tggaaatcaa acggaccgtc gctgctccat cttgt                    345
```

<210> SEQ ID NO 17
<211> LENGTH: 235
<212> TYPE: PRT
<213> ORGANISM: mus musculus

<400> SEQUENCE: 17

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Arg Tyr
             20                  25                  30
```

-continued

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
 50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
            115                 120                 125

Ile Gln Met Thr Gln Ser Pro Ser Ser Leu Ser Ala Ser Val Gly Asp
        130                 135                 140

Arg Val Thr Ile Thr Cys Arg Ala Ser Arg Pro Ile Gly Thr Thr Leu
145                 150                 155                 160

Ser Trp Tyr Gln Gln Lys Pro Gly Lys Ala Pro Lys Leu Leu Ile Trp
                165                 170                 175

Phe Gly Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
    210                 215                 220

Phe Gly Gln Gly Thr Lys Val Glu Ile Lys Arg
225                 230                 235

<210> SEQ ID NO 18
<211> LENGTH: 249
<212> TYPE: PRT
<213> ORGANISM: Artificial Sequence
<220> FEATURE:
<223> OTHER INFORMATION: Amino acid plus myc tag

<400> SEQUENCE: 18

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
 50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
            115                 120                 125

Ile Gln Met Thr Gln Ser Pro Ser Ser Leu Ser Ala Ser Val Gly Asp
        130                 135                 140

Arg Val Thr Ile Thr Cys Arg Ala Ser Arg Pro Ile Gly Thr Thr Leu
145                 150                 155                 160

Ser Trp Tyr Gln Gln Lys Pro Gly Lys Ala Pro Lys Leu Leu Ile Trp
            165                 170                 175

Phe Gly Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
            195                 200                 205

Asp Phe Ala Thr Tyr Tyr Cys Ala Gln Ala Gly Thr His Pro Thr Thr
            210                 215                 220

Phe Gly Gln Gly Thr Lys Val Glu Ile Lys Arg Ala Ala Ala Glu Gln
225                 230                 235                 240

Lys Leu Ile Ser Glu Glu Asp Leu Asn
            245

<210> SEQ ID NO 19
<211> LENGTH: 705
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 19
gaggtgcagc tgttggagtc tgggggaggc ttggtacagc ctgggggtc cctgcgtctc        60 tcctgtgcag cctccggatt cacctttaat aggtatagta tggggtggct ccgccaggct      120
ccagggaagg gtctagagtg ggtctcacgg attgattctt atggtcgtgg tacatactac      180
gaagaccccg tgaagggccg gttcagcatc tcccgcgaca attccaagaa cacgctgtat      240
ctgcaaatga acagcctgcg tgccgaggac accgccgtat attactgtgc gaaaatttct      300
cagtttgggt caaatgcgtt tgactactgg ggtcagggaa cccaggtcac cgtctcgagc      360
gctagcacca gtggtccatc ggacatccag atgacccagt ctccatcctc cctgtctgca      420
tctgtaggag accgtgtcac catcacttgc cgggcaagtc gtccgattgg gacgacgtta      480
agttggtacc agcagaaacc agggaaagcc cctaagctcc tgatctggtt tggttcccgg      540
ttgcaaagtg gggtcccatc acgtttcagt ggcagtggat ctgggacaga tttcactctc      600
accatcagca gtctgcaacc tgaagatttt gctacgtact actgtgcgca ggctgggacg      660
catcctacga cgttcggcca agggaccaag gtggaaatca aacgg                      705

<210> SEQ ID NO 20
<211> LENGTH: 750
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 20
gaggtgcagc tgttggagtc tgggggaggc ttggtacagc ctgggggtc cctgcgtctc        60 tcctgtgcag cctccggatt cacctttaat aggtatagta tggggtggct ccgccaggct      120
ccagggaagg gtctagagtg ggtctcacgg attgattctt atggtcgtgg tacatactac      180
gaagaccccg tgaagggccg gttcagcatc tcccgcgaca attccaagaa cacgctgtat      240
ctgcaaatga acagcctgcg tgccgaggac accgccgtat attactgtgc gaaaatttct      300
cagtttgggt caaatgcgtt tgactactgg ggtcagggaa cccaggtcac cgtctcgagc      360
gctagcacca gtggtccatc ggacatccag atgacccagt ctccatcctc cctgtctgca      420

```
tctgtaggag accgtgtcac catcacttgc cggcaagtc gtccgattgg gacgacgtta    480
agttggtacc agcagaaacc agggaaagcc cctaagctcc tgatctggtt tggttcccgg    540
ttgcaaagtg gggtcccatc acgtttcagt ggcagtggat ctgggacaga tttcactctc    600
accatcagca gtctgcaacc tgaagatttt gctacgtact actgtgcgca ggctgggacg    660
catcctacga cgttcggcca agggaccaag gtggaaatca aacgggcggc cgcagaacaa    720
aaactcatct cagaagagga tctgaattaa                                     750
```

<210> SEQ ID NO 21
<211> LENGTH: 235
<212> TYPE: PRT
<213> ORGANISM: Artificial Sequence
<220> FEATURE:
<223> OTHER INFORMATION: Amino acid sequence identified using molecular biology techniques.

<400> SEQUENCE: 21

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Arg Ala Ser Arg Pro Ile Gly Thr Met Leu
145                 150                 155                 160

Ser Trp Tyr Gln Gln Lys Pro Gly Lys Ala Pro Lys Leu Leu Ile Leu
                165                 170                 175

Ala Phe Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
    210                 215                 220

Phe Gly Gln Gly Thr Lys Val Glu Ile Lys Arg
225                 230                 235
```

<210> SEQ ID NO 22
<211> LENGTH: 249
<212> TYPE: PRT
<213> ORGANISM: Artificial Sequence
<220> FEATURE:
<223> OTHER INFORMATION: Amino acid plus nucleotide plus myc tag

<400> SEQUENCE: 22

```
Glu Val Gln Leu Leu Glu Ser Gly Gly Gly Leu Val Gln Pro Gly Gly
```

```
                1               5                   10                  15
            Ser Leu Arg Leu Ser Cys Ala Ala Ser Gly Phe Thr Phe Asn Arg Tyr
                        20                  25                  30
            Ser Met Gly Trp Leu Arg Gln Ala Pro Gly Lys Gly Leu Glu Trp Val
                        35                  40                  45
            Ser Arg Ile Asp Ser Tyr Gly Arg Gly Thr Tyr Tyr Glu Asp Pro Val
                        50                  55                  60
            Lys Gly Arg Phe Ser Ile Ser Arg Asp Asn Ser Lys Asn Thr Leu Tyr
             65                  70                  75                  80
            Leu Gln Met Asn Ser Leu Arg Ala Glu Asp Thr Ala Val Tyr Tyr Cys
                            85                  90                  95
            Ala Lys Ile Ser Gln Phe Gly Ser Asn Ala Phe Asp Tyr Trp Gly Gln
                            100                 105                 110
            Gly Thr Gln Val Thr Val Ser Ser Ala Ser Thr Ser Gly Pro Ser Asp
                            115                 120                 125
            Ile Gln Met Thr Gln Ser Pro Ser Ser Leu Ser Ala Ser Val Gly Asp
                        130                 135                 140
            Arg Val Thr Ile Thr Cys Arg Ala Ser Arg Pro Ile Gly Thr Met Leu
            145                 150                 155                 160
            Ser Trp Tyr Gln Gln Lys Pro Gly Lys Ala Pro Lys Leu Leu Ile Leu
                            165                 170                 175
            Ala Phe Ser Arg Leu Gln Ser Gly Val Pro Ser Arg Phe Ser Gly Ser
                        180                 185                 190
            Gly Ser Gly Thr Asp Phe Thr Leu Thr Ile Ser Ser Leu Gln Pro Glu
                        195                 200                 205
            Asp Phe Ala Thr Tyr Tyr Cys Ala Gln Ala Gly Thr His Pro Thr Thr
                        210                 215                 220
            Phe Gly Gln Gly Thr Lys Val Glu Ile Lys Arg Ala Ala Ala Glu Gln
            225                 230                 235                 240
            Lys Leu Ile Ser Glu Glu Asp Leu Asn
                            245

<210> SEQ ID NO 23
<211> LENGTH: 705
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 23
gaggtgcagc tgttggagtc tgggggaggc ttggtacagc ctggggggtc cctgcgtctc    60
tcctgtgcag cctccggatt cacctttaat aggtatagta tggggtggct ccgccaggct   120
ccagggaagg gtctagagtg ggtctcacgg attgattctt atggtcgtgg tacatactac   180
gaagaccccg tgaagggccg gttcagcatc tcccgcgaca attccaagaa cacgctgtat   240
ctgcaaatga acagcctgcg tgccgaggac accgccgtat attactgtgc gaaaatttct   300
cagtttgggt caaatgcgtt tgactactgg ggtcagggaa cccaggtcac cgtctcgagc   360
gctagcacca gtggtccatc ggacatccag atgacccagt ctccatcctc cctgtctgca   420
tctgtaggag accgtgtcac catcacttgc cgggcaagtc gtccgattgg acgatgttta   480
agttggtacc agcagaaacc agggaaagcc cctaagctcc tgatccttgc ttttcccgt    540
ttgcaaagtg ggtcccatc acgtttcagt ggcagtggat ctgggacaga tttcactctc   600
accatcagca gtctgcaacc tgaagatttt gctacgtact actgcgcgca ggctgggacg   660
```

```
catcctacga cgttcggcca agggaccaag gtggaaatca aacgg              705
```

<210> SEQ ID NO 24
<211> LENGTH: 750
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 24

```
gaggtgcagc tgttggagtc tgggggaggc ttggtacagc ctgggggtc cctgcgtctc     60
tcctgtgcag cctccggatt caccttaat aggtatagta tggggtggct ccgccaggct   120
ccagggaagg gtctagagtg ggtctcacgg attgattctt atggtcgtgg tacatactac   180
gaagaccccg tgaagggccg gttcagcatc tcccgcgaca attccaagaa cacgctgtat   240
ctgcaaatga acagcctgcg tgccgaggac accgccgtat attactgtgc gaaaatttct   300
cagtttgggt caaatgcgtt tgactactgg ggtcaggaa cccaggtcac cgtctcgagc   360
gctagcacca gtggtccatc ggacatccag atgacccagt ctccatcctc cctgtctgca   420
tctgtaggag accgtgtcac catcacttgc cgggcaagtc gtccgattgg gacgatgtta   480
agttggtacc agcagaaacc agggaaagcc cctaagctcc tgatccttgc tttttcccgt   540
ttgcaaagtg ggtccccatc acgtttcagt ggcagtggat ctgggacaga tttcactctc   600
accatcagca gtctgcaacc tgaagatttt gctacgtact actgcgcgca ggctgggacg   660
catcctacga cgttcggcca agggaccaag gtggaaatca aacgggcggc cgcagaacaa   720
aaactcatct cagaagagga tctgaattaa                                   750
```

<210> SEQ ID NO 25
<211> LENGTH: 9
<212> TYPE: PRT
<213> ORGANISM: Artificial Sequence
<220> FEATURE:
<223> OTHER INFORMATION: CDR 1 amino acid sequence identified using
      molecular biology techniques.

<400> SEQUENCE: 25

Ser Gln Ser Ile Ser Ser Tyr Leu Asn
 1               5

<210> SEQ ID NO 26
<211> LENGTH: 8
<212> TYPE: PRT
<213> ORGANISM: Artificial Sequence
<220> FEATURE:
<223> OTHER INFORMATION: CDR 2 amino acid sequence identified using
      molecular biology techniques.

<400> SEQUENCE: 26

Tyr Ala Ala Ser Ser Leu Gln Ser
 1               5

<210> SEQ ID NO 27
<211> LENGTH: 9
<212> TYPE: PRT
<213> ORGANISM: Artificial Sequence
<220> FEATURE:
<223> OTHER INFORMATION: CDR 3 amino acid sequence identified using
      molecular biology techniques.

<400> SEQUENCE: 27

Gln Gln Ser Tyr Ser Thr Pro Asn Thr
1               5

<210> SEQ ID NO 28
<211> LENGTH: 9
<212> TYPE: PRT
<213> ORGANISM: Artificial Sequence
<220> FEATURE:
<223> OTHER INFORMATION: CDR 1 amino acid sequence identified using
      molecular biology techniques.

<400> SEQUENCE: 28

Ser Arg Pro Ile Gly Thr Thr Leu Ser
1               5

<210> SEQ ID NO 29
<211> LENGTH: 8
<212> TYPE: PRT
<213> ORGANISM: Artificial Sequence
<220> FEATURE:
<223> OTHER INFORMATION: CDR 2 amino acid sequence identified using
      molecular biology techniques.

<400> SEQUENCE: 29

Trp Phe Gly Ser Arg Leu Gln Ser
1               5

<210> SEQ ID NO 30
<211> LENGTH: 9
<212> TYPE: PRT
<213> ORGANISM: Artificial Sequence
<220> FEATURE:
<223> OTHER INFORMATION: CDR 3 amino acid sequence identified using
      molecular biology techniques.

<400> SEQUENCE: 30

Ala Gln Ala Gly Thr His Pro Thr Thr
1               5

<210> SEQ ID NO 31
<211> LENGTH: 9
<212> TYPE: PRT
<213> ORGANISM: Artificial Sequence
<220> FEATURE:
<223> OTHER INFORMATION: CDR 1 amino acid sequence identified using
      molecular biology techniques.

<400> SEQUENCE: 31

Ser Arg Pro Ile Gly Thr Met Leu Ser
1               5

<210> SEQ ID NO 32
<211> LENGTH: 8
<212> TYPE: PRT
<213> ORGANISM: Artificial Sequence
<220> FEATURE:
<223> OTHER INFORMATION: CDR 2 amino acid sequence identified using
      molecular biology techniques.

<400> SEQUENCE: 32

Leu Ala Phe Ser Arg Leu Gln Ser
1               5

<210> SEQ ID NO 33
<211> LENGTH: 9
<212> TYPE: PRT
<213> ORGANISM: Artificial Sequence
<220> FEATURE:

```
<223> OTHER INFORMATION: CDR 3 amino acid sequence identified using
      molecular biology techniques.

<400> SEQUENCE: 33

Ala Gln Ala Gly Thr His Pro Thr Thr
1               5

<210> SEQ ID NO 34
<211> LENGTH: 9
<212> TYPE: PRT
<213> ORGANISM: Artificial Sequence
<220> FEATURE:
<223> OTHER INFORMATION: CDR 1 amino acid sequence identified using
      molecular biology techniques.

<400> SEQUENCE: 34

Ser Arg Pro Ile Gly Thr Thr Leu Ser
1               5

<210> SEQ ID NO 35
<211> LENGTH: 8
<212> TYPE: PRT
<213> ORGANISM: Artificial Sequence
<220> FEATURE:
<223> OTHER INFORMATION: CDR 2 amino acid sequence identified using
      molecular biology techniques.

<400> SEQUENCE: 35

Leu Trp Phe Ser Arg Leu Gln Ser
1               5

<210> SEQ ID NO 36
<211> LENGTH: 9
<212> TYPE: PRT
<213> ORGANISM: Artificial Sequence
<220> FEATURE:
<223> OTHER INFORMATION: CDR 3 amino acid sequence identified using
      molecular biology techniques.

<400> SEQUENCE: 36

Ala Gln Ala Gly Thr His Pro Thr Thr
1               5

<210> SEQ ID NO 37
<211> LENGTH: 9
<212> TYPE: PRT
<213> ORGANISM: Artificial Sequence
<220> FEATURE:
<223> OTHER INFORMATION: CDR 1 amino acid sequence identified using
      molecular biology techniques.

<400> SEQUENCE: 37

Ser Gln Trp Ile Gly Ser Gln Leu Ser
1               5

<210> SEQ ID NO 38
<211> LENGTH: 8
<212> TYPE: PRT
<213> ORGANISM: Artificial Sequence
<220> FEATURE:
<223> OTHER INFORMATION: CDR 2 amino acid sequence identified using
      molecular biology techniques.

<400> SEQUENCE: 38

Met Trp Arg Ser Ser Leu Gln Ser
1               5
```

```
<210> SEQ ID NO 39
<211> LENGTH: 9
<212> TYPE: PRT
<213> ORGANISM: Artificial Sequence
<220> FEATURE:
<223> OTHER INFORMATION: CDR 3 amino acid sequence identified using
      molecular biology techniques.

<400> SEQUENCE: 39

Ala Gln Gly Ala Ala Leu Pro Arg Thr
1               5

<210> SEQ ID NO 40
<211> LENGTH: 9
<212> TYPE: PRT
<213> ORGANISM: Artificial Sequence
<220> FEATURE:
<223> OTHER INFORMATION: CDR 1 amino acid sequence identified using
      molecular biology techniques.

<400> SEQUENCE: 40

Ser Gln Trp Ile Gly Ser Gln Leu Ser
1               5

<210> SEQ ID NO 41
<211> LENGTH: 8
<212> TYPE: PRT
<213> ORGANISM: Artificial Sequence
<220> FEATURE:
<223> OTHER INFORMATION: CDR 2 amino acid sequence identified using
      molecular biology techniques.

<400> SEQUENCE: 41

Met Trp Arg Ser Ser Leu Gln Ser
1               5

<210> SEQ ID NO 42
<211> LENGTH: 9
<212> TYPE: PRT
<213> ORGANISM: Artificial Sequence
<220> FEATURE:
<223> OTHER INFORMATION: CDR 3 amino acid sequence identified using
      molecular biology techniques.

<400> SEQUENCE: 42

Ala Gln Gly Leu Arg His Pro Lys Thr
1               5

<210> SEQ ID NO 43
<211> LENGTH: 165
<212> TYPE: PRT
<213> ORGANISM: Artificial Sequence
<220> FEATURE:
<223> OTHER INFORMATION: Interferon alpha 2b amino acid sequence
      identified using molecular biology techniques.

<400> SEQUENCE: 43

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
```

```
              65                  70                  75                  80
Leu Asp Lys Phe Tyr Thr Glu Leu Tyr Gln Gln Leu Asn Asp Leu Glu
                    85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 44
<211> LENGTH: 495
<212> TYPE: DNA
<213> ORGANISM: Artificial Sequence
<220> FEATURE:
<223> OTHER INFORMATION: Interferon alpha 2b nucleic acid sequence
      identified using molecular biology techniques.

<400> SEQUENCE: 44
tgtgatctgc ctcaaaccca cagcctgggt agcaggagga ccttgatgct cctggcacag     60
atgaggagaa tctctctttt ctcctgcttg aaggacagac atgactttgg atttccccag    120
gaggagtttg gcaaccagtt ccaaaaggct gaaaccatcc ctgtcctcca tgagatgatc    180
cagcagatct tcaatctctt cagcacaaag gactcatctg ctgcttggga tgagaccctc    240
ctagacaaat tctacactga actctaccag cagctgaatg acctggaagc ctgtgtgata    300 caggggggtgg gggtgacaga gactcccctg atgaaggagg actccattct ggctgtgagg    360
aaatacttcc aaagaatcac tctctatctg aaagagaaga atacagcccc ttgtgcctgg    420
gaggttgtca gcagaaaat catgagatct ttttctttgt caacaaactt gcaagaaagt    480
ttaagaagta aggaa                                                     495

<210> SEQ ID NO 45
<211> LENGTH: 25
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 45
gcccggatcc accggctgtg atctg                                           25

<210> SEQ ID NO 46
<211> LENGTH: 30
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 46
ggaggatgga gactgggtca tctggatgtc                                      30

<210> SEQ ID NO 47
<211> LENGTH: 30
<212> TYPE: DNA
```

```
<213> ORGANISM: Artificial Sequence
<220> FEATURE:
<223> OTHER INFORMATION: Nucleic acid sequence identified using
      molecular biology techniques.

<400> SEQUENCE: 47
gacatccaga tgacccagtc tccatcctcc                                        30

<210> SEQ ID NO 48
<211> LENGTH: 82
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 48
gcgcaagctt ttattaattc agatcctctt ctgagatgag ttttgttct gcggccgccc        60 gtttgatttc caccttggtc cc                                                82

<210> SEQ ID NO 49
<211> LENGTH: 25
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 49
gcccggatcc accggctgtg atctg                                             25

<210> SEQ ID NO 50
<211> LENGTH: 82
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 50
gcgcaagctt ttattaattc agatcctctt ctgagatgag ttttgttct gcggccgccc        60 gtttgatttc caccttggtc cc                                                82

<210> SEQ ID NO 51
<211> LENGTH: 20
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 51

Met Glu Thr Asp Thr Leu Leu Leu Trp Val Leu Leu Leu Trp Val Pro
 1               5                  10                  15

Gly Ser Thr Gly
            20

<210> SEQ ID NO 52
<211> LENGTH: 61
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 52
```

```
atggagaccg acaccctgct gctgtgggtg ctgctgctgt gggtgcccgg atccaccggg    60
c                                                                   61
```

<210> SEQ ID NO 53
<211> LENGTH: 293
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 53

```
Cys Asp Leu Pro Gln Thr His Ser Leu Gly Ser Arg Arg Thr Leu Met
  1               5                  10                  15
Leu Leu Ala Gln Met Arg Arg Ile Ser Leu Phe Ser Cys Leu Lys Asp
                 20                  25                  30
Arg His Asp Phe Gly Phe Pro Gln Glu Glu Phe Gly Asn Gln Phe Gln
             35                  40                  45
Lys Ala Glu Thr Ile Pro Val Leu His Glu Met Ile Gln Gln Ile Phe
         50                  55                  60
Asn Leu Phe Ser Thr Lys Asp Ser Ser Ala Ala Trp Asp Glu Thr Leu
 65                  70                  75                  80
Leu Asp Lys Phe Tyr Thr Glu Leu Tyr Gln Gln Leu Asn Asp Leu Glu
                 85                  90                  95
Ala Cys Val Ile Gln Gly Val Gly Val Thr Glu Thr Pro Leu Met Lys
            100                 105                 110
Glu Asp Ser Ile Leu Ala Val Arg Lys Tyr Phe Gln Arg Ile Thr Leu
            115                 120                 125
Tyr Leu Lys Glu Lys Lys Tyr Ser Pro Cys Ala Trp Glu Val Val Arg
        130                 135                 140
Ala Glu Ile Met Arg Ser Phe Ser Leu Ser Thr Asn Leu Gln Glu Ser
145                 150                 155                 160
Leu Arg Ser Lys Glu Thr Val Ala Ala Pro Ser Asp Ile Gln Met Thr
                165                 170                 175
Gln Ser Pro Ser Ser Leu Ser Ala Ser Val Gly Asp Arg Val Thr Ile
            180                 185                 190
Thr Cys Arg Ala Ser Gln Trp Ile Gly Ser Gln Leu Ser Trp Tyr Gln
            195                 200                 205
Gln Lys Pro Gly Lys Ala Pro Lys Leu Leu Ile Met Trp Arg Ser Ser
        210                 215                 220
Leu Gln Ser Gly Val Pro Ser Arg Phe Ser Gly Ser Gly Ser Gly Thr
225                 230                 235                 240
Asp Phe Thr Leu Thr Ile Ser Ser Leu Gln Pro Glu Asp Phe Ala Thr
                245                 250                 255
Tyr Tyr Cys Ala Gln Gly Ala Ala Leu Pro Arg Thr Phe Gly Gln Gly
            260                 265                 270
Thr Lys Val Glu Ile Lys Arg Ala Ala Ala Glu Gln Lys Leu Ile Ser
            275                 280                 285
Glu Glu Asp Leu Asn
        290
```

<210> SEQ ID NO 54
<211> LENGTH: 882
<212> TYPE: DNA
<213> ORGANISM: Artificial Sequence
<220> FEATURE:

<223> OTHER INFORMATION: Nucleic acid sequence identified using
      molecular biology techniques.

<400> SEQUENCE: 54

```
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aaggaaaaga aatactcccc atgtgcatgg     420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcagtggatt     600
gggtctcagt tatcttggta ccagcagaaa ccagggaaag cccctaagct cctgatcatg     660
tggcgttcct cgttgcaaag tggggtccca tcacgtttca gtggcagtgg atctgggaca     720
gatttcactc tcaccatcag cagtctgcaa cctgaagatt ttgctacgta ctactgtgct     780
cagggtgcgg cgttgcctag gacgttcggc caagggacca aggtggaaat caaacgggcg     840
gccgcagaac aaaaactcat ctcagaagag gatctgaatt aa                        882
```

<210> SEQ ID NO 55
<211> LENGTH: 279
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 55

```
Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175
```

Gln Ser Pro Ser Ser Leu Ser Ala Ser Val Gly Asp Arg Val Thr Ile
            180                 185                 190

Thr Cys Arg Ala Ser Gln Trp Ile Gly Ser Gln Leu Ser Trp Tyr Gln
        195                 200                 205

Gln Lys Pro Gly Lys Ala Pro Lys Leu Leu Ile Met Trp Arg Ser Ser
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Ala Ala Leu Pro Arg Thr Phe Gly Gln Gly
            260                 265                 270

Thr Lys Val Glu Ile Lys Arg
        275

<210> SEQ ID NO 56
<211> LENGTH: 837
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 56
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaagaag attcaattct agccgttaga     360
aaatactttc agcgtatcac attgtattta aaggaaaaga atactccccc atgtgcatgg     420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcagtggatt     600
gggtctcagt tatcttggta ccagcagaaa ccagggaaag cccctaagct cctgatcatg     660
tggcgttcct cgttgcaaag tggggtccca tcacgtttca gtggcagtgg atctgggaca     720
gatttcactc tcaccatcag cagtctgcaa cctgaagatt ttgctacgta ctactgtgct     780
cagggtgcgg cgttgcctag gacgttcggc caagggacca aggtggaaat caaacgg       837

<210> SEQ ID NO 57
<211> LENGTH: 293
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 57

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
            50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
                180                 185                 190

Thr Cys Arg Ala Ser Gln Trp Ile Gly Ser Gln Leu Ser Trp Tyr Gln
            195                 200                 205

Gln Lys Pro Gly Lys Ala Pro Lys Leu Leu Ile Met Trp Arg Ser Ser
210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Leu Arg His Pro Lys Thr Phe Gly Gln Gly
            260                 265                 270

Thr Lys Val Glu Ile Lys Arg Ala Ala Ala Glu Gln Lys Leu Ile Ser
            275                 280                 285

Glu Glu Asp Leu Asn
    290

<210> SEQ ID NO 58
<211> LENGTH: 882
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 58
tgcgacttgc cacagacaca tagtttggga tcaagaagaa cattgatgtt attagcacaa      60
atgcgtagaa tttctttgtt ctcttgtcta aaggaccgtc acgacttcgg attccctcag    120
gaagagtttg aaaccaatt ccaaaaagca gaaactattc ctgtcttgca cgaaatgatc     180
cagcaaatat tcaatttgtt ttctacaaag gactcatcag ccgcttggga tgaaactctg    240
ttagataaat tctacactga actatatcaa caactgaacg atctagaggc ttgcgttatt    300
cagggtgtag gagttactga aactccccta atgaaagaag attcaattct agccgttaga    360
aaatactttc agcgtatcac attgtattta aaggaaaaga aatactcccc atgtgcatgg    420
gaggtggtta gagcagaaat tatgaggtcc ttctctcttt ctacgaattt gcaagaatct    480
ttgagatcta aggaaaccgt cgctgctcca tctgacatcc agatgaccca gtctccatcc    540
tccctgtctg catctgtagg agaccgtgtc accatcactt gccgggcaag tcagtggatt    600

```
gggtctcagt tatcttggta ccagcagaaa ccagggaaag cccctaagct cctgatcatg    660
tggcgttcct cgttgcaaag tggggtccca tcacgtttca gtggcagtgg atctgggaca    720
gatttcactc tcaccatcag cagtctgcaa cctgaagatt ttgctacgta ctactgtgct    780
cagggtttga ggcatcctaa gacgttcggc caagggacca aggtggaaat caaacgggcg    840
gccgcagaac aaaaactcat ctcagaagag gatctgaatt aa                       882
```

<210> SEQ ID NO 59
<211> LENGTH: 279
<212> TYPE: PRT
<213> ORGANISM: Artificial Sequence
<220> FEATURE:
<223> OTHER INFORMATION: Amino acid sequence identified using molecular biology techniques.

<400> SEQUENCE: 59

```
Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
                 20                  25                  30

Arg His Asp Phe Gly Phe Pro Gln Glu Glu Phe Gly Asn Gln Phe Gln
             35                  40                  45

Lys Ala Glu Thr Ile Pro Val Leu His Glu Met Ile Gln Gln Ile Phe
         50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Gln Trp Ile Gly Ser Gln Leu Ser Trp Tyr Gln
            195                 200                 205

Gln Lys Pro Gly Lys Ala Pro Lys Leu Leu Ile Met Trp Arg Ser Ser
        210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Leu Arg His Pro Lys Thr Phe Gly Gln Gly
            260                 265                 270

Thr Lys Val Glu Ile Lys Arg
            275
```

<210> SEQ ID NO 60
<211> LENGTH: 837

```
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 60
tgcgacttgc cacagacaca tagtttggga tcaagaagaa cattgatgtt attagcacaa        60
atgcgtagaa tttctttgtt ctcttgtcta aaggaccgtc acgacttcgg attccctcag       120
gaagagtttg gaaaccaatt ccaaaaagca gaaactattc ctgtcttgca cgaaatgatc       180
cagcaaatat tcaatttgtt ttctacaaag gactcatcag ccgcttggga tgaaactctg       240
ttagataaat tctacactga actatatcaa caactgaacg atctagaggc ttgcgttatt       300
cagggtgtag gagttactga aactccccta atgaaagaag attcaattct agccgttaga       360
aaatactttc agcgtatcac attgtattta aaggaaaaga atactcccc atgtgcatgg        420
gaggtggtta gagcagaaat tatgaggtcc ttctctcttt ctacgaattt gcaagaatct       480
ttgagatcta aggaaaccgt cgctgctcca tctgacatcc agatgaccca gtctccatcc       540
tccctgtctg catctgtagg agaccgtgtc accatcactt gccgggcaag tcagtggatt       600
gggtctcagt tatcttggta ccagcagaaa ccagggaaag cccctaagct cctgatcatg       660
tggcgttcct cgttgcaaag tggggtccca tcacgtttca gtggcagtgg atctgggaca       720
gatttcactc tcaccatcag cagtctgcaa cctgaagatt ttgctacgta ctactgtgct       780
cagggtttga ggcatcctaa gacgttcggc caagggacca aggtggaaat caaacgg        837
```

```
<210> SEQ ID NO 61
<211> LENGTH: 293
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 61

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175
```

Gln Ser Pro Ser Ser Leu Ser Ala Ser Val Gly Asp Arg Val Thr Ile
            180                 185                 190

Thr Cys Arg Ala Ser Arg Pro Ile Gly Thr Thr Leu Ser Trp Tyr Gln
        195                 200                 205

Gln Lys Pro Gly Lys Ala Pro Lys Leu Leu Ile Trp Phe Gly Ser Arg
210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg Ala Ala Ala Glu Gln Lys Leu Ile Ser
        275                 280                 285

Glu Glu Asp Leu Asn
    290

<210> SEQ ID NO 62
<211> LENGTH: 882
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 62
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aggaaaagaa atactccccc atgtgcatgg     420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcgtccgatt     600
gggacgacgt taagttggta ccagcagaaa ccagggaaag cccctaagct cctgatctgg     660
tttggttccc ggttgcaaag tggggtccca tcacgtttca gtggcagtgg atctgggaca     720
gatttcactc tcaccatcag cagtctgcaa cctgaagatt ttgctacgta ctactgtgcg     780
caggctggga cgcatcctac gacgttcggc caagggacca aggtggaaat caaacgggcg     840
gccgcagaac aaaaactcat ctcagaagag gatctgaatt aa                       882

<210> SEQ ID NO 63
<211> LENGTH: 279
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 63

Cys Asp Leu Pro Gln Thr His Ser Leu Gly Ser Arg Arg Thr Leu Met
1               5                   10                  15

```
Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Arg Pro Ile Gly Thr Thr Leu Ser Trp Tyr Gln
        195                 200                 205

Gln Lys Pro Gly Lys Ala Pro Lys Leu Leu Ile Trp Phe Gly Ser Arg
210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg
        275

<210> SEQ ID NO 64
<211> LENGTH: 837
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 64
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaagaag attcaattct agccgttaga     360
aaatactttc agcgtatcac attgtattta aaggaaaaga atactcccc atgtgcatgg     420 gaggtggtta gagcagaaat tatgaggtcc ttctctcttt ctacgaattt gcaagaatct     480
```

```
ttgagatcta aggaaaccgt cgctgctcca tctgacatcc agatgaccca gtctccatcc   540
tccctgtctg catctgtagg agaccgtgtc accatcactt gccgggcaag tcgtccgatt   600
gggacgacgt taagttggta ccagcagaaa ccagggaaag cccctaagct cctgatctgg   660
tttggttccc ggttgcaaag tggggtccca tcacgtttca gtggcagtgg atctgggaca   720
gatttcactc tcaccatcag cagtctgcaa cctgaagatt ttgctacgta ctactgtgcg   780
caggctggga cgcatcctac gacgttcggc caagggacca aggtggaaat caaacgg     837
```

<210> SEQ ID NO 65
<211> LENGTH: 293
<212> TYPE: PRT
<213> ORGANISM: Artificial Sequence
<220> FEATURE:
<223> OTHER INFORMATION: Amino acid sequence identified using molecular biology techniques.

<400> SEQUENCE: 65

```
Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Arg Pro Ile Gly Thr Met Leu Ser Trp Tyr Gln
        195                 200                 205

Gln Lys Pro Gly Lys Ala Pro Lys Leu Leu Ile Leu Ala Phe Ser Arg
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg Ala Ala Ala Glu Gln Lys Leu Ile Ser
        275                 280                 285

Glu Glu Asp Leu Asn
    290
```

<210> SEQ ID NO 66
<211> LENGTH: 882
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 66

```
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg aaaccaatt ccaaaaagca gaaactattc ctgtcttgca cgaaatgatc      180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aaggaaaaga aatactcccc atgtgcatgg     420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcgtccgatt     600
gggacgatgt taagttggta ccagcagaaa ccagggaaag cccctaagct cctgatcctt     660
gcttttttcc gtttgcaaag tggggtccca tcacgtttca gtggcagtgg atctgggaca     720
gatttcactc tcaccatcag cagtctgcaa cctgaagatt ttgctacgta ctactgcgcg     780
caggctggga cgcatcctac gacgttcggc caagggacca aggtggaaat caaacgggcg     840
gccgcagaac aaaaactcat ctcagaagag gatctgaatt aa                        882
```

<210> SEQ ID NO 67
<211> LENGTH: 279
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 67

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

-continued

```
Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
            165                 170                 175

Gln Ser Pro Ser Ser Leu Ser Ala Ser Val Gly Asp Arg Val Thr Ile
        180                 185                 190

Thr Cys Arg Ala Ser Arg Pro Ile Gly Thr Met Leu Ser Trp Tyr Gln
    195                 200                 205

Gln Lys Pro Gly Lys Ala Pro Lys Leu Leu Ile Leu Ala Phe Ser Arg
210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg
        275
```

<210> SEQ ID NO 68
<211> LENGTH: 837
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 68

```
tgcgacttgc cacagacaca tagtttggga tcaagaagaa cattgatgtt attagcacaa     60
atgcgtagaa tttctttgtt ctcttgtcta aaggaccgtc acgacttcgg attccctcag    120
gaagagtttg gaaaccaatt ccaaaaagca gaaactattc ctgtcttgca cgaaatgatc    180
cagcaaatat tcaatttgtt ttctacaaag gactcatcag ccgcttggga tgaaactctg    240
ttagataaat tctacactga actatatcaa caactgaacg atctagaggc ttgcgttatt    300
cagggtgtag gagttactga aactccccta atgaaagaag attcaattct agccgttaga    360
aaatactttc agcgtatcac attgtattta aaggaaaaga aatactcccc atgtgcatgg    420
gaggtggtta gagcagaaat tatgaggtcc ttctctcttt ctacgaattt gcaagaatct    480
ttgagatcta aggaaaccgt cgctgctcca tctgacatcc agatgaccca gtctccatcc    540
tccctgtctg catctgtagg agaccgtgtc accatcactt gccgggcaag tcgtccgatt    600
gggacgatgt taagttggta ccagcagaaa ccagggaaag cccctaagct cctgatcctt    660
gcttttccc gtttgcaaag tggggtccca tcacgtttca gtggcagtgg atctgggaca    720
gatttcactc tcaccatcag cagtctgcaa cctgaagatt ttgctacgta ctactgcgcg    780
caggctggga cgcatcctac gacgttcggc caagggacca aggtggaaat caaacgg      837
```

<210> SEQ ID NO 69
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 69

```
Asp Ile Gln Met Thr Gln Ser Pro Ser Ser Leu Ser Ala Ser Val Gly
```

```
            1               5              10              15
        Asp Arg Val Thr Ile Thr Cys Arg Ala Ser Gln Trp Ile Gly Ser Gln
                        20                  25                  30

Leu Ser Trp Tyr Gln Gln Lys Pro Gly Lys Ala Pro Lys Leu Leu Ile
                        35                  40                  45

Met Trp Arg Ser Ser Leu Gln Ser Gly Val Pro Ser Arg Phe Ser Gly
                    50                  55                  60

Ser Gly Ser Gly Thr Asp Phe Thr Leu Thr Ile Ser Ser Leu Gln Pro
         65                 70                  75                  80

Glu Asp Phe Ala Thr Tyr Tyr Cys Ala Gln Gly Leu Arg His Pro Lys
                        85                  90                  95

Thr Phe Gly Gln Gly Thr Lys Val Glu Ile Lys Cys
                        100                 105

<210> SEQ ID NO 70
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 70
gacatccaga tgacccagtc tccatcctcc ctgtctgcat ctgtaggaga ccgtgtcacc     60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggc atcctaagac gttcggccaa    300
gggaccaagg tggaaatcaa atgc                                           324

<210> SEQ ID NO 71
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 71

Glu Val Gln Leu Leu Glu Ser Gly Gly Gly Leu Val Gln Pro Gly Gly
         1               5                  10                  15

Ser Leu Arg Leu Ser Cys Thr Ala Ser Gly Phe Thr Phe Arg His Tyr
                        20                  25                  30

Arg Met Gly Trp Val Arg Gln Ala Pro Gly Lys Gly Leu Glu Trp Val
                        35                  40                  45

Ser Trp Ile Arg Pro Asp Gly Thr Phe Thr Tyr Tyr Ala Asp Ser Val
                    50                  55                  60

Lys Gly Arg Phe Thr Ile Ser Arg Asp Asn Ser Lys Asn Thr Leu Tyr
         65                 70                  75                  80

Leu Gln Met Asn Ser Leu Arg Ala Glu Asp Thr Ala Val Tyr Tyr Cys
                        85                  90                  95

Ala Lys Ser Tyr Met Gly Asp Arg Phe Asp Tyr Trp Gly Gln Gly Thr
                        100                 105                 110

Leu Val Thr Val Ser Ser
                    115
```

<210> SEQ ID NO 72
<211> LENGTH: 355
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 72

```
gaggtgcagc tgttggagtc tgggggaggc ttggtacagc ctgggggtc cctgcgtctc      60
tcctgtacag cctccggatt cacctttagg cattatcgta tgggttgggt ccgccaggct    120
ccagggaagg gtctagagtg gtctcatgg attcgtccgg atggtacgtt tacatactac     180
gcagactccg tgaagggccg gttcaccatc tcccgcgaca attccaagaa cacgctgtat    240
ctgcaaatga acagcctgcg tgccgaggac accgcggtat attactgtgc gaaatcttat    300
atgggtgata ggtttgacta ctggggtcag ggaaccctgg tcaccgtctc gagcg         355
```

<210> SEQ ID NO 73
<211> LENGTH: 118
<212> TYPE: PRT
<213> ORGANISM: Artificial Sequence
<220> FEATURE:
<223> OTHER INFORMATION: Amino acid sequence identified using molecular biology techniques.

<400> SEQUENCE: 73

```
Glu Val Gln Leu Leu Glu Ser Gly Gly Gly Leu Val Gln Pro Gly Gly
 1               5                  10                  15
Ser Leu Arg Leu Ser Cys Thr Ala Ser Gly Phe Thr Phe Arg His Tyr
            20                  25                  30
Arg Met Gly Trp Val Arg Gln Ala Pro Gly Lys Gly Leu Glu Trp Val
        35                  40                  45
Ser Trp Ile Arg Pro Asp Gly Thr Phe Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Ser Tyr Met Gly Asp Arg Phe Asp Tyr Trp Gly Gln Gly Thr
            100                 105                 110
Leu Val Thr Val Ser Ser
        115
```

<210> SEQ ID NO 74
<211> LENGTH: 354
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 74

```
gaggtgcagc tgttggagtc tgggggaggc ttggtacagc ctgggggtc cctgcgtctc      60
tcctgtacag cctccggatt cacctttagg cattatcgta tgggttgggt ccgccaggct    120
ccagggaagg gtctagagtg gtctcatgg attcgtccgg atggtacgtt tacatactac     180
gcagactccg tgaagggccg gttcaccatc tcccgcgaca attccaagaa cacgctgtat    240
ctgcaaatga acagcctgcg tgccgaggac accgcggtat attactgtgc gaaatcttat    300
atggctgata ggtttgacta ctggggtcag ggaaccctgg tcaccgtctc gagc          354
```

<210> SEQ ID NO 75
<211> LENGTH: 119
<212> TYPE: PRT
<213> ORGANISM: Artificial Sequence
<220> FEATURE:
<223> OTHER INFORMATION: Amino acid sequence identified using molecular biology techniques.

<400> SEQUENCE: 75

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Asn Ala
            20                  25                  30

Thr Met Ser Trp Val Arg Gln Ala Pro Gly Lys Gly Leu Glu Trp Val
        35                  40                  45

Ser Asp Ile Asp Gln Val Gly His Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ser Trp His Pro Asp Leu Phe Asp Tyr Trp Gly Gln Gly
            100                 105                 110

Thr Leu Val Thr Val Ser Ser
        115

<210> SEQ ID NO 76
<211> LENGTH: 351
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 76
gaggtgcagc tgttggagtc tgggggaggc ttggtacagc ctgggggtc cctgcgtctc      60
tcctgtgcag cctccggatt cacctttggg aattatagga tgacttgggt ccgccaggct    120
ccagggaagg gtctagagtg ggtctcaact atttctcctt tgggtacgta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagggcgt    300
tggtcgattt ttgactactg gggtcaggga accctggtca ccgtctcgag c             351

<210> SEQ ID NO 77
<211> LENGTH: 119
<212> TYPE: PRT
<213> ORGANISM: Artificial Sequence
<220> FEATURE:
<223> OTHER INFORMATION: Amino acid sequence identified using molecular biology techniques.

<400> SEQUENCE: 77

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Pro Ser Thr His Gly Lys Phe Asp Tyr Trp Gly Gln Gly
            100                 105                 110

Thr Leu Val Thr Val Ser Ser
            115

<210> SEQ ID NO 78
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 78
gaggtgcagc tgttggagtc tgggggaggc ttggtacagc ctggggggtc cctgcgtctc      60
tcctgtgcag cctccggatt cacctttgat acgagtagta tgttgtgggt ccgccaggct     120
ccagggaagg gtctagagtg ggtctcagtt attcatcaga gtggtacgcc tacatactac     180
gcagactccg tgaagggccg gttcaccatc tcccgcgaca attccaagaa cacgctgtat     240
ctgcaaatga acagcctgcg tgccgaggac accgcggtat attactgtgc gaaatttccg     300
tctactcatg gtaagtttga ctactggggt cagggaaccc tggtcaccgt ctcgagc        357

<210> SEQ ID NO 79
<211> LENGTH: 197
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 79

Glu Gly Lys Val Ser Ser Ala Lys Gln Arg Leu Lys Cys Ala Ser Leu
 1               5                  10                  15

Gln Lys Phe Gly Glu Arg Ala Phe Lys Ala Trp Ala Val Ala Arg Leu
            20                  25                  30

Ser Gln Arg Phe Pro Lys Ala Glu Phe Ala Glu Val Ser Lys Leu Val
        35                  40                  45

Thr Asp Leu Thr Lys Val His Thr Glu Cys Cys His Gly Asp Leu Leu
 50                  55                  60

Glu Cys Ala Asp Asp Arg Ala Asp Leu Ala Lys Tyr Ile Cys Glu Asn
 65                  70                  75                  80

Gln Asp Ser Ile Ser Ser Lys Leu Lys Glu Cys Cys Glu Lys Pro Leu
                 85                  90                  95

Leu Glu Lys Ser His Cys Ile Ala Glu Val Glu Asn Asp Glu Met Pro
            100                 105                 110

Ala Asp Leu Pro Ser Leu Ala Ala Asp Phe Val Glu Ser Lys Asp Val
        115                 120                 125

Cys Lys Asn Tyr Ala Glu Ala Lys Asp Val Phe Leu Gly Met Phe Leu
    130                 135                 140

Tyr Glu Tyr Ala Arg Arg His Pro Asp Tyr Ser Val Val Leu Leu Leu
145                 150                 155                 160

Arg Leu Ala Lys Thr Tyr Glu Thr Thr Leu Glu Lys Cys Cys Ala Ala
                165                 170                 175

Ala Asp Pro His Glu Cys Tyr Ala Lys Val Phe Asp Glu Phe Lys Pro
            180                 185                 190

Leu Val Glu Glu Pro
        195

<210> SEQ ID NO 80
<211> LENGTH: 591
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 80
gaagggaagg tttcgtctgc caaacagaga ctcaagtgtg ccagtctcca aaaatttgga      60
gaaagagctt tcaaagcatg ggcagtagct cgcctgagcc agagatttcc caaagctgag    120
tttgcagaag tttccaagtt agtgacagat cttaccaaag tccacacgga atgctgccat    180
ggagatctgc ttgaatgtgc tgatgacagg gcggaccttg ccaagtatat ctgtgaaaat    240
caagattcga tctccagtaa actgaaggaa tgctgtgaaa acctctgtt ggaaaaatcc     300 cactgcattg ccgaagtgga aaatgatgag atgcctgctg acttgccttc attagctgct    360
gattttgttg aaagtaagga tgtttgcaaa actatgctag gcaaagga tgtcttcctg      420 ggcatgtttt tgtatgaata tgcaagaagg catcctgatt actctgtcgt gctgctgctg    480
agacttgcca agacatatga aaccactcta gagaagtgct gtgccgctgc agatcctcat    540
gaatgctatg ccaaagtgtt cgatgaattt aaacctcttg tggaagagcc t             591

<210> SEQ ID NO 81
<211> LENGTH: 585
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 81

Asp Ala His Lys Ser Glu Val Ala His Arg Phe Lys Asp Leu Gly Glu
1                5                  10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg

```
            145                 150                 155                 160
Tyr Lys Ala Ala Phe Thr Glu Cys Cys Gln Ala Ala Asp Lys Ala Ala
                    165                 170                 175

Cys Leu Leu Pro Lys Leu Asp Glu Leu Arg Asp Glu Gly Lys Val Ser
                    180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575
```

Ala Ala Ser Gln Ala Ala Leu Gly Leu
          580                 585

<210> SEQ ID NO 82
<211> LENGTH: 1755
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 82

| | | | | | | |
|---|---|---|---|---|---|---|
| gatgcacaca | agagtgaggt | tgctcatcgg | tttaaagatt | tgggagaaga | aaatttcaaa | 60 |
| gccttggtgt | tgattgcctt | tgctcagtat | cttcagcagt | gtccatttga | agatcatgta | 120 |
| aaattagtga | atgaagtaac | tgaatttgca | aaaacatgtg | ttgctgatga | gtcagctgaa | 180 |
| aattgtgaca | aatcacttca | tacccttttt | ggagacaaat | tatgcacagt | tgcaactctt | 240 |
| cgtgaaacct | atggtgaaat | ggctgactgc | tgtgcaaaac | aagaacctga | gagaaatgaa | 300 |
| tgcttcttgc | aacacaaaga | tgacaaccca | aacctccccc | gattggtgag | accagaggtt | 360 |
| gatgtgatgt | gcactgcttt | tcatgacaat | gaagagacat | ttttgaaaaa | atacttatat | 420 |
| gaaattgcca | agacatcc | ttactttat | gccccggaac | tccttttctt | tgctaaaagg | 480 |
| tataaagctg | cttttacaga | atgttgccaa | gctgctgata | agctgcctg | cctgttgcca | 540 |
| aagctcgatg | aacttcggga | tgaagggaag | gtttcgtctg | ccaaacagag | actcaagtgt | 600 |
| gccagtctcc | aaaaatttgg | agaaagagct | ttcaaagcat | gggcagtagc | tcgcctgagc | 660 |
| cagagatttc | ccaaagctga | gtttgcagaa | gtttccaagt | tagtgacaga | tcttaccaaa | 720 |
| gtccacacgg | aatgctgcca | tggagatctg | cttgaatgtg | ctgatgacag | ggcggacctt | 780 |
| gccaagtata | tctgtgaaaa | tcaagattcg | atctccagta | aactgaagga | atgctgtgaa | 840 |
| aaacctctgt | tggaaaaatc | ccactgcatt | gccgaagtgg | aaaatgatga | gatgcctgct | 900 |
| gacttgcctt | cattagctgc | tgattttgtt | gaaagtaagg | atgtttgcaa | aaactatgct | 960 |
| gaggcaaagg | atgtcttcct | gggcatgttt | ttgtatgaat | atgcaagaag | gcatcctgat | 1020 |
| tactctgtcg | tgctgctgct | gagacttgcc | aagacatatg | aaaccactct | agagaagtgc | 1080 |
| tgtgccgctg | cagatcctca | tgaatgctat | gccaaagtgt | tcgatgaatt | taaacctctt | 1140 |
| gtggaagagc | tcagaatttt | aatcaaacaa | aattgtgagc | ttttgagca | gcttggagag | 1200 |
| tacaaattcc | agaatgcgct | attagttcgt | tacaccaaga | agtaccccca | agtgtcaact | 1260 |
| ccaactcttg | tagaggtctc | aagaaaccta | ggaaagtgg | gcagcaaatg | ttgtaaacat | 1320 |
| cctgaagcaa | aaagaatgcc | ctgtgcagaa | gactatctat | ccgtggtcct | gaaccagtta | 1380 |
| tgtgtgttgc | atgagaaaac | gccagtaagt | gacagagtca | ccaaatgctg | cacagaatcc | 1440 |
| ttggtgaaca | ggcgaccatg | cttttcagct | ctggaagtcg | atgaaacata | cgttcccaaa | 1500 |
| gagtttaatg | ctgaaacatt | caccttccat | gcagatatat | gcacactttc | tgagaaggag | 1560 |
| agacaaatca | agaaacaaac | tgcacttgtt | gagcttgtga | acacaagcc | caaggcaaca | 1620 |
| aaagagcaac | tgaaagctgt | tatggatgat | ttcgcagctt | ttgtagagaa | gtgctgcaag | 1680 |
| gctgacgata | aggagacctg | ctttgccgag | gagggtaaaa | aacttgttgc | tgcaagtcaa | 1740 |
| gctgccttag | gctta | | | | | 1755 |

<210> SEQ ID NO 83
<211> LENGTH: 108
<212> TYPE: PRT

<213> ORGANISM: Artificial Sequence
<220> FEATURE:
<223> OTHER INFORMATION: Amino acid sequence identified using molecular
      biology techniques.

<400> SEQUENCE: 83

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Gln
             20                  25                  30

Leu Ser Trp Tyr Gln Gln Lys Pro Gly Lys Ala Pro Lys Leu Leu Ile
         35                  40                  45

Met Trp Arg Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Arg
            100                 105
```

<210> SEQ ID NO 84
<211> LENGTH: 330
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 84

```
tcgacggaca tccagatgac ccagtctcca tcctccctgt ctgcatctgt aggagaccgt    60
gtcaccatca cttgccgggc aagtcagtgg attgggtctc agttatcttg gtaccagcag   120
aaaccaggga agcccctaa gctcctgatc atgtggcgtt cctcgttgca aagtggggtc    180
ccatcacgtt tcagtggcag tggatctggg acagatttca ctctcaccat cagcagtctg   240
caacctgaag attttgctac gtactactgt gctcagggtt gaggcatcc taagacgttc    300 ggccaaggga ccaaggtgga aatcaaacgg                                    330
```

<210> SEQ ID NO 85
<211> LENGTH: 56
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 85

```
taacaagaat aatgggatcc accggcgatg cacacaagag tgaggttgct catcgg       56
```

<210> SEQ ID NO 86
<211> LENGTH: 88
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 86

```
gcgcgcgcgc gcttcaagct ttcattaatg gtgatggtga tgatgtaagc ctaaggcagc    60
ttgacttgca gcaacaagtt ttttaccc                                       88
```

```
<210> SEQ ID NO 87
<211> LENGTH: 35
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 87
gagccagaga tttcccgccg ctgagtttgc agaag                              35

<210> SEQ ID NO 88
<211> LENGTH: 35
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 88
cttctgcaaa ctcagcggcg ggaaatctct ggctc                              35

<210> SEQ ID NO 89
<211> LENGTH: 37
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 89
gagatttccc aaagctgcct ttgcagaagt ttccaag                            37

<210> SEQ ID NO 90
<211> LENGTH: 37
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 90
cttggaaact tctgcaaagg cagctttggg aaatctc                            37

<210> SEQ ID NO 91
<211> LENGTH: 37
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 91
ccaaagctga gtttgcagcc gttccaagt tagtgac                             37

<210> SEQ ID NO 92
<211> LENGTH: 37
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 92
gtcactaact tggaaacggc tgcaaactca gctttgg                            37
```

```
<210> SEQ ID NO 93
<211> LENGTH: 37
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 93
gattttgttg aaagtaaggc cgtttgcaaa aactatg                                  37

<210> SEQ ID NO 94
<211> LENGTH: 37
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 94
catagttttt gcaaacggcc ttactttcaa caaaatc                                  37

<210> SEQ ID NO 95
<211> LENGTH: 40
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 95
gaaagtaagg atgtttgcgc caactatgct gaggcaaagg                               40

<210> SEQ ID NO 96
<211> LENGTH: 40
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 96
cctttgcctc agcatagttg gcgcaaacat ccttactttc                               40

<210> SEQ ID NO 97
<211> LENGTH: 36
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 97
gctgaggcaa aggatgcctt cctgggcatg tttttg                                   36

<210> SEQ ID NO 98
<211> LENGTH: 36
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 98
caaaaacatg cccaggaagg catcctttgc ctcagc                                   36

<210> SEQ ID NO 99
```

```
<211> LENGTH: 35
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 99
ggatgtcttc ctgggcgcct ttttgtatga atatg                           35

<210> SEQ ID NO 100
<211> LENGTH: 35
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 100
catattcata caaaaaggcg cccaggaaga catcc                           35

<210> SEQ ID NO 101
<211> LENGTH: 41
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 101
gctgctgctg agacttgccg ccacatatga aaccactcta g                    41

<210> SEQ ID NO 102
<211> LENGTH: 41
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 102
ctagagtggt ttcatatgtg gcggcaagtc tcagcagcag c                    41

<210> SEQ ID NO 103
<211> LENGTH: 591
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 103
```

Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

-continued

```
Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Val Ser
                180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
```

```
            515                 520                 525
Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His His His His His His
        580                 585                 590

<210> SEQ ID NO 104
<211> LENGTH: 591
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 104

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Val Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Ala Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285
```

```
Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His His His His His
                580                 585                 590

<210> SEQ ID NO 105
<211> LENGTH: 591
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 105

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60
```

```
Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Val Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Ala Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480
```

```
Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His His His His His His
            580                 585                 590

<210> SEQ ID NO 106
<211> LENGTH: 591
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 106

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Val Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Ala Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His His His His His His
            580                 585                 590

<210> SEQ ID NO 107
<211> LENGTH: 591
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 107

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
```

-continued

```
                20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
            115                 120                 125
Asp Asn Glu Glu Thr Phe Leu Lys Lys Tyr Leu Tyr Glu Ile Ala Arg
            130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Val Ser
            180                 185                 190
Ser Ala Lys Gln Arg Leu Lys Cys Ala Ser Leu Gln Lys Phe Gly Glu
            195                 200                 205
Arg Ala Phe Lys Ala Trp Ala Val Ala Arg Leu Ser Gln Arg Phe Pro
            210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
 290                 295                 300
Leu Ala Ala Asp Phe Val Glu Ser Lys Ala Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
            370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
```

```
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His His His His His His
                580                 585                 590

<210> SEQ ID NO 108
<211> LENGTH: 591
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 108

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Val Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
```

210                 215                 220
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Ala Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
530                 535                 540

Lys Ala Val Met Asp Asp Phe Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His His His His His
                580                 585                 590

<210> SEQ ID NO 109
<211> LENGTH: 591
<212> TYPE: PRT
<213> ORGANISM: Artificial Sequence
<220> FEATURE:
<223> OTHER INFORMATION: Amino acid sequence identified using molecular
    biology techniques.

<400> SEQUENCE: 109

```
Asp Ala His Lys Ser Glu Val Ala His Arg Phe Lys Asp Leu Gly Glu
  1               5                  10                  15

Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
             85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Val Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Ala Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
```

```
                    405                 410                 415
Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His His His His His His
            580                 585                 590
```

<210> SEQ ID NO 110
<211> LENGTH: 591
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 110

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175
```

-continued

```
Cys Leu Leu Pro Lys Leu Asp Glu Leu Arg Asp Glu Gly Lys Val Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Ala Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu His His His His His His
            580                 585                 590
```

-continued

<210> SEQ ID NO 111
<211> LENGTH: 591
<212> TYPE: PRT
<213> ORGANISM: Artificial Sequence
<220> FEATURE:
<223> OTHER INFORMATION: Amino acid sequence identified using molecular biology techniques.

<400> SEQUENCE: 111

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Val Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Ala Thr
            340                 345                 350

Tyr Glu Thr Thr Leu Glu Lys Cys Cys Ala Ala Ala Asp Pro His Glu
        355                 360                 365

```
Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His His His His His His
            580                 585                 590

<210> SEQ ID NO 112
<211> LENGTH: 1774
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 112
gatgcacaca agagtgaggt tgctcatcgg tttaaagatt tgggagaaga aaatttcaaa      60
gccttggtgt tgattgcctt tgctcagtat cttcagcagt gtccatttga agatcatgta    120
aaattagtga atgaagtaac tgaatttgca aaaacatgtg ttgctgatga gtcagctgaa    180
aattgtgaca aatcacttca taccttttt ggagacaaat tatgcacagt tgcaactctt    240
cgtgaaacct atggtgaaat ggctgactgc tgtgcaaaac aagaacctga gaaaatgaa    300 tgcttcttgc aacacaaaga tgacaaccca acctcccccc gattggtgag accagaggtt    360
gatgtgatgt gcactgcttt tcatgacaat gaagagacat ttttgaaaaa atacttatat    420
gaaattgcca aagacatcc ttactttat gccccggaac tccttttctt tgctaaaagg    480
tataaagctg cttttacaga atgttgccaa gctgctgata agctgcctg cctgttgcca    540 aagctcgatg aacttcggga tgaagggaag gtttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag ggcggacctt    780
```

```
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga agtacccca agtgtcaact   1260 ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca gcgaccatg cttttcagct ctggaagtcg atgaaacata cgttcccaaa   1500
gagtttaatg ctgaaacatt caccttccat gcagatatat gcacactttc tgagaaggag   1560
agacaaatca gaaacaaac tgcacttgtt gagcttgtga acacaagcc aaggcaaca    1620 aaagagcaac tgaaagctgt tatggatgat ttcgcagctt ttgtagagaa gtgctgcaag   1680
gctgacgata aggagacctg ctttgccgag agggtaaaa aacttgttgc tgcaagtcaa    1740
gctgccttag gcttacatca tcaccatcac catt                               1774

<210> SEQ ID NO 113
<211> LENGTH: 1774
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 113
gatgcacaca agagtgaggt tgctcatcgg tttaaagatt tgggagaaga aaatttcaaa     60
gccttggtgt tgattgcctt tgctcagtat cttcagcagt gtccatttga agatcatgta    120
aaattagtga atgaagtaac tgaatttgca aaaacatgtg ttgctgatga gtcagctgaa    180
aattgtgaca aatcacttca tacccttttt ggagacaaat tatgcacagt tgcaactctt    240
cgtgaaacct atggtgaaat ggctgactgc tgtgcaaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca gagacatcc ttactttat gccccggaac tccttttctt tgctaaaagg    480
tataagctgc tttttacaga atgttgccaa gctgctgata agctgcctg cctgttgcca    540 aagctcgatg aacttcggga tgaagggaag gtttcgtctg ccaaacagag actcaagtgt    600
gccagtctcc aaaaatttgg agaaagagct ttcaaagcat gggcagtagc tcgcctgagc    660
cagagatttc ccgccgctga gtttgcagaa gtttccaagt tagtgacaga tcttaccaaa    720
gtccacacgg aatgctgcca tggagatctg cttgaatgtg ctgatgacag gcggaccttt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
```

```
tactctgtcg tgctgctgct gagacttgcc aagacatatg aaaccactct agagaagtgc      1080
tgtgccgctg cagatcctca tgaatgctat gccaaagtgt tcgatgaatt taaacctctt      1140
gtggaagagc ctcagaattt aatcaaacaa aattgtgagc tttttgagca gcttggagag      1200
tacaaattcc agaatgcgct attagttcgt tacaccaaga agtacccca agtgtcaact       1260 ccaactcttg tagaggtctc aagaaaccta ggaaaagtgg gcagcaaatg ttgtaaacat      1320
cctgaagcaa aaagaatgcc ctgtgcagaa gactatctat ccgtggtcct gaaccagtta      1380
tgtgtgttgc atgagaaaac gccagtaagt gacagagtca ccaaatgctg cacagaatcc      1440
ttggtgaaca ggcgaccatg cttttcagct ctggaagtcg atgaaacata cgttcccaaa      1500
gagtttaatg ctgaaacatt caccttccat gcagatatat gcacactttc tgagaaggag      1560
agacaaatca gaaacaaac tgcacttgtt gagcttgtga acacaagcc caaggcaaca       1620 aaagagcaac tgaaagctgt tatggatgat ttcgcagctt ttgtagagaa gtgctgcaag      1680
gctgacgata aggagacctg ctttgccgag gagggtaaaa aacttgttgc tgcaagtcaa      1740
gctgccttag gcttacatca tcaccatcac catt                                  1774

<210> SEQ ID NO 114
<211> LENGTH: 1774
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 114
gatgcacaca agagtgaggt tgctcatcgg tttaaagatt tgggagaaga aaatttcaaa        60
gccttggtgt tgattgcctt tgctcagtat cttcagcagt gtccatttga agatcatgta      120
aaattagtga atgaagtaac tgaatttgca aaaacatgtg ttgctgatga gtcagctgaa      180
aattgtgaca aatcacttca tacccttttt ggagacaaat tatgcacagt tgcaactctt      240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca aagacatcc ttactttat gccccggaac tccttttctt tgctaaaagg       480
tataaagctg cttttacaga atgttgccaa gctgctgata agctgcctg cctgttgcca       540 aagctcgatg aacttcggga tgaagggaag gtttcgtctg ccaaacagag actcaagtgt      600
gccagtctcc aaaaatttgg agaaagagct ttcaaagcat gggcagtagc tcgcctgagc      660
cagagatttc ccaaagctgc ctttgcagaa gtttccaagt tagtgacaga tcttaccaaa      720
gtccacacgg aatgctgcca tggagatctg cttgaatgtg ctgatgacag ggcggacctt      780
gccaagtata tctgtgaaaa tcaagattcg atctccagta aactgaagga atgctgtgaa      840
aaacctctgt tggaaaaatc ccactgcatt gccgaagtgg aaaatgatga atgcctgct       900 gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctg cagatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga agtacccca agtgtcaact      1260
```

| ccaactcttg tagaggtctc aagaaaccta ggaaaagtgg gcagcaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg atgaaacata cgttcccaaa | 1500 |
| gagtttaatg ctgaaacatt caccttccat gcagatatat gcacactttc tgagaaggag | 1560 |
| agacaaatca agaacaaac tgcacttgtt gagcttgtga acacaagcc aaggcaaca | 1620 |
| aaagagcaac tgaaagctgt tatggatgat ttcgcagctt ttgtagagaa gtgctgcaag | 1680 |
| gctgacgata aggagacctg ctttgccgag gagggtaaaa aacttgttgc tgcaagtcaa | 1740 |
| gctgccttag gcttacatca tcaccatcac catt | 1774 |

<210> SEQ ID NO 115
<211> LENGTH: 1774
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 115

| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtcagctgaa | 180 |
| aattgtgaca aatcacttca tacccttttt ggagacaaat tatgcacagt tgcaactctt | 240 |
| cgtgaaacct atggtgaaat ggctgactgc tgtgcaaaac aagaacctga gagaaatgaa | 300 |
| tgcttcttgc aacacaaaga tgacaaccca aacctccccc gattggtgag accagaggtt | 360 |
| gatgtgatgt gcactgcttt tcatgacaat gaagagacat ttttgaaaaa atacttatat | 420 |
| gaaattgcca agacatatcc ttactttat gccccggaac tccttttctt tgctaaaagg | 480 |
| tataaagctg cttttacaga atgttgccaa gctgctgata agctgcctg cctgttgcca | 540 |
| aagctcgatg aacttcggga tgaagggaag gtttcgtctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagcc gtttccaagt tagtgacaga tcttaccaaa | 720 |
| gtccacacgg aatgctgcca tggagatctg cttgaatgtg ctgatgacag gcggaccctt | 780 |
| gccaagtata tctgtgaaaa tcaagattcg atctccagta aactgaagga atgctgtgaa | 840 |
| aaacctctgt ggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctg cagatcctca tgaatgctat gccaagtgt tcgatgaatt taaacctctt | 1140 |
| gtggaagagc tcagaatttt aatcaaacaa aattgtgagc ttttttgagca gcttggagag | 1200 |
| tacaaattcc agaatgcgct attagttcgt tacaccaaga agtaccccca agtgtcaact | 1260 |
| ccaactcttg tagaggtctc aagaaaccta ggaaaagtgg gcagcaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg atgaaacata cgttcccaaa | 1500 |

```
gagtttaatg ctgaaacatt caccttccat gcagatatat gcacactttc tgagaaggag   1560
agacaaatca agaaacaaac tgcacttgtt gagcttgtga acacaagcc caaggcaaca    1620 aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttacatca tcaccatcac catt                               1774
```

<210> SEQ ID NO 116
<211> LENGTH: 1774
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 116

```
gatgcacaca agagtgaggt tgctcatcgg tttaaagatt tgggagaaga aaatttcaaa     60
gccttggtgt tgattgcctt tgctcagtat cttcagcagt gtccatttga agatcatgta   120
aaattagtga atgaagtaac tgaatttgca aaaacatgtg ttgctgatga gtcagctgaa   180
aattgtgaca aatcacttca taccctttttt ggagacaaat tatgcacagt tgcaactctt   240
cgtgaaacct atggtgaaat ggctgactgc tgtgcaaaac aagaacctga gagaaatgaa   300
tgcttcttgc aacacaaaga tgacaaccca aacctccccc gattggtgag accagaggtt   360
gatgtgatgt gcactgcttt tcatgacaat gaagagacat ttttgaaaaa atacttatat   420
gaaattgcca agacatcc ttacttttat gccccggaac tccttttctt tgctaaaagg     480
tataaagctg cttttacaga atgttgccaa gctgctgata aagctgcctg cctgttgcca   540
aagctcgatg aacttcggga tgaagggaag gttttcgtctg ccaaacagag actcaagtgt   600
gccagtctcc aaaaatttgg agaaagagct ttcaaagcat gggcagtagc tcgcctgagc   660
cagagatttc ccaaagctga gtttgcagaa gtttccaagt tagtgacaga tcttaccaaa   720
gtccacacgg aatgctgcca tggagatctg cttgaatgtg ctgatgacag ggcggacctt   780
gccaagtata tctgtgaaaa tcaagattcg atctccagta aactgaagga atgctgtgaa   840
aaacctctgt ggaaaaatc ccactgcatt gccgaagtgg aaaatgatga gatgcctgct    900
gacttgcctt cattagctgc tgattttgtt gaaagtaagg ccgtttgcaa aaactatgct   960
gaggcaaagg atgtcttcct gggcatgttt ttgtatgaat atgcaagaag gcatcctgat  1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt  1140
gtggaagagc tcagaatttt aatcaaacaa aattgtgagc ttttttgagca gcttggagag   1200 tacaaattcc agaatgcgct attagttcgt tacaccaaga agtaccccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg ctttttcagct ctgaagtcg atgaaacata cgttcccaaa   1500
gagtttaatg ctgaaacatt caccttccat gcagatatat gcacactttc tgagaaggag   1560
agacaaatca agaaacaaac tgcacttgtt gagcttgtga acacaagcc caaggcaaca    1620 aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
```

```
gctgccttag gcttacatca tcaccatcac catt                              1774
```

<210> SEQ ID NO 117
<211> LENGTH: 1774
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 117

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta    120
aaattagtga atgaagtaac tgaatttgca aaaacatgtg ttgctgatga gtcagctgaa    180
aattgtgaca aatcacttca taccctttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca aagacatcc ttacttttat gccccggaac tccttttctt tgctaaaagg    480
tataaagctg cttttacaga atgttgccaa gctgctgata agctgcctg cctgttgcca    540
aagctcgatg aacttcggga tgaagggaag gtttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag gcggaccctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcgc caactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc ttttttgagca gcttggagag   1200
tacaaattcc agaatgcgct attagttcgt tacaccaaga agtaccccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg ctttttcagct ctggaagtcg atgaaacata cgttcccaaa   1500
gagtttaatg ctgaaacatt caccttccat gcagatatat gcacactttc tgagaaggag   1560
agacaaatca gaaacaaac tgcacttgtt gagcttgtga acacaagcc caaggcaaca   1620
aaagagcaac tgaaagctgt tatggatgat ttcgcagctt ttgtagagaa gtgctgcaag   1680
gctgacgata aggagacctg cttttgccgag gagggtaaaa aacttgttgc tgcaagtcaa   1740
gctgccttag gcttacatca tcaccatcac catt                               1774
```

<210> SEQ ID NO 118
<211> LENGTH: 1774
<212> TYPE: DNA
<213> ORGANISM: Artificial Sequence
<220> FEATURE:

<223> OTHER INFORMATION: Nucleic acid sequence identified using
    molecular biology techniques.

<400> SEQUENCE: 118

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca aatcacttca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttactttat gccccggaac tccttttctt tgctaaaagg     480
tataaagctg cttttacaga atgttgccaa gctgctgata aagctgcctg cctgttgcca     540
aagctcgatg aacttcggga tgaagggaag gtttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag ggcggacctt     780
gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgtttgcaa aaactatgct     960
gaggcaaagg atgccttcct gggcatgttt ttgtatgaat atgcaagaag gcatcctgat    1020
tactctgtcg tgctgctgct gagacttgcc aagacatatg aaaccactct agagaagtgc    1080
tgtgccgctg cagatcctca tgaatgctat gccaaagtgt tcgatgaatt taaacctctt    1140
gtggaagagc ctcagaattt aatcaaacaa aattgtgagc tttttgagca gcttggagag    1200
tacaaattcc agaatgcgct attagttcgt tacaccaaga agtaccccca agtgtcaact    1260
ccaactcttg tagaggtctc aagaaaccta ggaaaagtgg gcagcaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca gaaacaaac tgcacttgtt gagcttgtga acacaagcc caaggcaaca    1620
aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gcttacatca tcaccatcac catt                                1774
```

<210> SEQ ID NO 119
<211> LENGTH: 1774
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 119

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
```

```
aaattagtga atgaagtaac tgaatttgca aaaacatgtg ttgctgatga gtcagctgaa      180
aattgtgaca aatcacttca tacccttttt ggagacaaat tatgcacagt tgcaactctt      240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca aagacatcc ttactttat gccccggaac tccttttctt tgctaaaagg       480
tataaagctg cttttacaga atgttgccaa gctgctgata agctgcctg cctgttgcca       540 aagctcgatg aacttcggga tgaagggaag gtttcgtctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg cttgaatgtg ctgatgacag ggcggacctt      780
gccaagtata tctgtgaaaa tcaagattcg atctccagta aactgaagga atgctgtgaa      840
aaacctctgt tggaaaaatc ccactgcatt gccgaagtgg aaaatgatga gatgcctgct      900
gacttgcctt cattagctgc tgattttgtt gaaagtaagg atgtttgcaa aaactatgct      960
gaggcaaagg atgtcttcct gggcgccttt ttgtatgaat atgcaagaag gcatcctgat     1020
tactctgtcg tgctgctgct gagacttgcc aagacatatg aaaccactct agagaagtgc     1080
tgtgccgctg cagatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga aagtacccca agtgtcaact     1260
ccaactcttg tagaggtctc aagaaaccta ggaaaagtgg gcagcaaatg ttgtaaacat     1320
cctgaagcaa aagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca ggcgaccatg cttttcagct ctggaagtcg atgaaacata cgttcccaaa     1500
gagtttaatg ctgaaacatt caccttccat gcagatatat gcacactttc tgagaaggag     1560
agacaaatca agaaacaaac tgcacttgtt gagcttgtga acacaagcc caaggcaaca     1620 aaagagcaac tgaaagctgt tatggatgat ttcgcagctt ttgtagagaa gtgctgcaag     1680
gctgacgata aggagcctg ctttgccgag gagggtaaaa aacttgttgc tgcaagtcaa     1740
gctgccttag gcttacatca tcaccatcac catt                                  1774
```

<210> SEQ ID NO 120
<211> LENGTH: 1774
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 120

```
gatgcacaca agagtgaggt tgctcatcgg tttaaagatt tgggagaaga aaatttcaaa       60
gccttggtgt tgattgcctt tgctcagtat cttcagcagt gtccatttga agatcatgta      120
aaattagtga atgaagtaac tgaatttgca aaaacatgtg ttgctgatga gtcagctgaa      180
aattgtgaca aatcacttca tacccttttt ggagacaaat tatgcacagt tgcaactctt      240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
```

```
gatgtgatgt gcactgcttt tcatgacaat gaagagacat ttttgaaaaa atacttatat      420
gaaattgcca aagacatcc ttactttat gccccggaac tccttttctt tgctaaaagg       480
tataaagctg cttttacaga atgttgccaa gctgctgata aagctgcctg cctgttgcca      540
aagctcgatg aacttcggga tgaagggaag gtttcgtctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg cttgaatgtg ctgatgacag gcggaccctt      780
gccaagtata tctgtgaaaa tcaagattcg atctccagta aactgaagga atgctgtgaa      840
aaacctctgt tggaaaaatc ccactgcatt gccgaagtgg aaaatgatga gatgcctgct      900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc gccacatatg aaaccactct agagaagtgc     1080
tgtgccgctg cagatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga aagtacccca agtgtcaact     1260
ccaactcttg tagaggtctc aagaaaccta ggaaaagtgg gcagcaaatg ttgtaaacat     1320
cctgaagcaa aaagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca ggcgaccatg cttttcagct ctggaagtcg atgaaacata cgttcccaaa     1500
gagtttaatg ctgaaacatt caccttccat gcagatatat gcacactttc tgagaaggag     1560
agacaaatca gaaacaaac tgcacttgtt gagcttgtga acacaagcc caaggcaaca      1620 aaagagcaac tgaaagctgt tatggatgat ttcgcagctt ttgtagagaa gtgctgcaag     1680
gctgacgata aggagacctg cttttgccgag gagggtaaaa aacttgttgc tgcaagtcaa     1740
gctgccttag gcttacatca tcaccatcac catt                                1774
```

<210> SEQ ID NO 121
<211> LENGTH: 113
<212> TYPE: PRT
<213> ORGANISM: Artificial Sequence
<220> FEATURE:
<223> OTHER INFORMATION: Amino acid sequence identified using molecular biology techniques.

<400> SEQUENCE: 121

```
Ser Thr Asp Ile Gln Met Thr Gln Ser Pro Ser Ser Leu Ser Ala Ser
 1               5                  10                  15

Val Gly Asp Arg Val Thr Ile Thr Cys Arg Ala Ser Arg Pro Ile Gly
             20                  25                  30

Thr Thr Leu Ser Trp Tyr Gln Gln Lys Pro Gly Lys Ala Pro Lys Leu
         35                  40                  45

Leu Ile Leu Trp Asn Ser Arg Leu Gln Ser Gly Val Pro Ser Arg Phe
     50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Ala Gln Ala Gly Thr His
                 85                  90                  95

Pro Thr Thr Phe Gly Gln Gly Thr Lys Val Glu Ile Lys Arg Ala Ala
```

Ala

<210> SEQ ID NO 122
<211> LENGTH: 339
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 122

```
tcgacggaca tccagatgac ccagtctcca tcctccctgt ctgcatctgt aggagaccgt    60
gtcaccatca cttgccgggc aagtcgtccg attgggacga cgttaagttg gtaccagcag   120
aaaccaggga aagcccctaa gctcctgatc ctttggaatt cccgtttgca aagtggggtc   180
ccatcacgtt tcagtggcag tggatctggg acagatttca ctctcaccat cagcagtctg   240
caacctgaag attttgctac gtactactgt gcgcaggctg ggacgcatcc tacgacgttc   300
ggccaaggga ccaaggtgga atcaaacgg gcggccgca                            339
```

<210> SEQ ID NO 123
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 123

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
                20                  25                  30

Leu Ser Trp Tyr Gln Gln Lys Pro Gly Lys Ala Pro Lys Leu Leu Ile
            35                  40                  45

Met Trp Arg Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Ala Ala Leu Pro Arg
                85                  90                  95

Thr Phe Gly Gln Gly Thr Lys Val Glu Ile Lys Arg
            100                 105

<210> SEQ ID NO 124
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 124

```
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat ttcactctca ccatcagcag tctgcaacct   240
gaagattttg ctacgtacta ctgtgctcag ggtgcggcgt tgcctaggac gttcggccaa   300
```
gggaccaagg tggaaatcaa acgg                                                  324

<210> SEQ ID NO 125
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Thr
            20                  25                  30

Leu Ser Trp Tyr Gln Gln Lys Pro Gly Lys Ala Pro Lys Leu Leu Ile
        35                  40                  45

Trp Phe Gly Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105

<210> SEQ ID NO 126
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 126
gacatccaga tgacccagtc tccatcctcc ctgtctgcat ctgtaggaga ccgtgtcacc      60
atcacttgcc gggcaagtcg tccgattggg acgacgttaa gttggtacca gcagaaacca     120
gggaaagccc ctaagctcct gatctggttt ggttcccggt tgcaaagtgg ggtcccatca     180
cgtttcagtg gcagtggatc tgggacagat ttcactctca ccatcagcag tctgcaacct     240
gaagattttg ctacgtacta ctgtgcgcag gctgggacgc atcctacgac gttcggccaa     300
gggaccaagg tggaaatcaa acgg                                             324

<210> SEQ ID NO 127
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Met Leu Leu Ile
        35                  40                  45

Met Trp Ser Ser Ser Leu Gln Ser Gly Val Pro Ser Arg Phe Ser Gly

```
                    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                     85                  90                  95

Thr Phe Gly Gln Gly Thr Lys Val Glu Ile Lys Trp
                100                 105
```

<210> SEQ ID NO 128
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 128

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Gln
                 20                  25                  30

Leu Ser Trp Tyr Gln Gln Lys Pro Gly Lys Ala Pro Lys Leu Leu Ile
             35                  40                  45

Met Trp Arg Ser Ala Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                     85                  90                  95

Thr Phe Gly Gln Gly Thr Lys Val Glu Ile Lys Trp
                100                 105
```

<210> SEQ ID NO 129
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 129

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Gln
                 20                  25                  30

Leu Ser Trp Tyr Gln Gln Lys Pro Gly Lys Ala Pro Lys Leu Leu Ile
             35                  40                  45

Met Trp Arg Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                     85                  90                  95

Thr Tyr Gly Lys Gly Thr Lys Val Glu Asn Lys Trp
                100                 105
```

<210> SEQ ID NO 130
<211> LENGTH: 108
<212> TYPE: PRT

<213> ORGANISM: Artificial Sequence
<220> FEATURE:
<223> OTHER INFORMATION: Amino acid sequence identified using molecular biology techniques.

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Leu Lys His Pro Lys
                85                  90                  95

Thr Tyr Gly Gln Gly Thr Lys Val Glu Ile Lys Trp
            100                 105

<210> SEQ ID NO 131
<211> LENGTH: 108
<212> TYPE: PRT
<213> ORGANISM: Artificial Sequence
<220> FEATURE:
<223> OTHER INFORMATION: Amino acid sequence identified using molecular biology techniques.

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Met Arg His Pro Lys
                85                  90                  95

Thr Phe Gly Gln Gly Thr Lys Val Glu Ile Lys Trp
            100                 105

<210> SEQ ID NO 132
<211> LENGTH: 108
<212> TYPE: PRT
<213> ORGANISM: Artificial Sequence
<220> FEATURE:
<223> OTHER INFORMATION: Amino acid sequence identified using molecular biology techniques.

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

-continued

```
Met Trp Arg Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Tyr Gly Gln Gly Thr Lys Val Glu Asn Lys Trp
            100                 105

<210> SEQ ID NO 133
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 133

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
             20                  25                  30

Leu Ser Trp Tyr Gln Gln Lys Pro Gly Lys Ala Pro Lys Leu Leu Ile
         35                  40                  45

Met Trp Arg Ser Ala Leu Gln Asn Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Trp
            100                 105

<210> SEQ ID NO 134
<211> LENGTH: 107
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 134

Ile Gln Met Thr Gln Ser Pro Ser Ser Leu Phe Ala Ser Val Gly Asp
 1               5                  10                  15

Arg Val Thr Ile Thr Cys Arg Ala Ser Gln Trp Ile Gly Ser Gln Leu
             20                  25                  30

Ser Trp Tyr Gln Gln Lys Pro Gly Lys Ala Pro Lys Leu Leu Ile Met
         35                  40                  45

Trp Arg Ser Ser Leu Gln Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Ala Gln Gly Leu Arg Lys Pro Lys Thr
                 85                  90                  95

Phe Gly Gln Gly Thr Lys Val Lys Ile Lys Trp
            100                 105

<210> SEQ ID NO 135
```

<211> LENGTH: 108
<212> TYPE: PRT
<213> ORGANISM: Artificial Sequence
<220> FEATURE:
<223> OTHER INFORMATION: Amino acid sequence identified using molecular biology techniques.

<400> SEQUENCE: 135

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ala Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                85                  90                  95

Thr Tyr Gly Gln Gly Thr Lys Val Glu Ile Lys Trp
            100                 105

<210> SEQ ID NO 136
<211> LENGTH: 108
<212> TYPE: PRT
<213> ORGANISM: Artificial Sequence
<220> FEATURE:
<223> OTHER INFORMATION: Amino acid sequence identified using molecular biology techniques.

<400> SEQUENCE: 136

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ala Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg Tyr Pro Lys
                85                  90                  95

Thr Phe Gly Gln Gly Thr Lys Val Glu Ile Lys Trp
            100                 105

<210> SEQ ID NO 137
<211> LENGTH: 108
<212> TYPE: PRT
<213> ORGANISM: Artificial Sequence
<220> FEATURE:
<223> OTHER INFORMATION: Amino acid sequence identified using molecular biology techniques.

<400> SEQUENCE: 137

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
            20                  25                  30

```
Leu Ser Trp Tyr Gln Gln Lys Pro Gly Lys Ala Pro Lys Leu Leu Ile
            35                  40                  45

Met Trp Arg Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Tyr Gly Gln Gly Thr Lys Val Glu Ile Lys Arg
             100                 105
```

<210> SEQ ID NO 138
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 138

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
             20                  25                  30

Leu Ser Trp Tyr Gln Gln Lys Pro Gly Lys Ala Pro Lys Leu Leu Ile
            35                  40                  45

Met Trp Arg Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Tyr Gly Gln Gly Thr Lys Val Glu Asn Lys Arg
             100                 105
```

<210> SEQ ID NO 139
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 139

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
             20                  25                  30

Leu Ser Trp Tyr Gln Gln Lys Pro Gly Lys Ala Pro Lys Leu Leu Ile
            35                  40                  45

Met Trp Arg Ser Ala Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Arg
             100                 105
```

<210> SEQ ID NO 140
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Leu Arg His Pro Lys
                85                  90                  95

Thr Tyr Gly Lys Gly Thr Lys Val Glu Ile Lys Arg
            100                 105

<210> SEQ ID NO 141
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Leu Arg His Pro Lys
                85                  90                  95

Thr Tyr Gly Lys Gly Thr Lys Val Glu Asn Lys Arg
            100                 105

<210> SEQ ID NO 142
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 142
gacatccaga tgacccagtc tccatcctcc ctgtctgcat ctgtaggaga ccgtgtcacc        60
atcacttgcc gggcaagtca gtggattggg tctcagttat cttggtacca gcagaaacca       120

| | |
|---|---|
| gggaaagccc ctatgctcct gatcatgtgg agttcctcgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtgctcag ggtttgaggc atcctaagac gttcggccaa | 300 |
| gggaccaagg tggaaatcaa atgg | 324 |

<210> SEQ ID NO 143
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 143

| | |
|---|---|
| gacatccaga tgacccagtc tccatcctcc ctgtctgcat ctgtaggaga ccgtgtcacc | 60 |
| atcacttgcc gggcaagtca gtggattggg tctcagttat cttggtacca gcagaaacca | 120 |
| gggaaagccc ctaagctcct gatcatgtgg cgttccgcgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtgctcag ggtttgaggc atcctaagac gttcggccaa | 300 |
| gggaccaagg tggaaatcaa atgg | 324 |

<210> SEQ ID NO 144
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 144

| | |
|---|---|
| gacatccaga tgacccagtc tccatcctcc ctgtctgcat ctgtaggaga ccgtgtcacc | 60 |
| atcacttgcc gggcaagtca gtggattggg tctcagttat cttggtacca gcagaaacca | 120 |
| gggaaagccc ctaagctcct gatcatgtgg cgttcctcgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtgctcag ggtttgaggc atcctaagac gtacggcaaa | 300 |
| gggaccaagg tggaaaacaa atgg | 324 |

<210> SEQ ID NO 145
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 145

| | |
|---|---|
| gacatccaga tgacccagtc tccatcctcc ctgtctgcat ctgtaggaga ccgtgtcacc | 60 |
| atcacttgcc gggcaagtca gtggattggg tctcagttat cttggtacca gcagaaacca | 120 |
| gggaaagccc ctaagctcct gatcatgtgg cgttcctcgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtgctcag ggtttgaagc atcctaagac gtacggccaa | 300 |
| gggaccaagg tggaaatcaa atgg | 324 |

<210> SEQ ID NO 146

```
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 146
gacatccaga tgacccagtc tccatcctcc ctgtctgcat ctgtaggaga ccgtgtcacc      60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtatgaggc atcctaagac gttcggccaa    300
gggaccaagg tggaaatcaa atgg                                           324

<210> SEQ ID NO 147
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 147
gacatccaga tgacccagtc tccatcctcc ctgtctgcat ctgtaggaga ccgtgtcacc      60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgcggc atcctaagac gtacggccaa    300
gggaccaagg tggaaaacaa atgg                                           324

<210> SEQ ID NO 148
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 148
gacatccaga tgacccagtc tccatcctcc ctgtctgcat ctgtaggaga ccgtgtcacc      60
atcacttgcc gggcaagtca gtggattggg tctcagttat cttggtacca gcagaaacca    120
gggaaagccc ctaagctcct gatcatgtgg cgttccgcgt tacaaaatgg ggtcccatca    180
cgtttcagtg gcagtggatc tgggacagat ttcactctca ccatcagcag tctgcaacct    240
gaagattttg ctacgtacta ctgtgctcag ggtttgaggc atcctaagac gttcggccaa    300
gggaccaagg tggaaatcaa atgg                                           324

<210> SEQ ID NO 149
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 149
gacatccaga tgacccagtc tccatcctcc ctgtttgcat ctgtaggaga ccgtgtcacc      60
```

```
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgagga aacctaagac tttcggccaa    300
gggaccaagg tgaaaatcaa atgg                                           324
```

<210> SEQ ID NO 150
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 150

```
gacatccaga tgacccagtc tccatcctcc ctgtctgcat ctgtaggaga ccgtgtcacc     60
atcacttgcc gggcaagtca gtggattggg tctcagttat cttggtacca gcagaaacca    120
gggaaagccc ctaagctcct gatcatgtgg cgttccgcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggc atcctaaaac gtacggccaa    300
gggaccaagg tgaaaatcaa atgg                                           324
```

<210> SEQ ID NO 151
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 151

```
gacatccaga tgacccagtc tccatcctcc ctgtctgcat ctgtaggaga ccgtgtcacc     60
atcacttgcc gggcaagtca gtggattggg tctcagttat cttggtacca gcagaaacca    120
gggaaagccc ctaagctcct gatcatgtgg cgttccgcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggt atcctaagac gttcggccaa    300
gggaccaagg tgaaaatcaa atgg                                           324
```

<210> SEQ ID NO 152
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 152

```
gacatccaga tgacccagtc tccatcctcc ctgtctgcat ctgtaggaga ccgtgtcacc     60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgcggc atcctaagac gtacggccaa    300
gggaccaagg tgaaaatcaa acgg                                           324
```

<210> SEQ ID NO 153
<211> LENGTH: 324
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 153

```
gacatccaga tgacccagtc tccatcctcc ctgtctgcat ctgtaggaga ccgtgtcacc      60
atcacttgcc gggcaagtca gtggattggg tctcagttat cttggtacca gcagaaacca     120
gggaaagccc ctaagctcct gatcatgtgg cgttcctcgt tgcaaagtgg ggtcccatca     180
cgtttcagtg gcagtggatc tgggacagat ttcactctca ccatcagcag tctgcaacct     240
gaagattttg ctacgtacta ctgtgctcag ggtttgcggc atcctaagac gtacggccaa     300
gggaccaagg tggaaaacaa acgg                                            324
```

<210> SEQ ID NO 154
<211> LENGTH: 324
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 154

```
gacatccaga tgacccagtc tccatcctcc ctgtctgcat ctgtaggaga ccgtgtcacc      60
atcacttgcc gggcaagtca gtggattggg tctcagttat cttggtacca gcagaaacca     120
gggaaagccc ctaagctcct gatcatgtgg cgttccgcgt tgcaaagtgg ggtcccatca     180
cgtttcagtg gcagtggatc tgggacagat ttcactctca ccatcagcag tctgcaacct     240
gaagattttg ctacgtacta ctgtgctcag ggtttgaggc atcctaagac gttcggccaa     300
gggaccaagg tggaaatcaa acgg                                            324
```

<210> SEQ ID NO 155
<211> LENGTH: 324
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 155

```
gacatccaga tgacccagtc tccatcctcc ctgtctgcat ctgtaggaga ccgtgtcacc      60
atcacttgcc gggcaagtca gtggattggg tctcagttat cttggtacca gcagaaacca     120
gggaaagccc ctaagctcct gatcatgtgg cgttcctcgt tgcaaagtgg ggtcccatca     180
cgtttcagtg gcagtggatc tgggacagat ttcactctca ccatcagcag tctgcaacct     240
gaagattttg ctacgtacta ctgtgctcag ggtttgaggc atcctaagac gtacggcaaa     300
gggaccaagg tggaaatcaa acgg                                            324
```

<210> SEQ ID NO 156
<211> LENGTH: 324
<212> TYPE: DNA
<213> ORGANISM: Artificial Sequence
<220> FEATURE:
<223> OTHER INFORMATION: Nucleic acid sequence identified using
molecular biology techniques.

```
<400> SEQUENCE: 156
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat ttcactctca ccatcagcag tctgcaacct   240
gaagattttg ctacgtacta ctgtgctcag ggtttgaggc atcctaagac gtacggcaaa   300
gggaccaagg tggaaaacaa acgg                                          324

<210> SEQ ID NO 157
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 157

Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Pro Ile Gly Thr Met
            20                  25                  30

Leu Ser Trp Tyr Gln Gln Lys Pro Gly Lys Ala Pro Lys Leu Leu Ile
        35                  40                  45

Leu Phe Gly Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105

<210> SEQ ID NO 158
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 158
gacatccaga tgacccagtc tccatcctcc ctgtctgcat ctgtaggaga ccgtgtcacc    60
atcacttgcc gggcaagtcg tccgattggg acgatgttaa gttggtacca gcagaaacca   120
gggaaagccc ctaagctcct gatcttgttt ggttcccggt tgcaaagtgg ggtcccatca   180
cgtttcagtg gcagtggatc tgggacagat ttcactctca ccatcagcag tctgcaacct   240
gaagattttg ctacgtacta ctgtgcgcag gctgggacgc atcctacgac gttcggccaa   300
gggaccaagg tggaaatcaa acgg                                          324
```

US 9,012,609 B2

ANTI-SERUM ALBUMIN BINDING VARIANTS

This application is a 371 of International Application No. PCT/EP2011/063999, filed 12 Aug. 2011, which claims the benefit of U.S. Provisional Application No. 61/373,397, filed 13 Aug. 2010, both of which are herein incorporated by reference in their entireties.

The invention relates to improved variants of anti-serum albumin immunoglobulin single variable domains, as well as ligands and drug conjugates comprising such variants, compositions, nucleic acids, vectors and hosts. The invention also relates to the identification of an epitope in serum albumin that is bound by these anti-serum albumin immunoglobulin single variable domains and the specific amino acid residues within those anti-serum albumin immunoglobulin single variable domains that make contact with serum albumin.

BACKGROUND OF THE INVENTION

WO04003019 and WO2008/096158 disclose anti-serum albumin (SA) binding moieties, such as anti-SA immunoglobulin single variable domains (dAbs), which have therapeutically-useful half-lives. These documents disclose monomer anti-SA dAbs as well as multi-specific ligands comprising such dAbs, e.g., ligands comprising an anti-SA dAb and a dAb that specifically binds a target antigen, such as TNFR1. Binding moieties are disclosed that specifically bind serum albumins from more than one species, e.g. human/mouse cross-reactive anti-SA dAbs.

WO05118642 and WO2006/059106 disclose the concept of conjugating or associating an anti-SA binding moiety, such as an anti-SA immunoglobulin single variable domain, to a drug, in order to increase the half-life of the drug. Protein, peptide and NCE (new chemical entity) drugs are disclosed and exemplified. WO2006/059106 discloses the use of this concept to increase the half-life of insulinotropic agents, e.g., incretin hormones such as glucagon-like peptide (GLP)-1.

Reference is also made to Holt et al, "Anti-Serum albumin domain antibodies for extending the half-lives of short lived drugs", Protein Engineering, Design & Selection, vol 21, no 5, pp 283-288, 2008.

WO2008/096158 discloses the molecules given the name DOM7h-11 and DOM7h-14, which are good anti-SA dAbs. PCT/EP2010/060112 describes $V_H$ AlbudAbs and affinity matured derivatives thereof. It would be desirable to provide improved dAbs that are variants of DOM7h-11 or DOM7h-14, or improved $V_H$ AlbudAbs™, and that specifically bind serum albumin, preferably albumins from human and non-human species, which would provide utility in animal models of disease as well as for human therapy and/or diagnosis. It would also be desirable to provide for the choice between relatively modest- and high-affinity anti-SA binding moieties (dAbs). Such moieties could be linked to drugs, the anti-SA binding moiety being chosen according to the contemplated end-application. This would allow the drug to be better tailored to treating and/or preventing chronic or acute indications, depending upon the choice of anti-SA binding moiety. It would also be desirable to provide anti-SA dAbs that are monomeric or substantially so in solution. This would especially be advantageous when the anti-SA dAb is linked to a binding moiety, e.g., a dAb, that specifically binds a cell-surface receptor, such as TNFR1, with the aim of antagonizing the receptor. The monomeric state of the anti-SA dAb is useful in reducing the chance of receptor cross-linking, since multimers are less likely to form which could bind and cross-link receptors (e.g., TNFR1) on the cell surface, thus increasing the likelihood of receptor agonism and detrimental receptor signaling.

SA is an abundant plasma protein and human serum albumin (HSA) is known to bind to a number of commonly-used drugs (e.g. warfarin, diazepam, ibuprofen) (as described, for example, by Ghuman et al. J. Mol. Biol. 2005, 353, 38052). It would be advantageous to provide an anti-SA binding moiety which does not interfere with the known HSA-drug interactions.

SUMMARY OF THE INVENTION

Improved anti-SA dAbs are described in PCT/EP2010/052008 and PCT/EP2010/052007. PCT/EP2010/060112 describes $V_H$ AlbudAbs and affinity matured derivatives thereof.

As described herein, binding interactions between anti-SA dAbs and SA have been identified using three different techniques. The present inventors have therefore identified specific interactions between improved anti-SA dAbs and domain II of HSA thus identifying the residues within HSA that are involved in binding by an anti-SA dAb and those residues of an anti-SA dAb that are involved in the binding interaction. The residues from the anti-SA dAbs which interact with SA are set out in Tables 22A and B. Significant interactions are identified in Table 22A while additional residues at the interface are identified in Table 22B. Any one of the residues identified in these tables may provide an interaction with SA. These residues may be modified in order to modify SA binding of the variants.

Accordingly, in a first aspect of the invention, there is provided an anti-serum albumin (SA) immunoglobulin single variable domain variant of DOM 7h-11 (SEQ ID NO: 125) or DOM 7h-14 (SEQ ID NO: 123), or a derivative having an amino acid sequence that is at least 96, 97, 98 or 99% identical to the amino acid sequence of DOM 7h-11 (SEQ ID NO: 125) or DOM7h-14 (SEQ ID NO:123), wherein the variant comprises an amino acid substitution in at least one of positions 28, 29, 30, 31, 32, 36, 46, 49, 50, 51, 53, 67, 68, 90, 91, 92, 93 or 94 of the amino acid sequence. Positions 28, 29, 30, 31, 32, 36, 46, 49, 50, 51, 53, 67, 68, 90, 91, 92, 93 or 94 of the amino acid sequence are those positions in the sequences set out in the cited SEQ ID NOs: and relative to those residues set out in the sequences given in these SEQ ID NOs:. Suitably, the variant comprises at least 1, 2, 3, 4, 5, 6, 7, 8, 9, 10, 11, 12, 13, 14, 15, 16 or 17 amino acid mutations. Significant interactions are set out in Table 22A. Accordingly, in one embodiment, the variant comprises an amino acid substitution in at least one of positions 30, 31, 32, 49, 50, 51, 53, 67, 91 or 94 of the amino acid sequence. Suitably, the variant comprises at least 1, 2, 3, 4, 5, 6, 7, 8, 9 or 10 amino acid mutations. Such a substitution may be to provide the amino acid that is found at these positions in the anti-SA immunoglobulin single variable domain DOM7h-11-3 (SEQ ID NO:2), DOM7h-11-15 (SEQ ID NO:1) or DOM7h14-10 (SEQ ID NO:83) or an equivalent conservative substitution. Suitably, such a substitution may serve to improve binding affinity to SA. In one embodiment, the variant is not a single variable domain selected from DOM7h-11-3, DOM7h-11-15 or DOM7h-14-10. In another embodiment, the variant is not a single variable domain as described in PCT/EP2010/052008 and PCT/EP2010/052007.

In another aspect, there is provided an anti-serum albumin (SA) immunoglobulin single variable domain variant of DOM 7r-31 (SEQ ID NO: 71) or DOM 7r-92 (SEQ ID NO: 75), or a derivative having an amino acid sequence that is at least 96, 97, 98 or 99% identical to the amino acid sequence of DOM 7r-31 (SEQ ID NO: 71) or DOM 7r-92 (SEQ ID NO: 75), wherein the variant comprises an amino acid substitution in at least one of positions 28, 29, 30, 31, 32, 36, 46, 49, 50, 51, 53, 67, 68, 90, 91, 92, 93 or 94 of the amino acid sequence. In one embodiment, the variant is not a single variable domain DOM7r-92-4. In another embodiment, the variant is not a single variant domain as described in PCT/EP2010/060112.

In another aspect, the invention provides an anti-serum albumin (SA) immunoglobulin single variable domain variant of DOM7h-11-3 (SEQ ID NO: 2) or DOM7h-11-15 (SEQ ID NO: 1), or a derivative having an amino acid sequence that is at least 96, 97, 98 or 99% identical to the amino acid sequence of DOM7h-11-3 (SEQ ID NO: 2) or DOM7h-11-15 (SEQ ID NO: 1), wherein the variant comprises an amino acid substitution in at least one of positions 28, 29, 30, 31, 32, 36, 46, 49, 50, 51, 53, 67, 68, 90, 91, 92, 93 or 94 of the amino acid sequence. Suitably, the variant comprises at least 1, 2, 3, 4, 5, 6, 7, 8, 9, 10, 11, 12, 13, 14, 15, 16 or 17 amino acid mutations. In one embodiment of this aspect, the variant comprises an amino acid substitution in at least one of positions 30, 31, 32, 49, 50, 51, 53, 67, 91 or 94 of the amino acid sequence. Suitably, the variant comprises at least 1, 2, 3, 4, 5, 6, 7, 8, 9 or 10 amino acid mutations.

Amino acid substitution at any of the residues identified in Tables 22A or 22B may enable modification of the binding properties of an anti-SA dAb. Importantly, substitutions can be made to modify the affinity of binding to SA to achieve the desired affinity for a particular application.

Thus embodiments of any aspect of the invention provide anti-SA dAb variants having good anti-serum albumin affinities. The choice of variant can allow for tailoring of half-life according to the desired therapeutic and/or prophylactic setting. For example, in one embodiment, the affinity of the variant for serum albumin is relatively high, such that the variant would be useful for inclusion in products that find utility in treating and/or preventing chronic or persistent diseases, conditions, toxicity or other chronic indications, for example. In one embodiment, the affinity of the variant for serum albumin is relatively modest, such that the variant would be useful for inclusion in products that find utility in treating and/or preventing acute diseases, conditions, toxicity or other acute indications, for example. In one embodiment, the affinity of the variant for serum albumin is intermediate, such that the variant would be useful for inclusion in products that find utility in treating and/or preventing acute or chronic diseases, conditions, toxicity or other acute or chronic indications, for example.

It is conceivable that a molecule with an appropriately high affinity and specificity for serum albumin would stay in circulation long enough to have the desired therapeutic effect (Tomlinson, *Nature Biotechnology* 22, 521-522 (2004)). Here, a high affinity anti-SA variant would stay in serum circulation matching that of the species' serum albumin (WO2008096158). Once in circulation, any fused therapeutic agent to the AlbudAb™ variant (an AlbudAb is an anti-serum albumin dAb or immunoglobulin single variable domain), be it NCE, peptide or protein, consequently would be able to act longer on its target and exhibit a longer lasting therapeutic effect. This would allow for targeting chronic or persistent diseases without the need of frequent dosing.

A variant with moderate affinity (but specificity to SA) would only stay in serum circulation for a short time (e.g., for a few hours or a few days) allowing for the specific targeting of therapeutic targets involved in acute diseases by the fused therapeutic agent.

This way it is possible to tailor the anti-SA-containing product to the therapeutic disease area by choosing an anti-SA variant with the appropriate albumin binding affinity and/or serum half-life.

In one embodiment, the invention provides an anti-serum albumin (SA) immunoglobulin single variable domain variant of DOM7h-11-15 (SEQ ID NO: 1), or a derivative having an amino acid sequence that is at least 96, 97, 98 or 99% identical to the amino acid sequence of DOM7h-11-15 (SEQ ID NO: 1), comprising an amino acid substitution in at least one of positions Gly30, Thr31, Met32, Leu49, Ala50, Phe51, Arg53, Ser67, Ala91 or His94 of the amino acid sequence.

In one embodiment, there is provided a variant in accordance with any aspect or embodiment of the invention wherein the substitution is a conservative amino acid substitution. Suitable conservative amino acid substitutions are known by those skilled in the art and are exemplified herein in the following text. Suitably, a conservative amino acid substitution will maintain similar contact interactions with SA. Such conservative amino acid substitution may allow similar binding affinities to the parental molecule to be maintained.

Accordingly, in one embodiment, the variant comprises at least one mutation compared to DOM 7h-11-15 selected from the following:
Position Gly 30=Pro, Ala
Position Thr 31=Ser
Position Thr 32=Ser
Position Leu 49=Norleucine, Ile, Val, Met, Ala, Phe
Position Trp 50=Tyr, Phe
Position Asn 51=Gln
Position Arg 53=Lys, Gln, Asn
Position Ser 67=Thr, Ala, Cys
Position Ala 91=Val, Leu, Ile
Position H is 94=Asn, Gln, Lys, Arg In another embodiment, there is provided an anti-serum albumin (SA) immunoglobulin single variable domain variant of DOM 7h-11-3 (SEQ ID NO: 2), or a derivative having an amino acid sequence that is at least 96, 97, 98 or 99% identical to the amino acid sequence of DOM 7h-11-3 (SEQ ID NO: 2), wherein the variant comprises an amino acid substitution in at least one of positions Gly30, Thr31, Thr32, Leu49, Trp50, Asn51, Arg53, Ser67, Ala91 or His94 of the amino acid sequence.

Suitably, the variant comprises a conservative substitution such that the variant comprises at least one mutation compared to DOM7h-11-3 selected from the following:
Position Gly30=Pro, Ala
Position Thr31=Ser
Position Thr32=Ser
Position Leu49=Norleucine, Ile, Val, Met, Ala, Phe
Position Trp50=Tyr, Phe
Position Asn51=Gln
Position Arg53=Lys, Gln, Asn
Position Ser67=Thr, Ala, Cys
Position Ala91=Val, Leu, Ile
Position His94=Asn, Gln, Lys, Arg In another embodiment of any aspect or embodiment of the invention, the substitution is not a conservative substitution. Introducing a non-conservative substitution/mutation at one of the residues known to be involved in binding to SA is one way in which affinity to SA may be decreased or otherwise altered.

In one embodiment of any aspect or embodiment of the invention SA is SA from an animal, e.g., a mammal, e.g., a non-human primate (such as a baboon, rhesus monkey or Cynomolgus monkey), mouse, human, rabbit, rat, dog, cat or pig. In one embodiment SA is human SA (HSA).

In another aspect, the invention provides an HSA binding moiety which binds to an epitope comprising at least part of the interface defined by amino acids 227, 228, 229, 230, 232, 233, 263, 307, 308, 309, 314, 317, 318, 321, 322, 325, 326, 329 and 333 of HSA (wherein sequence is given in SEQ ID NO:81). In one embodiment, the binding moiety binds to an epitope comprising at least part of the interface defined by amino acids 228, 230, 308, 309, 317, 318, 321, 322, 325, 326 and 329 of HSA. The residues of HSA which interact with the anti-HSA binding moieties exemplified by anti-SA dAbs herein are set out in Tables 22A and B. Significant interactions are identified in Table 22A while additional residues at the interface are identified in Table 22B. Any one of the residues identified in these tables may provide an interaction between HSA and the HSA binding moiety.

Suitably, the binding moiety may comprise amino acids identified in SEQ ID NOs: 1 or 2 at positions 28, 29, 30, 31, 32, 36, 46, 49, 50, 51, 53, 67, 68, 90, 91, 92, 93 or 94 of the amino acid sequence wherein these amino acids enable binding to SA. However, these amino acids may be part of a domain which is a derivative of a non-immunoglobulin protein scaffold. In one embodiment, the binding moiety is an antibody. Suitably, the binding moiety is an anti-SA immunoglobulin single variable domain antibody.

In one embodiment the variant or binding moiety in accordance with any aspect or embodiment of the invention comprises a binding site that specifically binds human SA with a dissociation constant (KD) of from about 0.1 to about 10000 nM, optionally from about 1 to about 6000 nM, as determined by surface plasmon resonance. In another embodiment, the variant or binding moiety in accordance with any aspect or embodiment of the invention comprises a binding site that specifically binds human SA with an off-rate constant ($K_d$) of from about $1.5 \times 10^{-4}$ to about $0.1$ sec$^{-1}$, optionally from about $3 \times 10^{-4}$ to about $0.1$ sec$^{-1}$ as determined by surface plasmon resonance. In another embodiment the variant or binding moiety in accordance with any aspect or embodiment of the invention comprises a binding site that specifically binds human SA with an on-rate constant ($K_a$) of from about $2 \times 10^6$ to about $1 \times 10^4$ M$^{-1}$ sec$^{-1}$, optionally from about $1 \times 10^6$ to about $2 \times 10^4$ M$^{-1}$ sec$^{-1}$ as determined by surface plasmon resonance. In a further embodiment, the variant or binding moiety in accordance with any aspect or embodiment of the invention comprises a binding site that specifically binds Cynomolgus monkey SA with a dissociation constant (KD) of from about 0.1 to about 10000 nM, optionally from about 1 to about 6000 nM, as determined by surface plasmon resonance. In yet a further embodiment, the variant or binding moiety in accordance with any aspect or embodiment of the invention comprises a binding site that specifically binds Cynomolgus monkey SA with an off-rate constant ($K_d$) of from about $1.5 \times 10^{-4}$ to about $0.1$ sec$^{-1}$, optionally from about $3 \times 10^{-4}$ to about $0.1$ sec$^{-1}$ as determined by surface plasmon resonance. Another embodiment provides a variant or binding moiety in accordance with any aspect or embodiment of the invention, wherein the variant comprises a binding site that specifically binds Cynomolgus monkey SA with an on-rate constant ($K_a$) of from about $2 \times 10^6$ to about $1 \times 10^4$ M$^{-1}$ sec$^{-1}$, optionally from about $1 \times 10^6$ to about $5 \times 10^3$ M$^{-1}$ sec$^{-1}$ as determined by surface plasmon resonance.

An aspect of the invention provides a multispecific ligand comprising any anti-SA variant or SA-binding moiety as described above and a binding moiety that specifically binds a target antigen other than SA.

An aspect of the invention provides fusion proteins, conjugates or compositions comprising any variant or binding moiety in accordance with the invention. For example, the invention provides e.g., a fusion protein or fusion with a peptide or NCE (new chemical entity) drug, comprising a polypeptide, protein, peptide or NCE drug fused or conjugated (for an NCE) to any variant or binding moiety as described above. In one embodiment, the variant or binding moiety gives only a modest drop in affinity when fused or conjugated to a partner making them useful in fusion products. An aspect of the invention provides a composition comprising a variant, fusion protein or ligand of any preceding aspect and a pharmaceutically acceptable diluent, carrier, excipient or vehicle.

Another aspect of the invention provides a nucleic acid comprising a nucleotide sequence encoding a variant, binding moiety, multispecific ligand or fusion protein in accordance with any aspect or embodiment of the invention.

Another aspect provides a nucleic acid comprising the nucleotide sequence of a DOM7h-11, DOM7h-14, DOM7h-11-3 or DOM7h-11-15 variant in accordance with the invention or a nucleotide sequence that is at least 80% identical to said selected sequence. Further aspects provide a vector comprising a nucleic acid of the invention and an isolated host cell comprising such a vector.

An aspect of the invention provides a method of treating or preventing a disease or disorder in a patient, comprising administering at least one dose of a variant or binding moiety according to any aspect or embodiment of the invention to said patient. The invention further provides a variant or binding moiety in accordance with the present invention for use as a medicament.

In another aspect of the invention there is provided a method for affinity maturation of an anti-SA immunoglobulin single variable domain comprising taking an anti-SA immunoglobulin single variable domain and introducing a mutation at an amino acid at any one of positions 28, 29, 30, 31, 32, 36, 46, 49, 50, 51, 53, 67, 68, 90, 91, 92, 93 or 94 of the amino acid sequence of an anti-SA immunoglobulin single variable domain. In one embodiment the anti-SA immunoglobulin single variable domain is, or is derived from, the amino acid sequence of DOM7h-11 or DOM7h-14. Methods for obtaining anti-SA immunoglobulin single variable domain molecules are described, for example, in PCT/EP2010/052008 and PCT/EP2010/052007. In one embodiment, the maturation may be in silico. Suitable in silico methods are described, for example, in Barderas et al. (2008), PNAS, 105, 26, p. 9029-9034. Preferably, the method comprises introducing a mutation at any one of the amino acids at positions 30, 31, 32, 49, 50, 51, 53, 67, 91 or 94 or the amino acid sequence.

Another aspect provides a method of modifying the binding affinity of an anti-SA immunoglobulin single variable domain comprising mutating an amino acid at any one of positions 30, 31, 32, 49, 50, 51, 53, 67, 91 or 94 of the amino acid sequence of an anti-SA immunoglobulin single variable domain. Suitably the anti-SA immunoglobulin single variable domain is a DOM7h-11 or DOM7h-14 derivative. Mutations may be to introduce conservative or non-conservative amino acid substitutions as described above.

In these aspects, suitably the mutation at any one of these positions is chosen to modify the affinity of binding to SA of the matured sequences when compared to the parental anti-SA immunoglobulin single variable domain.

The present inventors have identified a specific region of Serum Albumin that can be bound by an anti-SA binding moiety. Advantageously, this region is one which can be bound by a binding moiety, serving to enhance the half life of the bound moiety whilst not blocking any of the known drug binding sites such that the binding interaction does not have an effect on the other drug-binding properties of Serum Albumin. The binding portion identified can be used to identify binding moieties that preferentially bind to this region.

Accordingly, in another aspect of the invention, there is provided a method of identifying SA binding moieties comprising taking a portion of HSA defined by amino acids 213-229, 231-238, 321-331, 334-342 or 348-357; or 213-219, 222-228, 231-238, 311-218, 321-324, 329-333 or 347-357; or 321-326 or 329-331 wherein reference to amino acid residues are references to those amino acids set out in SEQ ID NO: 81, and using said portions in a binding assay or screen. In another aspect there is provided a method for generating an anti-HSA binding agent comprising taking a portion of HSA defined by amino acids 213-229, 231-238, 321-331, 334-342 or 348-357; or 213-219, 222-228, 231-238, 311-218, 321-324, 329-333 or 347-357; or 321-326 or 329-331 wherein reference to amino acid residues are references to those amino acids set out in SEQ ID NO: 81, and using these portions in a screen or assay.

Suitably an anti-HSA binding moiety may be derived using a part of HSA comprising the binding epitope described herein. In one embodiment, the method comprises providing an HSA polypeptide comprising at least part of the binding interface defined by amino acids 228, 230, 308, 309, 317, 318, 321, 322, 325, 326 and 329 of HSA.

BRIEF DESCRIPTION OF THE DRAWINGS

FIG. 2: Kinetic parameters of DOM7h-11 variants. KD units=nM; Kd units=sec$^{-1}$; Ka units=M$^{-1}$ sec$^{-1}$. The notation A e-B means A×10$^{-B}$ and C e D means C×10$^{D}$. The overall kinetic ranges in various species, as supported by the examples below, are indicated. Optional ranges are also provided for use in particular therapeutic settings (acute or chronic indications, conditions or diseases and "intermediate" for use in both chronic and acute settings). High affinity dAbs and products comprising these are useful for chronic settings. Medium affinity dAbs and products comprising these are useful for intermediate settings. Low affinity dAbs and products comprising these are useful for acute settings. The affinity in this respect is the affinity for serum albumin. Various example anti-serum dAbs and fusion proteins are listed, and these support the ranges disclosed. Many of the examples have favourable kinetics in human and one or more non-human animals (e.g., in human and Cynomolgus monkey and/or mouse). Choice of dAb or product comprising this can be tailored, according to the invention, depending on the setting (e.g., chronic or acute) to be treated therapeutically.

FIG. 3: Sequence segments of HSA identified as possible DOM7h-11-3 epitopes from H/D exchange data FIG. 4: Overall structure of HSA in complex with DOM7h11-15. HSA and DOM7h11-15 are depicted schematically in ribbon representation. Chains A and C are HSA; Chain B and D are DOM7h-11-15.

FIG. 6: Alignment of DOM7h-11 lineage AlbudAbs.

FIG. 10: Nucleic and amino acid sequences.

FIG. 11: Difference in deuteration levels in each segment of HSA compared with and without (A) DOM7h-11-3, (B) DOM7h-14-10 and (C) DOM7r-92-4 complexation.

DETAILED DESCRIPTION OF THE INVENTION

Figure 1B:
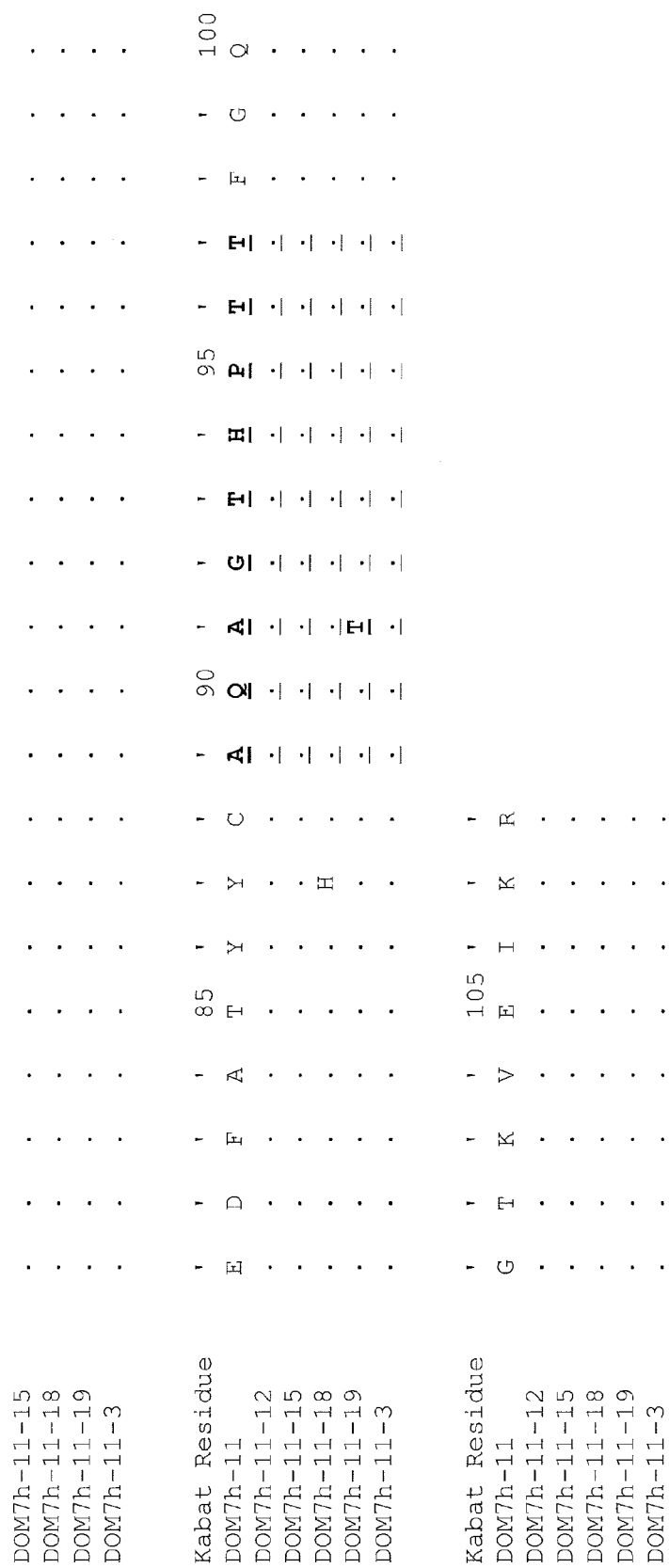
FIG. 1: Amino-acid sequence alignment for DOM7h-11 variant dAbs. A "." at a particular position indicates the same amino as found in DOM7h-11 at that position. The CDRs are indicated by underlining and bold text (the first underlined sequence is CDR1, the second underlined sequence is CDR2 and the third underlined sequence is CDR3).

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods.

A "patient" is any animal, e.g., a mammal, e.g., a non-human primate (such as a baboon, rhesus monkey or Cynomolgus monkey), mouse, human, rabbit, rat, dog, cat or pig. In one embodiment, the patient is a human.

As used herein an antibody refers to IgG, IgM, IgA, IgD or IgE or a fragment (such as a Fab, Fab', F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a dAb, $V_H$, $V_{HH}$, $V_L$), and modified versions of any of the foregoing (e.g., modified by the covalent attachment of polyethylene glycol or other suitable polymer or a humanized $V_{HH}$).

The phrase "immunoglobulin single variable domain" refers to an antibody variable domain ($V_H$, $V_{HH}$, $V_L$) that specifically binds an antigen or epitope independently of different V regions or domains. An immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. A "single immunoglobulin variable domain" is the same as an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

A "domain" is a folded protein structure which has tertiary structure independent of the rest of the protein. Generally, domains are responsible for discrete functional properties of proteins and, in many cases, may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

In the instant application, the term "prevention" and "preventing" involves administration of the protective composition prior to the induction of the disease or condition. "Treatment" and "treating" involves administration of the protective composition after disease or condition symptoms become manifest. "Suppression" or "suppressing" refers to administration of the composition after an inductive event, but prior to the clinical appearance of the disease or condition.

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds target antigen) administered to a subject over the course of one day (24 hours) (daily dose), two days, one week, two weeks, three weeks or one or more months (e.g., by a single administration, or by two or more administrations). The interval between doses can be any desired amount of time. The term "pharmaceutically effective" when referring to a dose means sufficient amount of the ligand, domain or pharmaceutically active agent to provide the desired effect. The amount that is "effective" will vary from subject to subject, depending on the age and general condition of the individual, the particular drug or pharmaceutically active agent and the like. Thus, it is not always possible to specify an exact "effective" amount applicable for all patients. However, an appropriate "effective" dose in any individual case may be determined by one of ordinary skill in the art using routine experimentation.

Methods for pharmacokinetic analysis and determination of ligand (e.g., single variable domain, fusion protein or multi-specific ligand) half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC). Optionally, all pharmacokinetic parameters and values quoted herein are to be read as being values in a human. Optionally, all pharmacokinetic parameters and values quoted herein are to be read as being values in a mouse or rat or Cynomolgus monkey.

Half lives (t½ alpha and t½ beta) and AUC can be determined from a curve of serum concentration of ligand against time. The WinNonlin analysis package, e.g. version 5.1 (available from Pharsight Corp., Mountain View, Calif. 94040, USA) can be used, for example, to model the curve. When two-compartment modeling is used, in a first phase (the alpha phase) the ligand is undergoing mainly distribution in the patient, with some elimination. A second phase (beta phase) is the phase when the ligand has been distributed and the serum concentration is decreasing as the ligand is cleared from the patient. The t alpha half life is the half life of the first phase and the t beta half life is the half life of the second phase. Thus, in one embodiment, in the context of the present invention, the variable domain, fusion protein or ligand has at alpha half life in the range of (or of about) 15 minutes or more. In one embodiment, the lower end of the range is (or is about) 30 minutes, 45 minutes, 1 hour, 2 hours, 3 hours, 4 hours, 5 hours, 6 hours, 7 hours, 10 hours, 11 hours or 12 hours. In addition, or alternatively, the variable domain, fusion protein or ligand according to the invention will have at alpha half life in the range of up to and including 12 hours (or about 12 hours). In one embodiment, the upper end of the range is (or is about) 11, 10, 9, 8, 7, 6 or 5 hours. An example of a suitable range is (or is about) 1 to 6 hours, 2 to 5 hours or 3 to 4 hours.

In one embodiment, the present invention provides the variable domain, fusion protein or ligand according to the invention has at beta half life in the range of (or of about) 2.5 hours or more. In one embodiment, the lower end of the range is (or is about) 3 hours, 4 hours, 5 hours, 6 hours, 7 hours, 10 hours, 11 hours, or 12 hours. In addition, or alternatively, the t beta half life is (or is about) up to and including 21 or 25 days. In one embodiment, the upper end of the range is (or is about) 12 hours, 24 hours, 2 days, 3 days, days, 10 days, 15 days, 19 days, 20 days, 21 days or 22 days. For example, the variable domain, fusion protein or ligand according to the invention will have at beta half life in the range 12 to 60 hours (or about 12 to 60 hours). In a further embodiment, it will be in the range 12 to 48 hours (or about 12 to 48 hours). In a further embodiment still, it will be in the range 12 to 26 hours (or about 12 to 26 hours).

As an alternative to using two-compartment modeling, the skilled person will be familiar with the use of non-compartmental modeling, which can be used to determine terminal half-lives (in this respect, the term "terminal half-life" as used herein means a terminal half-life determined using non-compartmental modeling). The WinNonlin analysis package, e.g. version 5.1 (available from Pharsight Corp., Mountain View, Calif. 94040, USA) can be used, for example, to model the curve in this way. In this instance, in one embodiment the single variable domain, fusion protein or ligand has a terminal half life of at least (or at least about) 8 hours, 10 hours, 12 hours, 15 hours, 28 hours, 20 hours, 1 day, 2 days, 3 days, 7 days, 14 days, 15 days, 16 days, 17 days, 18 days, 19 days, 20 days, 21 days, 22 days, 23 days, 24 days or 25 days. In one embodiment, the upper end of this range is (or is about) 24 hours, 48 hours, 60 hours or 72 hours or 120 hours. For example, the terminal half-life is (or is about) from 8 hours to 60 hours, or 8 hours to 48 hours or 12 to 120 hours, e.g., in man.

In addition, or alternatively to the above criteria, the variable domain, fusion protein or ligand according to the invention has an AUC value (area under the curve) in the range of (or of about) 1 mg·min/ml or more. In one embodiment, the lower end of the range is (or is about) 5, 10, 15, 20, 30, 100, 200 or 300 mg·min/ml. In addition, or alternatively, the variable domain, fusion protein or ligand according to the invention has an AUC in the range of (or of about) up to 600 mg·min/ml. In one embodiment, the upper end of the range is (or is about) 500, 400, 300, 200, 150, 100, 75 or 50 mg·min/ml. Advantageously the variable domain, fusion protein or ligand will have an AUC in (or about in) the range selected from the group consisting of the following: 15 to 150 mg·min/ml, 15 to 100 mg·min/ml, 15 to 75 mg·min/ml, and 15 to 50 mg·min/ml.

"Surface Plasmon Resonance": Competition assays can be used to determine if a specific antigen or epitope, such as human serum albumin, competes with another antigen or epitope, such as cynomolgus serum albumin, for binding to a serum albumin binding ligand described herein, such as a specific dAb. Similarly competition assays can be used to determine if a first ligand, such as dAb, competes with a second ligand such as a dAb for binding to a target antigen or epitope. The term "competes" as used herein refers to substance, such as a molecule, compound, preferably a protein, which is able to interfere to any extent with the specific binding interaction between two or more molecules. The phrase "does not competitively inhibit" means that substance, such as a molecule, compound, preferably a protein, does not interfere to any measurable or significant extent with the specific binding interaction between two or more molecules. The specific binding interaction between two or more molecules preferably includes the specific binding interaction between a single variable domain and its cognate partner or target. The interfering or competing molecule can be another single variable domain or it can be a molecule that is structurally and/or functionally similar to a cognate partner or target.

The term "binding moiety" refers to a domain that specifically binds an antigen or epitope independently of a different epitope or antigen binding domain. A binding moiety may be a domain antibody (dAb) or may be a domain which is a derivative of a non-immunoglobulin protein scaffold, e.g., a scaffold selected from the group consisting of CTLA-4, lipocalin, SpA, an adnectin, affibody, an avimer, GroEl, transferrin, GroES and fibronectin, which binds to a ligand other than the natural ligand (in the case of the present invention, the moiety binds serum albumin). See WO2008/096158, which discloses examples of protein scaffolds and methods for selecting antigen or epitope-specific binding domains from repertoires (see Examples 17 to 25). These specific disclosures of WO2008/096158 are expressly incorporated herein by reference as though explicitly written herein and for use with the present invention, and it is contemplated that any part of such disclosure can be incorporated into one or more claims herein. In one aspect, the invention provides a binding moiety comprising the amino acids which interact with and/ or enable binding to SA as described herein wherein the interacting amino acids are presented in the context of an alternative or non-immunoglobulin scaffold.

In one embodiment, the mutations at any of the positions identified in accordance with any aspect or embodiment of the invention are mutations to residues as exemplified in the Examples section herein. In another embodiment, mutations are to conservative amino acids substitutions of the exemplified residues.

Conservative amino acid substitutions are well know to the person skilled in the art and are exemplified by the following table:

| Amino Acid Substitution | | |
| --- | --- | --- |
| Original Residues | Exemplary Substitutions | Preferred Substitutions |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyricAcid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Conservative amino acid substitutions may also relate to non-naturally occurring amino acid residues, such as peptidomimetics and other reversed or inverted forms of amino acid moieties which may be incorporated by chemical peptide synthesis.

In one embodiment, the variant comprises one or more of the following kinetic characteristics:—

(a) The variant comprises a binding site that specifically binds human SA with a dissociation constant (KD) from (or from about) 0.1 to (or to about) 10000 nM, optionally from (or from about) 1 to (or to about) 6000 nM, as determined by surface plasmon resonance;

(b) The variant comprises a binding site that specifically binds human SA with an off-rate constant ($K_d$) from (or from about) $1.5 \times 10^4$ to (or to about) $0.1 \sec^{-1}$, optionally from (or from about) $3 \times 10^4$ to (or to about) $0.1 \sec^{-1}$ as determined by surface plasmon resonance;

(c) The variant comprises a binding site that specifically binds human SA with an on-rate constant ($K_a$) from (or from about) $2 \times 10^6$ to (or to about) $1 \times 10^4 \text{ M}^{-1} \sec^{-1}$, optionally from (or from about) $1 \times 10^6$ to (or to about) $2 \times 10^4 \text{ M}^{-1} \sec^{-1}$ as determined by surface plasmon resonance;

(d) The variant comprises a binding site that specifically binds Cynomolgus monkey SA with a dissociation constant (KD) from (or from about) 0.1 to (or to about) 10000 nM, optionally from (or from about) 1 to (or to about) 6000 nM, as determined by surface plasmon resonance;

(e) The variant of any preceding claim, wherein the variant comprises a binding site that specifically binds Cynomolgus monkey SA with an off-rate constant ($K_d$) from (or from about) $1.5 \times 10^{-4}$ to (or to about) $0.1 \text{ sec}^{-1}$, optionally from (or from about) $3 \times 10^{-4}$ to (or to about) $0.1 \text{ sec}^{-1}$ as determined by surface plasmon resonance;

(f) The variant of any preceding claim, wherein the variant comprises a binding site that specifically binds Cynomolgus monkey SA with an on-rate constant ($K_a$) from (or from about) $2 \times 10^6$ to (or to about) $1 \times 10^4 \text{ M}^{-1} \text{ sec}^{-1}$, optionally from (or from about) $1 \times 10^6$ to (or to about) $5 \times 10^3 \text{ M}^{-1} \text{ sec}^{-1}$ as determined by surface plasmon resonance;

(g) The variant comprises a binding site that specifically binds rat SA with a dissociation constant (KD) from (or from about) 1 to (or to about) 10000 nM, optionally from (or from about) 20 to (or to about) 6000 nM, as determined by surface plasmon resonance;

(h) The variant comprises a binding site that specifically binds rat SA with an off-rate constant ($K_d$) from (or from about) $2 \times 10^{-3}$ to (or to about) $0.15 \text{ sec}^{-1}$, optionally from (or from about) $9 \times 10^{-3}$ to (or to about) $0.14 \text{ sec}^{-1}$ as determined by surface plasmon resonance;

(i) The variant comprises a binding site that specifically binds rat SA with an on-rate constant ($K_a$) from (or from about) $2 \times 10^6$ to (or to about) $1 \times 10^4 \text{ M}^{-1} \text{ sec}^{-1}$, optionally from (or from about) $1 \times 10^6$ to (or to about) $3 \times 10^4 \text{ M}^{-1} \text{ sec}^{-1}$ as determined by surface plasmon resonance;

(j) The variant comprises a binding site that specifically binds mouse SA with a dissociation constant (KD) from (or from about) 1 to (or to about) 10000 nM as determined by surface plasmon resonance;

(k) The variant comprises a binding site that specifically binds mouse SA with an off-rate constant ($K_d$) from (or from about) $2 \times 10^{-3}$ to (or to about) $0.15 \text{ sec}^{-1}$ as determined by surface plasmon resonance; and/or (l) The variant comprises a binding site that specifically binds mouse SA with an on-rate constant ($K_a$) from (or from about) $2 \times 10^6$ to (or to about) $1 \times 10^4 \text{ M}^{-1} \text{ sec}^{-1}$, optionally from (or from about) $2 \times 10^6$ to (or to about) $1.5 \times 10^4 \text{ M}^{-1} \text{ sec}^{-1}$ as determined by surface plasmon resonance.

Optionally, the variant has

I: a KD according to (a) and (d), a $K_d$ according to (b) and (e), and a $K_a$ according to (c) and (f); or II: a KD according to (a) and (g), a $K_d$ according to (b) and (h), and a $K_a$ according to (c) and (i); or III: a KD according to (a) and (j), a $K_d$ according to (b) and (k), and a $K_a$ according to (c) and (l); or IV: kinetics according to I and II; or V: kinetics according to I and III; or VI: kinetics according to I, II and III.

The invention also provides a ligand comprising a variant of any preceding aspect or embodiment of the invention. For example, the ligand can be a dual-specific ligand (see WO04003019 for examples of dual-specific ligands). In one aspect, the invention provides a multispecific ligand comprising an anti-SA variant of any preceding aspect or embodiment of the invention and a binding moiety that specifically binds a target antigen other than SA. The binding moiety can be any binding moiety that specifically binds a target, e.g., the moiety is an antibody, antibody fragment, scFv, Fab, dAb or a binding moiety comprising a non-immunoglobulin protein scaffold. Such moieties are disclosed in WO2008/096158 (see examples 17 to 25, which disclosure is incorporated herein by reference). Examples of non-immunoglobulin scaffolds are CTLA-4, lipocallin, staphylococcal protein A (spA), Affibody™, Avimers™, adnectins, GroEL and fibronectin.

In one embodiment, a linker is provided between the anti-target binding moiety and the anti-SA single variant, the linker comprising the amino acid sequence AST, optionally ASTSGPS. Alternative linkers are described in WO2007085814 (incorporated herein by reference), WO2008/096158 (see the passage at page 135, line 12 to page 140, line 14, which disclosure and all sequences of linkers are expressly incorporated herein by reference as though explicitly written herein and for use with the present invention, and it is contemplated that any part of such disclosure can be incorporated into one or more claims herein) and WO2009/068649.

In one embodiment of the multispecific ligand, the target antigen may be, or be part of, polypeptides, proteins or nucleic acids, which may be naturally occurring or synthetic. In this respect, the ligand of the invention may bind the target antigen and act as an antagonist or agonist (e.g., EPO receptor agonist). One skilled in the art will appreciate that the choice is large and varied. They may be for instance, human or animal proteins, cytokines and growth factors, cytokine receptors, where cytokine receptors include receptors for cytokines, enzymes, co-factors for enzymes or DNA binding proteins.

As used herein, the term "antagonist of Tumor Necrosis Factor Receptor 1 (TNFR1)" or "anti-TNFR1 antagonist" or the like refers to an agent (e.g., a molecule, a compound) which binds TNFR1 and can inhibit a (i.e., one or more) function of TNFR1. For example, an antagonist of TNFR1 can inhibit the binding of TNF alpha to TNFR1 and/or inhibit signal transduction mediated through TNFR1. Accordingly, TNFR1-mediated processes and cellular responses (e.g., TNF alpha-induced cell death in a standard L929 cytotoxicity assay) can be inhibited with an antagonist of TNFR1.

In one embodiment, the multispecific ligand comprises an anti-SA dAb variant of the invention and an anti-TNFR1 binding moiety, e.g., an anti-TNFR1 dAb. Optionally, the ligand has only one anti-TNFR1 binding moiety (e.g., dAb) to reduce the chance of receptor cross-linking. Anti-TNFR1 dAbs are described, for example, in WO2006/038027, WO2007/049017, WO2008149148 and WO2010/081787 (the amino acid sequences of which and the nucleotide sequence of which, as disclosed in those PCT applications, are expressly incorporated herein by reference as though explicitly written herein and for use with the present invention, and it is contemplated that any part of such disclosures can be incorporated into one or more claims herein).

In one embodiment, the ligand of the invention is a fusion protein comprising a variant of the invention fused directly or indirectly to one or more polypeptides. For example, the fusion protein can be a "drug fusion" as disclosed in WO2005/118642 (the disclosure of which is incorporated herein by reference), comprising a variant of the invention and a polypeptide drug as defined in that PCT application.

As used herein, "drug" refers to any compound (e.g., small organic molecule, nucleic acid, polypeptide) that can be administered to an individual to produce a beneficial, therapeutic or diagnostic effect through binding to and/or altering the function of a biological target molecule in the individual. The target molecule can be an endogenous target molecule encoded by the individual's genome (e.g. an enzyme, receptor, growth factor, cytokine encoded by the individual's genome) or an exogenous target molecule encoded by the genome of a pathogen (e.g. an enzyme encoded by the genome of a virus, bacterium, fungus, nematode or other pathogen). Suitable drugs for use in fusion proteins and conjugates comprising an anti-SA dAb variant of the invention are disclosed in WO2005/118642 and WO2006/059106 (the entire disclosures of which are incorporated herein by reference, and including the entire list of specific drugs as though this list were expressly written herein, and it is contemplated that such incorporation provides disclosure of specific drugs for inclusion in claims herein). For example, the drug can be glucagon-like peptide 1 (GLP-1) or a variant, interferon alpha 2b or a variant or exendin-4 or a variant.

In one embodiment, the invention provides a drug conjugate as defined and disclosed in WO2005/118642 and WO2006/059106, wherein the conjugate comprises a variant of the invention. In one example, the drug is covalently linked to the variant (e.g., the variant and the drug are expressed as part of a single polypeptide). Alternatively, in an example, the drug is non-covalently bonded or associated with the variant. The drug can be covalently or noncovalently bonded to the variant directly or indirectly (e.g., through a suitable linker and/or noncovalent binding of complementary binding partners (e.g., biotin and avidin)). When complementary binding partners are employed, one of the binding partners can be covalently bonded to the drug directly or through a suitable linker moiety, and the complementary binding partner can be covalently bonded to the variant directly or through a suitable linker moiety. When the drug is a polypeptide or peptide, the drug composition can be a fusion protein, wherein the polypeptide or peptide, drug and the polypeptide binding moiety are discrete parts (moieties) of a continuous polypeptide chain. As described herein, the polypeptide binding moieties and polypeptide drug moieties can be directly bonded to each other through a peptide bond, or linked through a suitable amino acid, or peptide or polypeptide linker.

A ligand which contains one single variable domain (monomer) variant of the invention or more than one single variable domain (multimer, fusion protein, conjugate, and dual specific ligand as defined herein) which specifically binds to serum albumin, can further comprise one or more entities selected from, but preferably not limited to a label, a tag, an additional single variable domain, a dAb, an antibody, an antibody fragment, a marker and a drug. One or more of these entities can be located at either the COOH terminus or at the N terminus or at both the N terminus and the COOH terminus of the ligand comprising the single variable domain, (either immunoglobulin or non-immunoglobulin single variable domain). One or more of these entities can be located at either the COOH terminus, or the N terminus, or both the N terminus and the COOH terminus of the single variable domain which specifically binds serum albumin of the ligand which contains one single variable domain (monomer) or more than one single variable domains (multimer, fusion protein, conjugate, and dual specific ligand as defined herein). Non-limiting examples of tags which can be positioned at one or both of these termini include a HA, his or a myc tag. The entities, including one or more tags, labels and drugs, can be bound to the ligand which contains one single variable domain (monomer) or more than one single variable domain (multimer, fusion protein, conjugate, and dual specific ligand as defined herein), which binds serum albumin, either directly or through linkers as described above.

Also encompassed herein is an isolated nucleic acid encoding any of the variants, fusion proteins, conjugates or ligands described herein, e.g., a ligand which contains one single variable domain (monomer) variant of the invention or more than one single variable domain (e.g., multimer, fusion protein, conjugate, and dual specific ligand as defined herein) variant which specifically binds to serum albumin, or which specifically binds both human serum albumin and at least one non-human serum albumin, or functionally active fragments thereof. Also encompassed herein is a vector and/or an expression vector, a host cell comprising the vector, e.g., a plant or animal cell and/or cell line transformed with a vector, a method of expressing and/or producing one or more variants, fusion proteins or ligands which contains one single variable domain (monomer) variant or more than one single variable domain variants (e.g., multimer, fusion protein, conjugate, and dual specific ligand as defined herein) which specifically binds to serum albumin, or fragment(s) thereof encoded by said vectors, including in some instances culturing the host cell so that the one or more variants, fusion proteins or ligands or fragments thereof are expressed and optionally recovering the ligand which contains one single variable domain (monomer) or more than one single variable domain (e.g., multimer, fusion protein, conjugate, and dual specific ligand as defined herein) which specifically binds to serum albumin, from the host cell culture medium. Also encompassed are methods of contacting a ligand described herein with serum albumin, including serum albumin and/or non-human serum albumin(s), and/or one or more targets other than serum albumin, where the targets include biologically active molecules, and include animal proteins, cytokines as listed above, and include methods where the contacting is in vitro as well as administering any of the variants, fusion proteins or ligands described herein to an individual host animal or cell in vivo and/or ex vivo. Preferably, administering ligands described herein which comprises a single variable domain (immunoglobulin or non-immunoglobulin) directed to serum albumin and/or non-human serum albumin(s), and one or more domains directed to one or more targets other than serum albumin, will increase the half life, including the T beta and/or terminal half life, of the anti-target ligand. Nucleic acid molecules encoding the variants, fusion proteins or single domain containing ligands or fragments thereof, including functional fragments thereof, are contemplated herein. Vectors encoding the nucleic acid molecules, including but preferably not limited to expression vectors, are contemplated herein, as are host cells from a cell line or organism containing one or more of these expression vectors. Also contemplated are methods of producing any variant, fusion protein or ligand, including, but preferably not limited to any of the aforementioned nucleic acids, vectors and host cells.

An aspect of the invention provides a nucleic acid comprising a nucleotide sequence encoding a variant according to the invention or a multispecific ligand of the invention or fusion protein of the invention or a nucleotide sequence that is at least 70, 75, 80, 85, 90, 95, 96, 97, 98 or 99% identical to said selected sequence.

An aspect of the invention provides a vector comprising the nucleic acid of the invention. An aspect of the invention provides an isolated host cell comprising the vector.

Reference is made to WO2008/096158 for details of library vector systems, combining single variable domains, characterization of dual specific ligands, structure of dual specific ligands, scaffolds for use in constructing dual specific ligands, uses of anti-serum albumin dAbs and multispecific ligands and half-life-enhanced ligands, and compositions and formulations of comprising anti-serum albumin dAbs. These disclosures are incorporated herein by reference to provide guidance for use with the present invention, including for variants, ligands, fusion proteins, conjugates, nucleic acids, vectors, hosts and compositions of the present invention.

Sequences

TABLE 1

Amino Acid Sequences of DOM7h-11 Variant dAbs

DOM7h-11-15 (SEQ ID NO: 1)
DIQMTQSPSSLSASVGDRVTITCRASRPIGTMLSWYQQKPGKAPKLLILAFSRLQSGVPSR
FSGSGSGTDFTLTISSLQPEDFATYYCAQAGTHPTTFGQGTKVEIKR

DOM7h-11-3 (SEQ ID NO: 2)
DIQMTQSPSSLSASVGDRVTITCRASRPIGTTLSWYQQKPGKAPKLLILWNSRLQSGVPSR
FSGSGSGTDFTLTISSLQPEDFATYYCAQAGTHPTTFGQGTKVEIKR

DOM7h-11-12 (SEQ ID NO: 157)
DIQMTQSPSSLSASVGDRVTITCRASRPIGTMLSWYQQKPGKAPKLLILFGSRLQSGVP
SRFSGSGSGTDFTLTISSLQPEDFATYYCAQAGTHPTTFGQGTKVEIKR

TABLE 2

Nucleotide Sequences of DOM7h-11 Variant dAbs

DOM7h-11-15 (SEQ ID NO: 3)
GACATCCAGA TGACCCAGTC TCCATCCTCC CTGTCTGCAT CTGTAGGAGA CCGTGT
CACC ATCACTTGCC GGGCAAGTCG TCCGATTGGG ACGATGTTAA GTTGGTACCA G
CAGAAACCA GGGAAAGCCC CTAAGCTCCT GATCCTTGCT TTTTCCCGTT TGCAAAG
TGG GGTCCCATCA CGTTTCAGTG GCAGTGGATC TGGGACAGAT TTCACTCTCA CC
ATCAGCAG TCTGCAACCT GAAGATTTTG CTACGTACTA CTGCGCGCAG GCTGGGA
CGC ATCCTACGAC GTTCGGCCAA GGGACCAAGG TGGAAATCAA ACGG

DOM7h-11-3 (SEQ ID NO: 4)
GACATCCAGA TGACCCAGTC TCCATCCTCC CTGTCTGCAT CTGTAGGAGA CCGTGT
CACC ATCACTTGCC GGGCAAGTCG TCCGATTGGG ACGACGTTAA GTTGGTACCA G
CAGAAACCA GGGAAAGCCC CTAAGCTCCT GATCCTTTGG AATTCCCGTT TGCAAAG
TGG GGTCCCATCA CGTTTCAGTG GCAGTGGATC TGGGACAGAT TTCACTCTCA CC
ATCAGCAG TCTGCAACCT GAAGATTTTG CTACGTACTA CTGTGCGCAG GCTGGGAC
GC ATCCTACGAC GTTCGGCCAA GGGACCAAGG TGGAAATCAA ACGG

DOM7h-11-12 (SEQ ID NO: 158)
GACATCCAGATGACCCAGTCTCCATCCTCCCTGTCTGCATCTGTAGGAGACCGTGTCA
CCATCACTTGCCGGGCAAGTCGTCCGATTGGGACGATGTTAAGTTGGTACCAGCAGA
AACCAGGGAAAGCCCCTAAGCTCCTGATCTTGTTTGGTTCCCGGTTGCAAAGTGGGGT
CCCATCACGTTTCAGTGGCAGTGGATCTGGGACAGATTTCACTCTCACCATCAGCAGT
CTGCAACCTGAAGATTTTGCTACGTACTACTGTGCGCAGGCTGGGACGCATCCTACGA
CGTTCGGCCAAGGGACCAAGGTGGAAATCAAACGG

TABLE 5

Anti-serum albumin dAb (DOM7h) fusions

(used in Rat studies):-
DOM7h-14/Exendin-4 fusion DMS number 7138
Amino acid sequence (SEQ ID NO: 5)
HGEGTFTSDLSKQMEEEAVRLFIEWLKNGGPSSGAPPPSGGGGSGGGGSGGGGSDIQ
MTQSPSSLSASVGDRVTITCRASQWIGSQLSWYQQKPGKAPKLLIMWRSSLQSGVPSRF
SGSGSGTDFTLTISSLQPEDFATYYCAQGAALPRTFGQGTKVEIKR Nucleotide sequence (SEQ ID NO: 6)
CATGGTGAAGGAACATTTACCAGTGACTTGTCAAAACAGATGGAAGAGGAGGCAGTG
CGGTTATTTATTGAGTGGCTTAAGAACGGAGGACCAAGTAGCGGGGCACCTCCGCCA
TCGGGTGGTGGAGGCGGTTCAGGCGGAGGTGGCAGCGGCGGTGGCGGGTCGGACA
TCCAGATGACCCAGTCTCCATCCTCCCTGTCTGCATCTGTAGGAGACCGTGTCACCAT
CACTTGCCGGGCAAGTCAGTGGATTGGGTCTCAGTTATCTTGGTACCAGCAGAAACCA
GGGAAAGCCCCTAAGCTCCTGATCATGTGGCGTTCCTCGTTGCAAAGTGGGGTCCCA
TCACGTTTCAGTGGCAGTGGATCTGGGACAGATTTCACTCTCACCATCAGCAGTCTGC
AACCTGAAGATTTTGCTACGTACTACTGTGCTCAGGGTGCGGCGTTGCCTAGGACGTT
CGGCCAAGGGACCAAGGTGGAAATCAAACGG DOM7h-14-10/Exendin-4 fusion DMS number 7139
Amino acid sequence (SEQ ID NO: 7)
HGEGTFTSDLSKQMEEEAVRLFIEWLKNGGPSSGAPPPSGGGGSGGGGSGGGGSDIQ
MTQSPSSLSASVGDRVTITCRASQWIGSQLSWYQQKPGKAPKLLIMWRSSLQSGVPSRF
SGSGSGTDFTLTISSLQPEDFATYYCAQGLRHPKTFGQGTKVEIKR TABLE 5-continued Anti-serum albumin dAb (DOM7h) fusions Nucleotide sequence (SEQ ID NO: 8)
CATGGTGAAGGAACATTTACCAGTGACTTGTCAAAACAGATGGAAGAGGAGGCAGTG
CGGTTATTTATTGAGTGGCTTAAGAACGGAGGACCAAGTAGCGGGGCACCTCCGCCA
TCGGGTGGTGGAGGCGGTTCAGGCGGAGGTGGCAGCGGCGGTGGCGGGTCGGACA
TCCAGATGACCCAGTCTCCATCCTCCCTGTCTGCATCTGTAGGAGACCGTGTCACCAT
CACTTGCCGGGCAAGTCAGTGGATTGGGTCTCAGTTATCTTGGTACCAGCAGAAACCA
GGGAAAGCCCCTAAGCTCCTGATCATGTGGCGTTCCTCGTTGCAAAGTGGGGTCCCA
TCACGTTTCAGTGGCAGTGGATCTGGGACAGATTTCACTCTCACCATCAGCAGTCTGC
AACCTGAAGATTTTGCTACGTACTACTGTGCTCAGGGTTTGAGGCATCCTAAGACGTT
CGGCCAAGGGACCAAGGTGGAAATCAAACGG DOM7h-11/Exendin-4 fusion DMS number 7142
Amino acid sequence (SEQ ID NO: 9)
HGEGTFTSDLSKQMEEEAVRLFIEWLKNGGPSSGAPPPSGGGGSGGGGSGGGGSDIQ
MTQSPSSLSASVGDRVTITCRASRPIGTTLSWYQQKPGKAPKLLIWFGSRLQSGVPSRFS
GSGSGTDFTLTISSLQPEDFATYYCAQAGTHPTTFGQGTKVEIKR Nucleotide sequence (SEQ ID NO: 10)
CATGGTGAAGGAACATTTACCAGTGACTTGTCAAAACAGATGGAAGAGGAGGCAGTG
CGGTTATTTATTGAGTGGCTTAAGAACGGAGGACCAAGTAGCGGGGCACCTCCGCCA
TCGGGTGGTGGAGGCGGTTCAGGCGGAGGTGGCAGCGGCGGTGGCGGGTCGGACA
TCCAGATGACCCAGTCTCCATCCTCCCTGTCTGCATCTGTAGGAGACCGTGTCACCAT
CACTTGCCGGGCAAGTCGTCCGATTGGGACGACGTTAAGTTGGTACCAGCAGAAACC
AGGGAAAGCCCCTAAGCTCCTGATCTGGTTTGGTTCCCGGTTGCAAAGTGGGGTCCC
ATCACGTTTCAGTGGCAGTGGATCTGGGACAGATTTCACTCTCACCATCAGCAGTCTG
CAACCTGAAGATTTTGCTACGTACTACTGTGCGCAGGCTGGGACGCATCCTACGACGT
TCGGCCAAGGGACCAAGGTGGAAATCAAACGG DOM7h-11-15/Exendin-4 fusion DMS number 7143
Amino acid sequence (SEQ ID NO: 11)
HGEGTFTSDLSKQMEEEAVRLFIEWLKNGGPSSGAPPPSGGGGSGGGGSGGGGSDIQ
MTQSPSSLSASVGDRVTITCRASRPIGTMLSWYQQKPGKAPKLLILAFSRLQSGVPSRFS
GSGSGTDFTLTISSLQPEDFATYYCAQAGTHPTTFGQGTKVEIKR Nucleotide sequence (SEQ ID NO: 12)
CATGGTGAAGGAACATTTACCAGTGACTTGTCAAAACAGATGGAAGAGGAGGCAGTG
CGGTTATTTATTGAGTGGCTTAAGAACGGAGGACCAAGTAGCGGGGCACCTCCGCCA
TCGGGTGGTGGAGGCGGTTCAGGCGGAGGTGGCAGCGGCGGTGGCGGGTCGGACA
TCCAGATGACCCAGTCTCCATCCTCCCTGTCTGCATCTGTAGGAGACCGTGTCACCAT
CACTTGCCGGGCAAGTCGTCCGATTGGGACGATGTTAAGTTGGTACCAGCAGAAACC
AGGGAAAGCCCCTAAGCTCCTGATCCTTGCTTTTTCCCGTTTGCAAAGTGGGGTCCCA
TCACGTTTCAGTGGCAGTGGATCTGGGACAGATTTCACTCTCACCATCAGCAGTCTGC
AACCTGAAGATTTTGCTACGTACTACTGCGCGCAGGCTGGGACGCATCCTACGACGTT
CGGCCAAGGGACCAAGGTGGAAATCAAACGG DOM7h14-10/ G4SC-NCE fusion
Amino acid sequence (SEQ ID NO: 13) encoding DOM7h14-10/G4SC
DIQMTQSPSSLSASVGDRVTITCRASQWIGSQLSWYQQKPGKAPKLLIMWRSSLQSGVPS
RFSGSGSGTDFTLTISSLQPEDFATYYCAQGLRHPKTFGQGTKVEIKRGGGGSC The C-terminal cysteine can be linked to a new chemical entity
(pharmaceutical chemical compound, NCE), eg using maleimide linkage.

Nucleotide sequence (SEQ ID NO: 14) encoding DOM7h14-10/G4SC
GACATCCAGATGACCCAGTCTCCATCCTCCCTGTCTGCATCTGTAGGAGACCGTGTCA
CCATCACTTGCCGGGCAAGTCAGTGGATTGGGTCTCAGTTATCTTGGTACCAGCAGAA
ACCAGGGAAAGCCCCTAAGCTCCTGATCATGTGGCGTTCCTCGTTGCAAAGTGGGGT
CCCATCACGTTTCAGTGGCAGTGGATCTGGGACAGATTTCACTCTCACCATCAGCAGT
CTGCAACCTGAAGATTTTGCTACGTACTACTGTGCTCAGGGTTTGAGGCATCCTAAGA
CGTTCGGCCAAGGGACCAAGGTGGAAATCAAACGGGGTGGCGGAGGGGGTTCCTGT DOM7h14-10/TVAAPSC fusion
Amino acid sequence (SEQ ID NO: 15)
DIQMTQSPSSLSASVGDRVTITCRASQWIGSQLSWYQQKPGKAPKLLIMWRSSLQSGVPS
RFSGSGSGTDFTLTISSLQPEDFATYYCAQGLRHPKTFGQGTKVEIKRTVAAPSC The C-terminal cysteine can be linked to a new chemical entity
(pharmaceutical chemical compound, NCE), eg using maleimide linkage.

Nucleotide sequence (SEQ ID NO: 16)
GACATCCAGATGACCCAGTCTCCATCCTCCCTGTCTGCATCTGTAGGAGACCGTGTCA
CCATCACTTGCCGGGCAAGTCAGTGGATTGGGTCTCAGTTATCTTGGTACCAGCAGAA
ACCAGGGAAAGCCCCTAAGCTCCTGATCATGTGGCGTTCCTCGTTGCAAAGTGGGGT
CCCATCACGTTTCAGTGGCAGTGGATCTGGGACAGATTTCACTCTCACCATCAGCAGT

TABLE 5-continued

Anti-serum albumin dAb (DOM7h) fusions

```
CTGCAACCTGAAGATTTTGCTACGTACTACTGTGCTCAGGGTTTGAGGCATCCTAAGA
CGTTCGGCCAAGGGACCAAGGTGGAAATCAAACGGACCGTCGCTGCTCCATCTTGT (used in mouse studies):-
DOM7h-11/DOM1m-21-23 fusion DMS number 5515
Amino acid sequence (SEQ ID NO: 17)
EVQLLESGGGLVQPGGSLRLSCAASGFTFNRYSMGWLRQAPGKGLEWVSRIDSYGRGT
YYEDPVKGRFSISRDNSKNTLYLQMNSLRAEDTAVYYCAKISQFGSNAFDYWGQGTQVT
VSSASTSGPSDIQMTQSPSSLSASVGDRVTITCRASRPIGTTLSWYQQKPGKAPKLLIWFG
SRLQSGVPSRFSGSGSGTDFTLTISSLQPEDFATYYCAQAGTHPTTFGQGTKVEIKR Amino acid plus myc tag sequence (SEQ ID NO: 18)
EVQLLESGGGLVQPGGSLRLSCAASGFTFNRYSMGWLRQAPGKGLEWVSRIDSYGRGT
YYEDPVKGRFSISRDNSKNTLYLQMNSLRAEDTAVYYCAKISQFGSNAFDYWGQGTQVT
VSSASTSGPSDIQMTQSPSSLSASVGDRVTITCRASRPIGTTLSWYQQKPGKAPKLLIWFG
SRLQSGVPSRFSGSGSGTDFTLTISSLQPEDFATYYCAQAGTHPTTFGQGTKVEIKRAAA
EQKLISEEDLN Nucleotide sequence (SEQ ID NO: 19)
GAGGTGCAGCTGTTGGAGTCTGGGGGAGGCTTGGTACAGCCTGGGGGGTCCCTGCG
TCTCTCCTGTGCAGCCTCCGGATTCACCTTTAATAGGTATAGTATGGGGTGGCTCCGC
CAGGGCTCCAGGGAAGGGTCTAGAGTGGGTCTCACGGATTGATTCTTATGGTCGTGGT
ACATACTACGAAGACCCCGTGAAGGGCCGGTTCAGCATCTCCCGCGACAATTCCAAG
AACACGCTGTATCTGCAAATGAACAGCCTGCGTGCCGAGGACACCGCCGTATATTACT
GTGCGAAAATTTCTCAGTTTGGGTCAAATGCGTTTGACTACTGGGGTCAGGGAACCCA
GGTCACCGTCTCGAGCGCTAGCACCAGTGGTCCATCGGACATCCAGATGACCCAGTC
TCCATCCTCCCTGTCTGCATCTGTAGGAGACCGTGTCACCATCACTTGCCGGGCAAGT
CGTCCGATTGGGACGACGTTAAGTTGGTACCAGCAGAAACCAGGGAAAGCCCCTAAG
CTCCTGATCTGGTTTGGTTCCCGGTTGCAAAGTGGGGTCCCATCACGTTTCAGTGGCA
GTGGATCTGGGACAGATTTCACTCTCACCATCAGCAGTCTGCAACCTGAAGATTTTGC
TACGTACTACTGTGCGCAGGCTGGACGCATCCTACGACGTTCGGCCAAGGGACCAA
GGTGGAAATCAAACGG Nucleotide plus myc tag sequence (SEQ ID NO: 20)
GAGGTGCAGCTGTTGGAGTCTGGGGGAGGCTTGGTACAGCCTGGGGGGTCCCTGCG
TCTCTCCTGTGCAGCCTCCGGATTCACCTTTAATAGGTATAGTATGGGGTGGCTCCGC
CAGGGCTCCAGGGAAGGGTCTAGAGTGGGTCTCACGGATTGATTCTTATGGTCGTGGT
ACATACTACGAAGACCCCGTGAAGGGCCGGTTCAGCATCTCCCGCGACAATTCCAAG
AACACGCTGTATCTGCAAATGAACAGCCTGCGTGCCGAGGACACCGCCGTATATTACT
GTGCGAAAATTTCTCAGTTTGGGTCAAATGCGTTTGACTACTGGGGTCAGGGAACCCA
GGTCACCGTCTCGAGCGCTAGCACCAGTGGTCCATCGGACATCCAGATGACCCAGTC
TCCATCCTCCCTGTCTGCATCTGTAGGAGACCGTGTCACCATCACTTGCCGGGCAAGT
CGTCCGATTGGGACGACGTTAAGTTGGTACCAGCAGAAACCAGGGAAAGCCCCTAAG
CTCCTGATCTGGTTTGGTTCCCGGTTGCAAAGTGGGGTCCCATCACGTTTCAGTGGCA
GTGGATCTGGGACAGATTTCACTCTCACCATCAGCAGTCTGCAACCTGAAGATTTTGC
TACGTACTACTGTGCGCAGGCTGGACGCATCCTACGACGTTCGGCCAAGGGACCAA
GGTGGAAATCAAACGGGCGGCCGCAGAACAAAAACTCATCTCAGAAGAGGATCTGAA
TTAA DOM7h-11-15/DOM1m-21-23 fusion DMS number 5517
Amino acid sequence (SEQ ID NO: 21)
EVQLLESGGGLVQPGGSLRLSCAASGFTFNRYSMGWLRQAPGKGLEWVSRIDSYGRGT
YYEDPVKGRFSISRDNSKNTLYLQMNSLRAEDTAVYYCAKISQFGSNAFDYWGQGTQVT
VSSASTSGPSDIQMTQSPSSLSASVGDRVTITCRASRPIGTMLSWYQQKPGKAPKLLILAF
SRLQSGVPSRFSGSGSGTDFTLTISSLQPEDFATYYCAQAGTHPTTFGQGTKVEIKR Amino acid plus nucleotide plus myc tag sequence (SEQ ID NO: 22)
EVQLLESGGGLVQPGGSLRLSCAASGFTFNRYSMGWLRQAPGKGLEWVSRIDSYGRGT
YYEDPVKGRFSISRDNSKNTLYLQMNSLRAEDTAVYYCAKISQFGSNAFDYWGQGTQVT
VSSASTSGPSDIQMTQSPSSLSASVGDRVTITCRASRPIGTMLSWYQQKPGKAPKLLILAF
SRLQSGVPSRFSGSGSGTDFTLTISSLQPEDFATYYCAQAGTHPTTFGQGTKVEIKRAAA
EQKLISEEDLN Nucleotide sequence (SEQ ID NO: 23)
GAGGTGCAGCTGTTGGAGTCTGGGGGAGGCTTGGTACAGCCTGGGGGGTCCCTGCG
TCTCTCCTGTGCAGCCTCCGGATTCACCTTTAATAGGTATAGTATGGGGTGGCTCCGC
CAGGGCTCCAGGGAAGGGTCTAGAGTGGGTCTCACGGATTGATTCTTATGGTCGTGGT
ACATACTACGAAGACCCCGTGAAGGGCCGGTTCAGCATCTCCCGCGACAATTCCAAG
AACACGCTGTATCTGCAAATGAACAGCCTGCGTGCCGAGGACACCGCCGTATATTACT
GTGCGAAAATTTCTCAGTTTGGGTCAAATGCGTTTGACTACTGGGGTCAGGGAACCCA
GGTCACCGTCTCGAGCGCTAGCACCAGTGGTCCATCGGACATCCAGATGACCCAGTC
TCCATCCTCCCTGTCTGCATCTGTAGGAGACCGTGTCACCATCACTTGCCGGGCAAGT
CGTCCGATTGGGACGATGTTAAGTTGGTACCAGCAGAAACCAGGGAAAGCCCCTAAG
CTCCTGATCCTTGCTTTTTCCCGTTTGCAAAGTGGGGTCCCATCACGTTTCAGTGGCA
GTGGATCTGGGACAGATTTCACTCTCACCATCAGCAGTCTGCAACCTGAAGATTTTGC
TACGTACTACTGCGCGCAGGCTGGACGCATCCTACGACGTTCGGCCAAGGGACCAA
GGTGGAAATCAAACGG
```

TABLE 5-continued

Anti-serum albumin dAb (DOM7h) fusions

Nucleotide plus myc tag sequence (SEQ ID NO: 24)
GAGGTGCAGCTGTTGGAGTCTGGGGGAGGCTTGGTACAGCCTGGGGGGTCCCTGCG
TCTCTCCTGTGCAGCCTCCGGATTCACCTTTAATAGGTATAGTATGGGGTGGCTCCGC
CAGGCTCCAGGGAAGGGTCTAGAGTGGGTCTCACGGATTGATTCTTATGGTCGTGGT
ACATACTACGAAGACCCCGTGAAGGGCCGGTTCAGCATCTCCCGCGACAATTCCAAG
AACACGCTGTATCTGCAAATGAACAGCCTGCGTGCCGAGGACACCGCCGTATATTACT
GTGCGAAAATTTCTCAGTTTGGGTCAAATGCGTTTGACTACTGGGGTCAGGGAACCCA
GGTCACCGTCTCGAGCGCTAGCACCAGTGGTCCATCGGACATCCAGATGACCCAGTC
TCCATCCTCCCTGTCTGCATCTGTAGGAGACCGTGTCACCATCACTTGCCGGGCAAGT
CGTCCGATTGGGACGATGTTAAGTTGGTACCAGCAGAAACCAGGGAAAGCCCCTAAG
CTCCTGATCCTTGCTTTTTCCCGTTTGCAAAGTGGGGTCCCATCACGTTTCAGTGGCA
GTGGATCTGGGACAGATTTCACTCTCACCATCAGCAGTCTGCAACCTGAAGATTTTGC
TACGTACTACTGCGCGCAGGCTGGGACGCATCCTACGACGTTCGGCCAAGGGACCAA
GGTGGAAATCAAACGGGCGGCCGCAGAACAAAAACTCATCTCAGAAGAGGATCTGAA
TTAA Where a myc-tagged molecule is indicated in this table, this was the version used in PK studies in the examples. Where no myc-tagged sequences are given, the PK studies in the examples were not done with myc-tagged material, ie, the studies were done with the non-tagged constructs shown.

EXEMPLIFICATION

All numbering in the experimental section is according to Kabat (Kabat, E. A. National Institutes of Health (US) & Columbia University. Sequences of proteins of immunological interest, edn 5 (US Dept. Of Health and Human Services Public Health Service, National Institutes of Health, Bethesda, Md., 1991)).

Derivation of DOM7h-11, DOM7h-14 and DOM7r variants is described.

Example 1

Vk Affinity Maturation

Selections:
HSA (Human Serum Albumin) and RSA (Rat Serum Albumin) antigens were obtained from Sigma (essentially fatty acid free, ~99% (agarose gel electrophoresis), lyophilized powder Cat. No. A3782 and A6414 respectively)

Biotinylated products of above two antigens were made by using EZ Link Sulfo-NHS-SS-Biotin (Pierce, Cat. No. 21331). Free biotin reagent was removed by passing the samples twice through PD10 desalting column followed by overnight dialysis against 1000× excess volume of PBS at 4° C. Resulting product was tested by mass spec and 1-2 biotins per molecule were observed.

Affinity Maturation Libraries:
Both error-prone and CDR libraries were created using DOM7h-11 and DOM7h-14 parental dAbs (see WO2008/096158 for the sequences of DOM7h-11 and DOM7h-14). The CDR libraries were generated in the pDOM4 vector and the error prone libraries were generated in the pDOM33 vector (to allow for selection with or without protease treatment). Vector pDOM4, is a derivative of the Fd phage vector in which the gene III signal peptide sequence is replaced with the yeast glycolipid anchored surface protein (GAS) signal peptide. It also contains a c-myc tag between the leader sequence and gene III, which puts the gene III back in frame. This leader sequence functions well both in phage display vectors but also in other prokaryotic expression vectors and can be universally used. pDOM33 is a modified version of the pDOM4 vector where the c-myc tag has been removed which renders the dAb-phage fusion resistant to the protease trypsin. This allows the use of trypsin within the phage selection to select for dAbs that are more protease stable (see WO2008149143).

For error-prone maturation libraries, plasmid DNA encoding the dAb to be matured was amplified by PCR, using the GENEMORPH® II RANDOM MUTAGENESIS KIT (random, unique mutagenesis kit, Stratagene). The product was digested with Sal I and Not I and used in a ligation reaction with cut phage vector pDOM33. For the CDR libraries, PCR reactions were performed using degenerate oligonucleotides containing NNK or NNS codons to diversify the required positions in the dAb to be affinity matured. Assembly PCR was then used to generate a full length diversified insert. The insert was digested with Sal I and Not I and used in a ligation reaction with pDOM4 for mutagenesis of multiple residues and pDOM5 for mutagenesis of single residues. The pDOM5 vector is a pUC119-based expression vector where protein expression is driven by the LacZ promoter. A GAS1 leader sequence (see WO 2005/093074) ensures secretion of isolated, soluble dAbs into the periplasm and culture supernatant of E. coli. dAbs are cloned SalI/NotI in this vector, which appends a myc tag at the C-terminus of the dAb. This protocol using SalI and Not I results in inclusion of an ST amino acid sequence at the N-terminus.

The ligation produced by either method was then used to transform E. coli strain TB1 by electroporation and the transformed cells plated on 2×TY agar containing 15 µg/ml tetracycline, yielding library sizes of >5×10$^7$ clones.

The error-prone libraries had the following average mutation rate and size: DOM7h-11 (2.5 mutations per dAb), size: 6.1×10$^8$, DOM7h-14 (2.9 mutations per dAb), size: 5.4×10$^8$.

Each CDR library has four amino acid diversity. Two libraries were generated for each of CDRs 1 and 3, and one library for CDR2. The positions diversified within each library are as follows (amino acids based on VK dummy DPK9 sequence):

| | Library size | |
|---|---|---|
| | DOM7h-11 | DOM7h-14 |
| 1—Q27, S28, S30, S31 (CDR1) | 8.8 × 10$^7$ | 5.8 × 10$^7$ |
| 2—S30, S31, Y32, N34 (CDR1) | 4.6 × 10$^8$ | 4.2 × 10$^8$ |
| 3—Y49, A50, A51, S53 (CDR2) | 3.9 × 10$^8$ | 2.4 × 10$^8$ |
| 4—Q89, S91, Y92, S93 (CDR3) | 1.8 × 10$^8$ | 2.5 × 10$^8$ |
| 5—Y92, Y93, T94, N96 (CDR3) | 4.0 × 10$^8$ | 3.3 × 10$^8$ |

Example 2

Selection Strategies

Three phage selection strategies were adopted for Vκ AlbudAb™ (anti-serum albumin dAb) affinity maturation:
1) Selections against HSA only:
Three rounds of selection against HSA were carried out. The error prone libraries and each CDR library were selected as an individual pool in all rounds. The first round of selection was performed against HSA passively coated onto an immunotube at 1 mg/ml. Round 2 was performed against 100 nM HSA and round 3 against 10 nM (CDR selections) or 20 or 100 nM (Error prone selections) HSA, both as soluble selections followed by a fourth round of selection with the error prone libraries against 1.5 nM HSA as a soluble selection. The error prone libraries were eluted with 0.1 M glycine pH 2.0 before neutralisation with 1M Tris pH 8.0 and the CDR libraries were eluted with 1 mg/ml trypsin before infection into log phase TG1 cells. The third round of each selection was subcloned into pDOM5 for screening. Soluble selections used biotinylated HSA.
2) Trypsin selections against HSA:
In order to select dAbs with increased protease resistance compared to the parental clone and with potentially improved biophysical properties, trypsin was used in phage selections (see WO2008149143). Four rounds of selection were preformed against HSA. The first round of selection of error prone libraries was performed against passively coated HSA at 1 mg/ml without trypsin; the second round against passively coated HSA at 1 mg/ml with 20 μg/ml trypsin for 1 hour at 37° C.; the third round selection was performed by soluble selection using biotinylated HSA against 100 nM HSA with 20 μg/ml or 100 μg/ml trypsin for 1 hour at 37° C. The final round of selection was performed by soluble selection using biotinylated HSA against 100 nM HSA with 100 μg/ml trypsin overnight at 37° C.
3) Cross-over selections against HSA (round 1) and RSA (rounds 2-4):
The first round selection was carried out against 1 mg/ml passively coated HSA or 1 μM HSA (soluble selection), followed by a further three rounds of soluble selections against biotinylated RSA at concentrations of 1 μM for round 1, 100 nm for round 2 and 20 nM, 10 nM or 1 nM for round 3.

Screening Strategy and Affinity Determination:

In each case after selection a pool of phage DNA from the appropriate round of selection is prepared using a QIAfilter midiprep kit (Qiagen), the DNA is digested using the restriction enzymes Sal1 and Not1 and the enriched V genes are ligated into the corresponding sites in pDOM5 the soluble expression vector which expresses the dAb with a myc tag (see PCT/EP2008/067789). The ligated DNA is used to electro-transform $E.\ coli$ HB 2151 cells which are then grown overnight on agar plates containing the antibiotic carbenicillin. The resulting colonies are individually assessed for antigen binding. In each case at least 96 clones were tested for binding to HSA, CSA (Cynomolgus monkey Serum Albumin), MSA (mouse serum albumin) and RSA by BIAcore™ (surface plasmon resonance). MSA antigen was obtained from Sigma (essentially fatty acid free, ~99% (agarose gel electrophoresis), lyophilized powder Cat. No. A3559) and CSA was purified from Cynomolgus serum albumin using prometic blue resin (Amersham). Soluble dAb fragments were produced in bacterial culture in ONEX culture media (Novagen) overnight at 37° C. in 96 well plates. The culture supernatant containing soluble dAb was centrifuged and analysed by BIAcore for binding to high density HSA, CSA, MSA and RSA CM5 chips. Clones were found to bind to all these species of serum albumin by off-rate screening. The clones were sequenced revealing unique dAb sequences.

DOM7h11-15 had 96.3% identity to parent (at the amino acid level). DOM7h-11-3 had 97.2% identity to parent (at the amino acid level).

DOM7h-14-10 had 96.3% identity to parent (at the amino acid level).

dAbs were expressed as bacterial supernatants in 2.5 L shake flasks in Onex media at 30° C. for 48 hrs at 250 rpm. dAbs were purified from the culture media by absorption to protein L agarose followed by elution with 10 mM glycine pH2.0. Binding to HSA, CSA, MSA and RSA by BIAcore was confirmed using purified protein at 3 concentrations 1 μM, 500 nM and 50 nM. To determine the binding affinity ($K_D$) of the AlbudAbs to each serum albumin; purified dAbs were analysed by BIAcore over albumin concentration range from 5000 nM to 39 nM (5000 nM, 2500 nM, 1250 nM, 625 nM, 312 nM, 156 nM, 78 nM, 39 nM).

TABLE 6

| AlbudAb | Affinity ($K_D$) to SA (nM) | Kd | Ka |
|---|---|---|---|
| Rat | | | |
| DOM7h-14 | 60 | 2.095E−01 | 4.00E+06 |
| DOM7h-14-10 | 4 | 9.640E−03 | 4.57E+06 |
| DOM 7h-11 | 2100 | 1.00E−01 | 4.80E+04 |
| DOM 7h-11-3 | 10000 (88000) | (7.18e−1) | (8.11e3) |
| DOM 7h-11-15 | 20 | 2.10E−02 | 1.10E+06 |
| Cyno | | | |
| DOM 7h-14 | 66 | 9.65E−02 | 1.50E+06 |
| DOM 7h-14-10 | 9 | 1.15E−02 | 1.60E+06 |
| DOM 7h-11 | 1000 | 6.82E−01 | 8.00E+05 |
| DOM 7h-11-3 | 670 (200) | 9.6E−02 (1.5e−1) | 2.90E+05 (7.26e5) |
| DOM 7h-11-15 | 3 | 5.57E−03 | 5.80E+06 |
| Mouse | | | |
| DOM 7h-14 | 12 | 4.82E−02 | 4.10E+06 |
| DOM 7h-14-10 | 30 | 3.41E−02 | 1.29E+06 |
| DOM 7h-11 | 5000 | 9.00E−01 | |
| DOM 7h-11-3 | ≥10000 (36000) | (6.12e−1) | (1.67e4) |
| DOM 7h-11-15 | 10 | 9.40E−03 | 1.10E+06 |
| Human | | | |
| DOM 7h-14 | 33 | 4.17E−02 | 1.43E+06 |
| DOM 7h-14-10 | 12 | 1.39E−02 | 1.50E+06 |
| DOM 7h-11 | 2800 | 6.41E−01 | 7.00E+05 |
| DOM 7h-11-3 | 32 (130) | 1.6E−02 (2.35e−2) | 6.50E+05 (1.86e5) |
| DOM 7h-11-15 | 1 | 1.84E−03 | 2.00E+06 |

*: values in brackets were derived from a second, independent SPR experiment.

All DOM7h-14 derived variants are cross-reactive to mouse, rat, human and cyno serum albumin. DOM7h-14-10 has improved affinity to rat, cyno and human serum albumin compared to parent.

DOM7h-11-3 has improved affinity to CSA and HSA. DOM7h-11-15 has improved affinity to RSA, MSA, CSA and HSA.

Example 3

Origins of Key DOM7h-11 Lineage Clones

DOM7h-11-3: From affinity maturation performed against HSA using the CDR2 library (Y49, A50, A51, S53), round 3 output 10 nM HSA DOM7h-11-15: From cross-over selections performed against HSA as round 1 followed by additional 3 rounds of selections against RSA using the CDR2 library (Y49, A50, A51, S53) at round 3 selection with 1 nM of RSA.

TABLE 7

CDR sequences (according to Kabat; ref. as above)

| AlbudAb | CDR1 | CDR2 | CDR3 |
|---|---|---|---|
| DPK9 Vk dummy | SQSISSYLN (SEQ ID NO: 25) | YAASSLQS (SEQ ID NO: 26) | QQSYSTPNT (SEQ ID NO: 27) |
| DOM7h-11 | SRPIGTTLS (SEQ ID NO: 28) | WFGSRLQS (SEQ ID NO: 29) | AQAGTHPTT (SEQ ID NO: 30) |
| DOM 7h-11-15 | SRPIGTMLS (SEQ ID NO: 31) | LAFSRLQS (SEQ ID NO: 32) | AQAGTHPTT (SEQ ID NO: 33) |
| DOM 7h-11-3 | SRPIGTTLS (SEQ ID NO: 34) | LWFSRLQS (SEQ ID NO: 35) | AQAGTHPTT (SEQ ID NO: 36) |

Example 4

Origins of Key DOM7h-14 Lineage Clones

DOM7h-14-10: From affinity maturation performed against HSA using CDR3 library (Y92, Y93, T94, N96), round 3 output.

TABLE 8

CDR sequences (according to Kabat; ref. as above)

| AlbudAb | CDR1 | CDR2 | CDR3 |
|---|---|---|---|
| DOM 7h-14 | SQWIGSQLS (SEQ ID NO: 37) | MWRSSLQS (SEQ ID NO: 38) | AQGAALPRT (SEQ ID NO: 39) |
| DOM 7h-14-10 | SQWIGSQLS (SEQ ID NO: 40) | MWRSSLQS (SEQ ID NO: 41) | AQGLRHPKT (SEQ ID NO: 42) |

Example 5

Expression and Biophysical Characterisation

The routine bacterial expression level in 2.5 L shake flasks was determined following culture in Onex media at 30° C. for 48 hrs at 250 rpm. The biophysical characteristics were determined by SEC MALLS and DSC.

SEC MALLS (size exclusion chromatography with multi-angle-LASER-light-scattering) is a non-invasive technique for the characterizing of macromolecules in solution. Briefly, proteins (at concentration of 1 mg/mL in buffer Dulbecco's PBS at 0.5 ml/min are separated according to their hydrodynamic properties by size exclusion chromatography (column: TSK3000 from TOSOH Biosciences; S200 from Pharmacia). Following separation, the propensity of the protein to scatter light is measured using a multi-angle-LASER-light-scattering (MALLS) detector. The intensity of the scattered light while protein passes through the detector is measured as a function of angle. This measurement taken together with the protein concentration determined using the refractive index (RI) detector allows calculation of the molar mass using appropriate equations (integral part of the analysis software Astra v.5.3.4.12).

DSC (Differential Scanning calorimetry): briefly, the protein is heated at a constant rate of 180° C./hrs (at 1 mg/mL in PBS) and a detectable heat change associated with thermal denaturation measured. The transition midpoint ($_{app}T_m$) is determined, which is described as the temperature where 50% of the protein is in its native conformation and the other 50% is denatured. Here, DSC determined the apparent transition midpoint (appTm) as most of the proteins examined do not fully refold. The higher the Tm, the more stable the molecule. Unfolding curves were analysed by non-2-state equations. The software package used was Origin$^R$ v7.0383.

TABLE 9

| AlbudAb | Biophysical parameters | |
|---|---|---|
| | SEC MALLS | DSC Tm (° C.) |
| DOM7h-14 | M | 60 |
| DOM 7h-14-10 | M | 59 |
| DOM 7h-11 | M | 66.9-72.2 |
| DOM 7h-11-3 | M (95%)* | 66.6/70.5 |
| DOM 7h-11-15 | M (<5% D) | 58.5-60.5 |

*in one other trial, monomer was primarily seen by SEC MALLS, although lower than 95%

We observed expression levels for all clones in Table 9 in the range from 15 to 119 mg/L in *E. coli*.

For DOM7h-14 and DOM7h-11 variants, favorable biophysical parameters (monomeric in solution as determined by SEC MALLs and appTm of >55° C. as determined by DSC) and expression levels were maintained during affinity maturation. Monomeric state is advantageous because it avoids dimerisation and the risk of products that may cross-link targets such as cell-surface receptors.

Example 6

Determination of Serum Half Life in Rat, Mouse and Cynomolgus Monkey

AlbudAbs DOM7h-14-10, DOM7h-11 and DOM7h-11-15 were cloned into the pDOM5 vector. For each AlbudAb™, 20-50 mg quantities were expressed in *E. coli* and purified from bacterial culture supernatant using protein L affinity resin and eluted with 100 mM glycine pH2. The proteins were concentrated to greater than 1 mg/ml, buffer exchanged into PBS and endotoxin depleted using Q spin columns (Vivascience). For Rat pharmacokinetic (PK) analysis, AlbudAbs were dosed as single i.v injections at 2.5 mg/kg using 3 rats per compound. Serum samples were taken at 0.16, 1, 4, 12, 24, 48, 72, 120, 168 hrs. Analysis of serum levels was by anti-myc ELISA as per the method described below.

For Mouse PK, DOM7h-11 and DOM7h-11-15 were dosed as single i.v injections at 2.5 mg/kg per dose group of 3 subjects and serum samples taken at 10 mins; 1 h; 8 h; 24 h; 48 h; 72 h; 96 h. Analysis of serum levels was by anti-myc ELISA as per the method described below.

For Cynomolgus monkey PK DOM7h-14-10 and DOM7h-11-15 were dosed as single i.v injections at 2.5 mg/kg into 3 female Cynomolgus monkeys per dose group and serum samples taken at 0.083, 0.25, 0.5, 1, 2, 4, 8, 24, 48, 96, 144, 192, 288, 336, 504 hrs. Analysis of serum levels was by anti-myc ELISA as per the method described below.

Anti-myc ELISA Method

The AlbudAb concentration in serum was measured by anti-myc ELISA. Briefly, goat anti-myc polyclonal antibody (1:500; Abcam, catalogue number ab9132) was coated overnight onto Nunc 96-well Maxisorp plates and blocked with 5% BSA/PBS+1% Tween. Serum samples were added at a range of dilutions alongside a standard at known concentrations. Bound myc-tagged AlbudAb was then detected using a rabbit polyclonal anti-Vk (1:1000; in-house reagent, bleeds were pooled and protein A purified before use) followed by an anti-rabbit IgG HRP antibody (1:10,000; Sigma, catalogue number A2074). Plates were washed between each stage of the assay with 3×PBS+0.1% Tween20 followed by 3×PBS. TMB (SureBlue TMB 1-Component Microwell Peroxidase Substrate, KPL, catalogue number 52-00-00) was added after the last wash and was allowed to develop. This was stopped with 1M HCl and the signal was then measured using absorbance at 450 nm.

From the raw ELISA data, the concentration of unknown samples was established by interpolation against the standard curve taking into account dilution factors. The mean concentration result from each time point was determined from replicate values and entered into WinNonLin analysis package (e.g. version 5.1 (available from Pharsight Corp., Mountain View, Calif. 94040, USA). The data was fitted using a non-compartmental model, where PK parameters were estimated by the software to give terminal half-lives. Dosing information and time points were selected to reflect the terminal phase of each PK profile.

TABLE 10

Single AlbudAb™ PK

| Species | AlbudAb | Albumin $K_D$ (nM) | AUC h × μg/ml | CL ml/h/kg | t½ h | Vz ml/kg |
|---|---|---|---|---|---|---|
| Rat | DOM7h-14* | 60 | | | | |
| | DOM7h-14-10 | 4 | 2134.6 | 1.2 | 42.1 | 71.2 |
| | DOM7h-11 | 2100 | 320.1 | 7.8 | 23.3 | 263.9 |
| | DOM7h-11-15 | 20 | 843.4 | 3.0 | 30.3 | 130.7 |
| mouse | DOM7h-11 | 5000 | 304.7 | 8.2 | 18.3 | 216.8 |
| | DOM7h-11-15 | 10 | 499.2 | 5.0 | 33.7 | 243.4 |
| Cyno | DOM7h-14* | 66 | | | 217.5 | |
| | DOM7h-14-10 | 9 | 6174.6 | 0.4 | 200.8 | 117.8 |
| | DOM7h-11* | 3300 | | | 135.1 | |
| | DOM7h-11-15 | 3 | 4195 | 0.6 | 198.1 | 170.3 |

*Historical data

Pharmacokinetic parameters derived from rat, mouse and cynomolgus monkey studies were fitted using a non-compartmental model. Key: AUC: Area under the curve from dosing time extrapolated to infinity; CL: clearance; t½: is the time during which the blood concentration is halved; Vz: volume of distribution based on the terminal phase.

DOM7h-11-15 has an improved AUC and t½ in rat and mouse compared to parent. DOM7h-11-15 also has an improved AUC and t½ in cyno compared to parent. This improvement in AUC/t½ correlates with an improved in vitro KD to serum albumin.

Example 7

AlbudAb™ IFN Fusions

Cloning and Expression

As well as single AlbudAbs, the affinity matured Vk Albudabs were linked to Interferon alpha 2b (IFNα2b) to determine whether a useful PK of the AlbudAb was maintained as a fusion protein.

```
Interferon alpha 2b amino acid sequence:
                                                   (SEQ ID NO: 43)
CDLPQTHSLGSRRTLMLLAQMRRISLFSCLKDRHDFGFPQEEFGNQFQKAETIPVLHEMIQ

QIFNLFSTKDSSAAWDETLLDKFYTELYQQLNDLEACVIQGVGVTETPLMKEDSILAVRKYF

QRITLYLKEKKYSPCAWEVVRAEIMRSFSLSTNLQESLRSKE

Interferon alpha 2b nucleotide sequence:
                                                   (SEQ ID NO: 44)
TGTGATCTGCCTCAAACCCACAGCCTGGGTAGCAGGAGGACCTTGATGCTCCTGGCA

CAGATGAGGAGAATCTCTCTTTTCTCCTGCTTGAAGGACAGACATGACTTTGGATTTCC

CCAGGAGGAGTTTGGCAACCAGTTCCAAAAGGCTGAAACCATCCCTGTCCTCCATGA

GATGATCCAGCAGATCTTCAATCTCTTCAGCACAAAGGACTCATCTGCTGCTTGGGAT

GAGACCCTCCTAGACAAATTCTACACTGAACTCTACCAGCAGCTGAATGACCTGGAAG
```

-continued

CCTGTGTGATACAGGGGGTGGGGGTGACAGAGACTCCCCTGATGAAGGAGGACTCC

ATTCTGGCTGTGAGGAAATACTTCCAAAGAATCACTCTCTATCTGAAAGAGAAGAAATA

CAGCCCTTGTGCCTGGGAGGTTGTCAGAGCAGAAATCATGAGATCTTTTTCTTTGTCA

ACAAACTTGCAAGAAAGTTTAAGAAGTAAGGAA

IFNα2b was linked to the AlbudAb via a TVAAPS linker region (see WO2007085814). The constructs were cloned by SOE-PCR (single overlap extension according to the method of Horton et al. Gene, 77, p61 (1989)). PCR amplification of the AlbudAb and IFN sequences were carried out separately using primers with a ~15 base pair overlap at the TVAAPS linker region. The primers used are as follows:—

```
                          (SEQ ID NO: 45)
IFNα2b SOE fragment   GCCCGGATCCACCGGCTGTGATCTG
5'

(SEQ ID NO: 46)
IFNα2b SOE fragment   GGAGGATGGAGACTGGGTCATCTGGATGTC
3'

(SEQ ID NO: 47)
Vk SOE fragment 5'    GACATCCAGATGACCCAGTCTCCATCCTCC (SEQ ID NO: 48)
Vk SOE fragment 3'    GCGCAAGCTTTTATTAATTCAGATCCTCTT
to also introduce a   CTGAGATGAGTTTTTGTTCTGCGGCCGCCC
myc tag               GTTTGATTTCCACCTTGGTCCC
```

The fragments were purified separately and subsequently assembled in a SOE (single overlap extension PCR extension) reaction using only the flanking primers.

```
                          (SEQ ID NO: 49)
IFNα2b SOE fragment   GCCCGGATCCACCGGCTGTGATCTG
5'
```

```
                          (SEQ ID NO: 50)
Vk SOE fragment 3'    GCGCAAGCTTTTATTAATTCAGATCCTCTT
to also introduce a   CTGAGATGAGTTTTTGTTCTGCGGCCGCCC
myc tag               GTTTGATTTCCACCTTGGTCCC
```

The assembled PCR product was digested using the restriction enzymes BamHI and HindIII and the gene ligated into the corresponding sites in the pDOM50, a mammalian expression vector which is a pTT5 derivative with an N-terminal V-J2-C mouse IgG secretory leader sequence to facilitate expression into the cell media.

```
Leader sequence (amino acid):
                          (SEQ ID NO: 51)
METDTLLLWVLLLLWVPGSTG Leader sequence (nucleotide):
                          (SEQ ID NO: 52)
ATGGAGACCGACACCCTGCTGCTGTGGGTGCTGCTGCTGTGGGTGCCCG
GATCCACCGGGC
```

Plasmid DNA was prepared using QIAfilter megaprep (Qiagen). 1 μg DNA/ml was transfected with 293-Fectin into HEK293E cells and grown in serum free media. The protein is expressed in culture for 5 days and purified from culture supernatant using protein L affinity resin and eluted with 100 mM glycine pH2. The proteins were concentrated to greater than 1 mg/ml, buffer exchanged into PBS and endotoxin depleted using Q spin columns (Vivascience).

TABLE 11

Interferon alpha 2b-AlbudAb sequences with and without myc-tag (as amino acid- and nucleotide sequence)
The Interferon alpha 2b is N-terminal to the AlbudAb in the following fusions.

|  | aa + myc | nt + myc | aa no tag | nt no tag |
| --- | --- | --- | --- | --- |
| DMS7321 (IFNα2b-DOM7h-14) | CDLPQTHSLGSRRTL MLLAQMRRISLFSCL KDRHDFGFPQEEFG NQFQKAETIPVLHEMI QQIFNLFSTKDSSAA WDETLLDKFYTELYQ QLNDLEACVIQGVGV TETPLMKEDSILAVRK YFQRITLYLKEKKYSP CAWEVVRAEIMRSFS LSTNLQESLRSKETV AAPSDIQMTQSPSSL SASVGDRVTITCRAS QWIGSQLSWYQQKP GKAPKLLIMWRSSLQ SGVPSRFSGSGSGT DFTLTISSLQPEDFAT YYCAQGAALPRTFGQ GTKVEIKR AAAEQKLISEEDLN* (SEQ ID NO: 53) | TGCGACTTGCCA CAGACACATAGT TTGGGATCAAGA AGAACATTGATG TTATTAGCACAA TGCGTAGAATTT CTTTGTTCTCTTG TCTAAAGGACCG TCACGACTTCGG ATTCCCTCAGGA AGAGTTTGGAAA CCAATTCCAAA AGCAGAAACTAT TCCTGTCTTGCA CGAAATGATCCA GCAAATATTCAAT TTGTTTTCTACAA AGGACTCATCAG CCGCTTGGGATG AAACTCTGTTAG ATAAATTCTACAC TGAACTATATCAA CAACTGAACGAT CTAGAGGCTTGC | CDLPQTHSLGS RRTLMLLAQM RRISLFSCLKD RHDFGFPQEE FGNQFQKAETI PVLHEMIQQIF NLFSTKDSSAA WDETLLDKFYT ELYQQLNDLEA CVIQGVGVTET PLMKEDSILAV RKYFQRITLYLK EKKYSPCAWE VVRAEIMRSFS LSTNLQESLRS KETVAAPSDIQ MTQSPSSLSAS VGDRVTITCRA SQWIGSQLSW YQQKPGKAPK LLIMWRSSLQS GVPSRFSGSG SGTDFTLTISSL QPEDFATYYCA | TGCGACTTGCCA CAGACACATAGT TTGGGATCAAGA AGAACATTGATG TTATTAGCACAA ATGCGTAGAATT TCTTTGTTCTCTT GTCTAAAGGACC GTCACGACTTCG GATTCCCTCAGG AAGAGTTTGGAA ACCAATTCCAAA AAGCAGAAACTA TTCCTGTCTTGC ACGAAATGATCC AGCAAATATTCA ATTTGTTTTCTAC AAAGGACTCATC AGCCGCTTGGGA TGAAACTCTGTT AGATAAATTCTA CACTGAACTATA TCAACAACTGAA CGATCTAGAGGC |

TABLE 11-continued

Interferon alpha 2b-AlbudAb sequences with and without myc-tag (as amino acid- and nucleotide sequence)
The Interferon alpha 2b is N-terminal to the AlbudAb in the following fusions.

| | aa + myc | nt + myc | aa no tag | nt no tag |
|---|---|---|---|---|
| | | GTTATTCAGGGT<br>GTAGGAGTTACT<br>GAAACTCCCCTA<br>ATGAAAGAAGAT<br>TCAATTCTAGCC<br>GTTAGAAAATACT<br>TTCAGCGTATCA<br>CATTGTATTTAAA<br>GGAAAAGAAATA<br>CTCCCCATGTGC<br>ATGGGAGGTGGT<br>TAGAGCAGAAAT<br>TATGAGGTCCTT<br>CTCTCTTTCTACG<br>AATTTGCAAGAAT<br>CTTTGAGATCTAA<br>GGAAACCGTCGC<br>TGCTCCATCTGA<br>CATCCAGATGAC<br>CCAGTCTCCATC<br>CTCCCTGTCTGC<br>ATCTGTAGGAGA<br>CCGTGTCACCAT<br>CACTTGCCGGGC<br>AAGTCAGTGGAT<br>TGGGTCTCAGTT<br>ATCTTGGTACCA<br>GCAGAAACCAGG<br>GAAAGCCCCTAA<br>GCTCCTGATCAT<br>GTGGCGTTCCTC<br>GTTGCAAAGTGG<br>GGTCCCATCACG<br>TTTCAGTGGCAG<br>TGGATCTGGGAC<br>AGATTTCACTCTC<br>ACCATCAGCAGT<br>CTGCAACCTGAA<br>GATTTTGCTACG<br>TACTACTGTGCT<br>CAGGGTGCGGC<br>GTTGCCTAGGAC<br>GTTCGGCCAAGG<br>GACCAAGGTGGA<br>AATCAAACGGGC<br>GGCCGCAGAAC<br>AAAAACTCATCT<br>CAGAAGAGGAT<br>CTGAATTAA<br>(SEQ ID NO: 54) | QGAALPRTFG<br>QGTKVEIKR<br>(SEQ ID NO: 55) | TTGCGTTATTCA<br>GGGTGTAGGAGT<br>TACTGAAACTCC<br>CCTAATGAAAGA<br>AGATTCAATTCTA<br>GCCGTTAGAAAA<br>TACTTTCAGCGT<br>ATCACATTGTATT<br>TAAAGGAAAAGA<br>AATACTCCCCAT<br>GTGCATGGGAG<br>GTGGTTAGAGCA<br>GAAATTATGAGG<br>TCCTTCTCTCTTT<br>CTACGAATTTGC<br>AAGAATCTTTGA<br>GATCTAAGGAAA<br>CCGTCGCTGCTC<br>CATCTGACATCC<br>AGATGACCCAGT<br>CTCCATCCTCCC<br>TGTCTGCATCTG<br>TAGGAGACCGTG<br>TCACCATCACTT<br>GCCGGGCAAGT<br>CAGTGGATTGGG<br>TCTCAGTTATCTT<br>GGTACCAGCAGA<br>AACCAGGGAAAG<br>CCCCTAAGCTCC<br>TGATCATGTGGC<br>GTTCCTCGTTGC<br>AAAGTGGGGTCC<br>CATCACGTTTCA<br>GTGGCAGTGGAT<br>CTGGGACAGATT<br>TCACTCTCACCA<br>TCAGCAGTCTGC<br>AACCTGAAGATT<br>TTGCTACGTACT<br>ACTGTGCTCAGG<br>GTGCGGCGTTG<br>CCTAGGACGTTC<br>GGCCAAGGGAC<br>CAAGGTGGAAAT<br>CAAACGG (SEQ<br>ID NO: 56) |
| DMS732<br>(IFNα2b-<br>DOM7h-<br>14-10) | CDLPQTHSLGSRRTL<br>MLLAQMRRISLFSCL<br>KDRHDFGFPQEEFG<br>NQFQKAETIPVLHEMI<br>QQIFNLFSTKDSSAA<br>WDETLLDKFYTELYQ<br>QLNDLEACVIQGVGV<br>TETPLMKEDSILAVRK<br>YFQRITLYLKEKKYSP<br>CAWEVVRAEIMRSFS<br>LSTNLQESLRSKETV<br>AAPSDIQMTQSPSSL<br>SASVGDRVTITCRAS<br>QWIGSQLSWYQQKP<br>GKAPKLLIMWRSSLQ<br>SGVPSRFSGSGSGT<br>DFTLTISSLQPEDFAT<br>YYCAQGLRHPKTFG<br>QGTKVEIKR<br>AAAEQKLISEEDLN*<br>(SEQ ID NO: 57) | TGCGACTTGCCA<br>CAGACACATAGT<br>TTGGGATCAAGA<br>AGAACATTGATG<br>TTATTAGCACAAA<br>TGCGTAGAATTT<br>CTTTGTTCTCTTG<br>TCTAAAGGACCG<br>TCACGACTTCGG<br>ATTCCCTCAGGA<br>AGAGTTTGGAAA<br>CCAATTCCAAAA<br>AGCAGAAACTAT<br>TCCTGTCTTGCA<br>CGAAATGATCCA<br>GCAAATATTCAAT<br>TTGTTTTCTACAA<br>AGGACTCATCAG<br>CCGCTTGGGATG<br>AAACTCTGTTAG<br>ATAAATTCTACAC<br>TGAACTATATCAA<br>CAACTGAACGAT | CDLPQTHSLGS<br>RRTLMLLAQM<br>RRISLFSCLKD<br>RHDFGFPQEE<br>FGNQFQKAETI<br>PVLHEMIQQIF<br>NLFSTKDSSAA<br>WDETLLDKFYT<br>ELYQQLNDLEA<br>CVIQGVGVTET<br>PLMKEDSILAV<br>RKYFQRITLYLK<br>EKKYSPCAWE<br>VVRAEIMRSFS<br>LSTNLQESLRS<br>KETVAAPSDIQ<br>MTQSPSSLSAS<br>VGDRVTITCRA<br>SQWIGSQLSW<br>YQQKPGKAPK<br>LLIMWRSSLQS<br>GVPSRFSGSG<br>SGTDFTLTISSL | TGCGACTTGCCA<br>CAGACACATAGT<br>TTGGGATCAAGA<br>AGAACATTGATG<br>TTATTAGCACAA<br>ATGCGTAGAATT<br>TCTTTGTTCTCTT<br>GTCTAAAGGACC<br>GTCACGACTTCG<br>GATTCCCTCAGG<br>AAGAGTTTGGAA<br>ACCAATTCCAAA<br>AAGCAGAAACTA<br>TTCCTGTCTTGC<br>ACGAAATGATCC<br>AGCAAATATTCA<br>ATTTGTTTTCTAC<br>AAAGGACTCATC<br>AGCCGCTTGGGA<br>TGAAACTCTGTT<br>AGATAAATTCTA<br>CACTGAACTATA<br>TCAACAACTGAA |

TABLE 11-continued

Interferon alpha 2b-AlbudAb sequences with and without myc-tag (as amino acid- and nucleotide sequence)
The Interferon alpha 2b is N-terminal to the AlbudAb in the following fusions.

| | aa + myc | nt + myc | aa no tag | nt no tag |
|---|---|---|---|---|
| | | CTAGAGGCTTGC GTTATTCAGGGT GTAGGAGTTACT GAAACTCCCCTA ATGAAAGAAGAT TCAATTCTAGCC GTTAGAAAATACT TTCAGCGTATCA CATTGTATTTAAA GGAAAAGAAATA CTCCCCATGTGC ATGGGAGGTGGT TAGAGCAGAAAT TATGAGGTCCTT CTCTCTTTCTACG AATTTGCAAGAAT CTTTGAGATCAA GGAAACCGTCGC TGCTCCATCTGA CATCCAGATGAC CCAGTCTCCATC CTCCCTGTCTGC ATCTGTAGGAGA CCGTGTCACCAT CACTTGCCGGGC AAGTCAGTGGAT TGGGTCTCAGTT ATCTTGGTACCA GCAGAAACCAGG GAAAGCCCCTAA GCTCCTGATCAT GTGGCGTTCCTC GTTGCAAAGTGG GGTCCCATCACG TTTCAGTGGCAG TGGATCTGGGAC AGATTTCACTCTC ACCATCAGCAGT CTGCAACCTGAA GATTTTGCTACG TACTACTGTGCT CAGGGTTTGAGG CATCCTAAGACG TTCGGCCAAGGG ACCAAGGTGGAA ATCAAACGGGCG GCCGCAGAACA AAAACTCATCTC AGAAGAGGATCT GAATTAA (SEQ ID NO: 58) | QPEDFATYYCA QGLRHPKTFG QGTKVEIKR (SEQ ID NO: 59) | CGATCTAGAGGC TTGCGTTATTCA GGGTGTAGGAGT TACTGAAACTCC CCTAATGAAAGA AGATTCAATTCTA GCCGTTAGAAAA TACTTTCAGCGT ATCACATTGTATT TAAAGGAAAAGA AATACTCCCCAT GTGCATGGGAG GTGGTTAGAGCA GAAATTATGAGG TCCTTCTCTCTTT CTACGAATTTGC AAGAATCTTTGA GATCTAAGGAAA CCGTCGCTGCTC CATCTGACATCC AGATGACCCAGT CTCCATCCTCCC TGTCTGCATCTG TAGGAGACCGTG TCACCATCACTT GCCGGGCAAGT CAGTGGATTGGG TCTCAGTTATCTT GGTACCAGCAGA AACCAGGGAAAG CCCCTAAGCTCC TGATCATGTGGC GTTCCTCGTTGC AAAGTGGGGTCC CATCACGTTTCA GTGGCAGTGGAT CTGGGACAGATT TCACTCTCACCA TCAGCAGTCTGC AACCTGAAGATT TTGCTACGTACT ACTGTGCTCAGG GTTTGAGGCATC CTAAGACGTTCG GCCAAGGGACC AAGGTGGAAATC AAACGG (SEQ ID NO: 60) |
| DMS7325 (IFNα2b- DOM7h- 11) | CDLPQTHSLGSRRTL MLLAQMRRISLFSCL KDRHDFGFPQEEFG NQFQKAETIPVLHEMI QQIFNLFSTKDSSAA WDETLLDKFYTELYQ QLNDLEACVIQGVGV TETPLMKEDSILAVRK YFQRITLYLKEKKYSP CAWEVVRAEIMRSFS LSTNLQESLRSKETV AAPSDIQMTQSPSSL SASVGDRVTITCRAS RPIGTTLSWYQQKPG KAPKLLIWFGSRLQS GVPSRFSGSGSGTD FTLTISSLQPEDFATY YCAQAGTHPTTFGQ GTKVEIKR AAAEQKLISEEDLN\* | TGCGACTTGCCA CAGACACATAGT TTGGGATCAAGA AGAACATTGATG TGCGTAGAATTT CTTTGTTCTCTTG TCTAAAGGACCG TCACGACTTCGG ATTCCCTCAGGA AGAGTTTGGAAA CCAATTCCAAAA AGCAGAAACTAT TCCTGTCTTGCA CGAAATGATCCA GCAAATATTCAAT TTGTTTTCTACAA AGGACTCATCAG CCGCTTGGGATG AAACTCTGTTAG | CDLPQTHSLGS RRTLMLLAQM RRISLFSCLKD RHDFGFPQEE FGNQFQKAETI PVLHEMIQQIF NLFSTKDSSAA WDETLLDKFYT ELYQQLNDLEA CVIQGVGVTET PLMKEDSILAV RKYFQRITLYLK EKKYSPCAWE VVRAEIMRSFS LSTNLQESLRS KETVAAPSDIQ MTQSPSSLSAS VGDRVTITCRA SRPIGTTLSWY QQKPGKAPKLL | TGCGACTTGCCA CAGACACATAGT TTGGGATCAAGA AGAACATTGATG TTATTAGCACAA ATGCGTAGAATT TCTTTGTTCTCTT GTCTAAAGGACC GTCACGACTTCG GATTCCCTCAGG AAGAGTTTGGAA ACCAATTCCAAA AAGCAGAAACTA TTCCTGTCTTGC ACGAAATGATCC AGCAAATATTCA ATTTGTTTTCTAC AAAGGACTCATC AGCCGCTTGGGA TGAAACTCTGTT |

TABLE 11-continued

Interferon alpha 2b-AlbudAb sequences with and without myc-tag (as amino acid- and nucleotide sequence)
The Interferon alpha 2b is N-terminal to the AlbudAb in the following fusions.

| | aa + myc | nt + myc | aa no tag | nt no tag |
|---|---|---|---|---|
| | (SEQ ID NO: 61) | ATAAATTCTACAC<br>TGAACTATATCAA<br>CAACTGAACGAT<br>CTAGAGGCTTGC<br>GTTATTCAGGGT<br>GTAGGAGTTACT<br>GAAACTCCCCTA<br>ATGAAAGAAGAT<br>TCAATTCTAGCC<br>GTTAGAAAATACT<br>TTCAGCGTATCA<br>CATTGTATTTAAA<br>GGAAAAGAAATA<br>CTCCCCATGTGC<br>ATGGGAGGTGGT<br>TAGAGCAGAAAT<br>TATGAGGTCCTT<br>CTCTCTTTCTACG<br>AATTTGCAAGAAT<br>CTTTGAGATCTAA<br>GGAAACCGTCGC<br>TGCTCCATCTGA<br>CATCCAGATGAC<br>CCAGTCTCCATC<br>CTCCCTGTCTGC<br>ATCTGTAGGAGA<br>CCGTGTCACCAT<br>CACTTGCCGGGC<br>AAGTCGTCCGAT<br>TGGGACGACGTT<br>AAGTTGGTACCA<br>GCAGAAACCAGG<br>GAAAGCCCCTAA<br>GCTCCTGATCTG<br>GTTTGGTTCCCG<br>GTTGCAAAGTGG<br>GGTCCCATCACG<br>TTTCAGTGGCAG<br>TGGATCTGGGAC<br>AGATTTCACTCTC<br>ACCATCAGCAGT<br>CTGCAACCTGAA<br>GATTTTGCTACG<br>TACTACTGTGCG<br>CAGGCTGGGAC<br>GCATCCTACGAC<br>GTTCGGCCAAGG<br>GACCAAGGTGGA<br>AATCAAACGGGC<br>GGCCGCAGAAC<br>AAAAACTCATCT<br>CAGAAGAGGAT<br>CTGAATTAA<br>(SEQ ID NO: 62) | IWFGSRLQSGV<br>PSRFSGSGSG<br>TDFTLTISSLQP<br>EDFATYYCAQA<br>GTHPTTFGQG<br>TKVEIKR (SEQ<br>ID NO: 63) | AGATAAATTCTA<br>CACTGAACTATA<br>TCAACAACTGAA<br>CGATCTAGAGGC<br>TTGCGTTATTCA<br>GGGTGTAGGAGT<br>TACTGAAACTCC<br>CCTAATGAAAGA<br>AGATTCAATTCTA<br>GCCGTTAGAAAA<br>TACTTTCAGCGT<br>ATCACATTGTATT<br>TAAAGGAAAAGA<br>AATACTCCCCAT<br>GTGCATGGGAG<br>GTGGTTAGAGCA<br>GAAATTATGAGG<br>TCCTTCTCTCTTT<br>CTACGAATTTGC<br>AAGAATCTTTGA<br>GATCTAAGGAAA<br>CCGTCGCTGCTC<br>CATCTGACATCC<br>AGATGACCCAGT<br>CTCCATCCTCCC<br>TGTCTGCATCTG<br>TAGGAGACCGTG<br>TCACCATCACTT<br>GCCGGGCAAGT<br>CGTCCGATTGGG<br>ACGACGTTAAGT<br>TGGTACCAGCAG<br>AAACCAGGGAAA<br>GCCCCTAAGCTC<br>CTGATCTGGTTT<br>GGTTCCCGGTTG<br>CAAAGTGGGGTC<br>CCATCACGTTTC<br>AGTGGCAGTGGA<br>TCTGGGACAGAT<br>TTCACTCTCACC<br>ATCAGCAGTCTG<br>CAACCTGAAGAT<br>TTTGCTACGTAC<br>TACTGTGCGCAG<br>GCTGGGACGCAT<br>CCTACGACGTTC<br>GGCCAAGGGAC<br>CAAGGTGGAAAT<br>CAAACGG (SEQ<br>ID NO: 64) |
| DMS7327<br>(IFNα2b-<br>DOM7h-<br>11-15) | CDLPQTHSLGSRRTL<br>MLLAQMRRISLFSCL<br>KDRHDFGFPQEEFG<br>NQFQKAETIPVLHEMI<br>QQIFNLFSTKDSSAA<br>WDETLLDKFYTELYQ<br>QLNDLEACVIQGVGV<br>TETPLMKEDSILAVRK<br>YFQRITLYLKEKKYSP<br>CAWEVVRAEIMRSFS<br>LSTNLQESLRSKETV<br>AAPSDIQMTQSPSSL<br>SASVGDRVTITCRAS<br>RPIGTMLSWYQQKP<br>GKAPKLLILAFSRLQS<br>GVPSRFSGSGSGTD<br>FTLTISSLQPEDFATY<br>YCAQAGTHPTTFGQ | TGCGACTTGCCA<br>CAGACACATAGT<br>TTGGGATCAAGA<br>AGAACATTGATG<br>TTATTAGCACAAA<br>TGCGTAGAATTT<br>CTTTGTTCTCTTG<br>TCTAAAGGACCG<br>TCACGACTTCGG<br>ATTCCCTCAGGA<br>AGAGTTTGGAAA<br>CCAATTCCAAAA<br>AGCAGAAACTAT<br>TCCTGTCTTGCA<br>CGAAATGATCCA<br>GCAAATATTCAAT<br>TTGTTTTCTACAA<br>GGACTCATCAG | CDLPQTHSLGS<br>RRTLMLLAQM<br>RRISLFSCLKD<br>RHDFGFPQEE<br>FGNQFQKAETI<br>PVLHEMIQQIF<br>NLFSTKDSSAA<br>WDETLLDKFYT<br>ELYQQLNDLEA<br>CVIQGVGVTET<br>PLMKEDSILAV<br>RKYFQRITLYLK<br>EKKYSPCAWE<br>VVRAEIMRSFS<br>LSTNLQESLRS<br>KETVAAPSDIQ<br>MTQSPSSLSAS<br>VGDRVTITCRA | TGCGACTTGCCA<br>CAGACACATAGT<br>TTGGGATCAAGA<br>AGAACATTGATG<br>TTATTAGCACAA<br>ATGCGTAGAATT<br>TCTTTGTTCTCTT<br>GTCTAAAGGACC<br>GTCACGACTTCG<br>GATTCCCTCAGG<br>AAGAGTTTGGAA<br>ACCAATTCCAAA<br>AAGCAGAAACTA<br>TTCCTGTCTTGC<br>ACGAAATGATCC<br>AGCAAATATTCA<br>ATTTGTTTTCTAC<br>AAAGGACTCATC |

TABLE 11-continued

Interferon alpha 2b-AlbudAb sequences with and without myc-tag (as amino acid- and nucleotide sequence)
The Interferon alpha 2b is N-terminal to the AlbudAb in the following fusions.

| aa + myc | nt + myc | aa no tag | nt no tag |
|---|---|---|---|
| GTKVEIKR AAAEQKLISEEDLN* (SEQ ID NO: 65) | CCGCTTGGGATG AAACTCTGTTAG ATAAATTCTACAC TGAACTATATCAA CAACTGAACGAT CTAGAGGCTTGC GTTATTCAGGGT GTAGGAGTTACT GAAACTCCCTA ATGAAAGAAGAT TCAATTCTAGCC GTTAGAAAATACT TTCAGCGTATCA CATTGTATTTAAA GGAAAAGAAATA CTCCCCATGTGC ATGGGAGGTGGT TAGAGCAGAAAT TATGAGGTCCTT CTCTCTTTCTACG AATTTGCAAGAAT CTTTGAGATCTAA GGAAACCGTCGC TGCTCCATCTGA CATCCAGATGAC CCAGTCTCCATC CTCCCTGTCTGC ATCTGTAGGAGA CCGTGTCACCAT CACTTGCCGGGC AAGTCGTCCGAT TGGGACGATGTT AAGTTGGTACCA GCAGAAACCAGG GAAAGCCCCTAA GCTCCTGATCCT TGCTTTTTCCCGT TTGCAAAGTGGG GTCCCATCACGT TTCAGTGGCAGT GGATCTGGGACA GATTTCACTCTCA CCATCAGCAGTC TGCAACCTGAAG ATTTTGCTACGTA CTACTGCGCGCA GGCTGGGACGC ATCCTACGACGT TCGGCCAAGGGA CCAAGGTGGAAA TCAAACGGGCGG CCGCAGAACAA AAACTCATCTCA GAAGAGGATCTG AATTAA (SEQ ID NO: 66) | SRPIGTMLSWY QQKPGKAPKLL ILAFSRLQSGV PSRFSGSGSG TDFTLTISSLQP EDFATYYCAQA GTHPTTFGQG TKVEIKR (SEQ ID NO: 67) | AGCCGCTTGGGA TGAAACTCTGTT AGATAAATTCTA CACTGAACTATA TCAACAACTGAA CGATCTAGAGGC TTGCGTTATTCA GGGTGTAGGAGT TACTGAAACTCC CCTAATGAAAGA AGATTCAATTCTA GCCGTTAGAAAA TACTTTCAGCGT ATCACATTGTATT TAAAGGAAAAGA AATACTCCCCAT GTGCATGGGAG GTGGTTAGAGCA GAAATTATGAGG TCCTTCTCTCTTT CTACGAATTTGC AAGAATCTTTGA GATCTAAGGAAA CCGTCGCTGCTC CATCTGACATCC AGATGACCCAGT CTCCATCCTCCC TGTCTGCATCTG TAGGAGACCGTG TCACCATCACTT GCCGGGCAAGT CGTCCGATTGGG ACGATGTTAAGT TGGTACCAGCAG AAACCAGGGAAA GCCCCTAAGCTC CTGATCCTTGCT TTTTCCCGTTTG CAAAGTGGGGTC CCATCACGTTTC AGTGGCAGTGGA TCTGGGACAGAT TTCACTCTCACC ATCAGCAGTCTG CAACCTGAAGAT TTTGCTACGTAC TACTGCGCGCAG GCTGGGACGCAT CCTACGACGTTC GGCCAAGGGAC CAAGGTGGAAAT CAAACGG (SEQ ID NO: 68) |

The amino acid and nucleotide sequences highlighted in bold represents the cloning site and MYC tag.
*represents the stop codon at the end of the gene.

Affinity Determination and Biophysical Characterisation:

To determine the binding affinity ($K_D$) of the AlbudAb-IFNα2b fusion proteins to each serum albumin; purified fusion proteins were analysed by BIAcore over albumin (immobilised by primary-amine coupling onto CM5 chips; BIAcore) using fusion protein concentrations from 5000 nM to 39 nM (5000 nM, 2500 nM, 1250 nM, 625 nM, 312 nM, 156 nM, 78 nM, 39 nM) in HBS-EP BIAcore buffer.

TABLE 12

| | | Affinity to SA | | |
|---|---|---|---|---|
| AlbudAb | Fusion | Affinity to SA (nM) | Kd | Ka |
| | | Rat | | |
| DOM7h-14 | IFNα2b | 350 | 4.500E−02 | 1.28E+05 |
| DOM7h-14-10 | IFNα2b | 16 | 4.970E−03 | 5.90E+05 |

TABLE 12-continued

Affinity to SA

| AlbudAb | Fusion | Affinity to SA (nM) | Kd | Ka |
|---|---|---|---|---|
| DOM 7h-11 | IFNα2b | 6000 | 7.500E−01 | nd |
| DOM 7h-11-15 | IFNα2b | 200 | 1.660E−02 | 1.50E+05 |
| Cyno | | | | |
| DOM 7h-14 | IFNα2b | 60 | 1.32E−02 | 5.0E+05 |
| DOM 7h-14-10 | IFNα2b | 19 | 7.05E−03 | 4.50E+05 |
| DOM 7h-11 | IFNα2b | 3300 | 3.59E−01 | 1.20E+05 |
| DOM 7h-11-15 | IFNα2b | 15 | 4.86E−03 | 3.60E+05 |
| Mouse | | | | |
| DOM 7h-14 | IFNα2b | 240 | 3.21E−02 | 1.50E+06 |
| DOM 7h-14-10 | IFNα2b | 60 | 3.45E−02 | 6.86E+05 |
| DOM 7h-11 | IFNα2b | 6000 | 1.55E−01 | nd |
| DOM 7h-11-15 | IFNα2b | 28 | 6.69E−03 | 2.80E+05 |
| Human | | | | |
| DOM 7h-14 | IFNα2b | 244 | 2.21E−02 | 9.89E+04 |
| DOM 7h-14-10 | IFNα2b | 32 | 6.58E−03 | 3.48E+05 |
| DOM 7h-11 | IFNα2b | 670 | 2.02E−01 | 7.00E+05 |
| DOM 7h-11-15 | IFNα2b | 10 | 1.87E−03 | 3.50E+05 |

When IFNα2b is linked to the AlbudAb variants, in all cases the affinity of AlbudAb binding to serum albumin is reduced. DOM7h-14-10 and DOM7-11-15 retain improved binding affinity to serum albumin across species compared to parent.

TABLE 13

Biophysical Characterisation
Biophysical Characterisation was carried out by SEC MALLS and DSC as described above for the single AlbudAbs.

| AlbudAb | Fusion | DMS number | Biophysical parameters SEC MALLS | DSC Tm (° C.) |
|---|---|---|---|---|
| DOM 7h-14 | IFNα2b | DMS7321 | M/D | 58-65 |
| DOM 7h-14-10 | IFNα2b | DMS7322 | M/D | 55-65 |
| DOM 7h-11 | IFNα2b | DMS7325 | M/D | 65.8-66.2 |
| DOM 7h-11-15 | IFNα2b | DMS7327 | M/D | 56.3-66.2 |

M/D indicates a monomer/dimer equilibrium as detected by SEC MALLS

We observed expression for all clones in Table 13 in the range of 17.5 to 54 mg/L in HEK293.

For IFNα2b-DOM7h-14 and IFNα2b-DOM7h-11 variants, favorable biophysical parameters and expression levels were maintained during affinity maturation.

PK Determination for AlbudAb-IFNα2b Fusions

AlbudAbs IFNα2b fusions DMS7321 (IFNα2b-DOM7h-14) DMS7322 (IFNα2b-DOM7h-14-10), DMS7325 (IFNα2b-DOM7h-11), DMS7327 (IFNα2b-DOM7h-11-15) were expressed with the myc tag at 20-50 mg quantities in HEK293 cells and purified from culture supernatant using protein L affinity resin and eluted with 100 mM glycine pH2. The proteins were concentrated to greater than 1 mg/ml, buffer exchanged into Dulbecco's PBS and endotoxin depleted using Q spin columns (Vivascience).

For Rat PK, IFN-AlbudAbs were dosed as single i.v injections at 2.0 mg/kg using 3 rats per compound. Serum samples were taken at 0.16, 1, 4, 8, 24, 48, 72, 120, 168 hrs. Analysis of serum levels was by EASY ELISA according to manufacturer's instructions (GE Healthcare, catalogue number RPN5960).

For Mouse PK, DMS7322 (IFN2b-DOM7h-14-10) DMS7325 (IFN2b-DOM7h-11), DMS7327 (IFN2b-DOM7h-11-15) all with myc tags were dosed as single i.v injections at 2.0 mg/kg per dose group of 3 subjects and serum samples taken at 10 mins; 1 h; 8 h; 24 h; 48 h; 72 h; 96 h. Analysis of serum levels was by EASY ELISA according to manufacturer's instructions (GE Healthcare, catalogue number RPN5960).

TABLE 14

| Species | AlbudAb | Fusion | Albu-min $K_D$ (nM) | PK parameters (mean results) | | | |
|---|---|---|---|---|---|---|---|
| | | | | AUC h × ug/ml | CL ml/h/kg | t1/2 h | Vz ml/kg |
| Rat | 7h-14 | IFNα2b | 350 | 832.1 | 2.4 | 27 | 94.5 |
| | 7h-14-10 | IFNα2b | 16 | 1380.7 | 1.5 | 35.8 | 75.2 |
| | 7h-11 | IFNα2b | 6000 | 327.9 | 6.5 | 11 | 101.9 |
| | 7h-11-15 | IFNα2b | 200 | 1118.7 | 1.8 | 39.5 | 103.6 |
| | 7h-11-12 | IFNα2b | 1700 | 747.1 | 2.8 | 25.8 | 104.7 |
| mouse | 7h-14 | IFNα2b | 240 | 761.2 | 2.6 | 30.4 | 115.3 |
| | 7h-14-10 | IFNα2b | 60 | 750.5 | 2.7 | 30.9 | 118.6 |
| | 7h-11 | IFNα2b | 6000 | 493.9 | 4.0 | 8.8 | 51.2 |
| | 7h-11-15 | IFNα2b | 28 | 971.8 | 2.1 | 33.6 | 99.6 |

Pharmacokinetic parameters derived from rat and mouse studies were fitted using a non-compartmental model. Key: AUC: Area under the curve from dosing time extrapolated to infinity; CL: clearance; t½: is the time during which the blood concentration is halved; Vz: volume of distribution based on the terminal phase.

IFNα2b—AlbudAbs were tested in rat and mouse. For all IFNα2b-DOM7h-11 variant fusion proteins in both rat and mouse, t½ is improved compared to parent. The improvement in t½ correlates with the improved in vitro $K_D$ to serum albumin. For IFNα2b-DOM7h-14-10 variants, the improvement in in vitro $K_D$ to serum albumin also correlated to an improvement in t½ in rat.

All IFNα2b-AlbudAb fusion proteins exhibit a 5 to 10-fold decrease in the binding to RSA compared to the single AlbudAb. This effect is more pronounced (i.e. 10-fold) for the DOM7h-14 series than the DOM7h-11 series (only 5-fold decrease).

Example 8

Further AlbudAb Fusions with Proteins, Peptides and NCEs

Various AlbudAbs fused to other chemical entities namely domain antibodies (dAbs), peptides and NCEs were tested. The results are shown in table 15.

TABLE 15

| Species | AlbudAb | Fusion | Albumin $K_D$ (nM) | PK parameters AUC h × ug/ml | CL ml/h/kg | t½ h | Vz ml/kg |
|---|---|---|---|---|---|---|---|
| Rat | DOM7h-14 | Exendin-4 | 2400 | 18 | 57.1 | 11 | 901.9 |
| | DOM7h-14-10 | Exendin-4 | 19 | 43.6 | 23.1 | 22.1 | 740.3 |
| | DOM7h-11 | Exendin-4 | 2400 | 6.1 | 168 | 7.1 | 1684.1 |
| | DOM7h-11-15 | Exendin-4 | 273 | 36.3 | 27.6 | 19.3 | 765.7 |
| In a different experiement | DOM7h-11-15 | Exendin-4 | 130 | not tested | not tested | not tested | not tested |
| | DOM7h14-10 | NCE-GGGGSC | 62 | | | | |
| | DOM7h14-10 | NCE-TVAAPSC | 35 | | | | |
| Human | DOM7h-14 | NCE | 204 | | | | |
| mouse | DOM7h-11 | DOM1m-21-23 | | 234 | 10.7 | 4.7 | 72.5 |
| | DOM7h-11-15 | DOM1m-21-23 | | 1008 | 2.5 | 17.4 | 62.4 |

Key: DOM1m-21-23 is an anti-TNFR1 dAb, Exendin-4 is a peptide (a GLP-1 agonist) of 39 amino acids length. NCE, NCE-GGGGSC and NCE-TVAAPSC are described below.

Previously we have described the use of genetic fusions with an albumin-binding dAb (AlbudAb) to extend the PK half-life of anti-TNFR1 dAbs in vivo (see, e.g., WO04003019, WO2006038027, WO2008149148). Reference is made to the protocols in these PCT applications. In the table above, DOM1m-21-23 is an anti-mouse TNFR1 dAb.

To produce genetic fusions of exendin-4 or with DOM7h-14 (or other AlbudAb) which binds serum albumin, the exendin-4-linker-AlbudAb sequence was cloned into the pTT-5 vector (obtainable from CNRC, Canada). In each case the exendin-4 was at the 5' end of the construct and the dAb at the 3' end. The linker was a $(G_4S)_3$ linker. Endotoxin-free DNA was prepared in E. coli using alkaline lysis (using the endotoxin-free plasmid Giga kit, obtainable from Qiagen CA) and used to transfect HEK293E cells (obtainable from CNRC, Canada). Transfection was into 250 ml/flask of HEK293E cells at $1.75 \times 10^6$ cells/ml using 333 ul of 293fectin (Invitrogen) and 250 ug of DNA per flask and expression was at 30° C. for 5 days. The supernatant was harvested by centrifugation and purification was by affinity purification on protein L. Protein was batch bound to the resin, packed on a column and washed with 10 column volumes of PBS. Protein was eluted with 50 ml of 0.1M glycine pH2 and neutralized with Tris pH8. Protein of the expected size was identified on an SDS-PAGE gel.

NCE Albudab™ Fusions:

A new chemical entity (NCE) AlbudAb fusion was tested. The NCE, a small molecule ADAMTS-4 inhibitor was synthesised with a PEG linker (PEG 4 linker (i.e. 4 PEG molecules before the maleimide) and a maleimide group for conjugation to the AlbudAb. Conjugation of the NCE to the AlbudAb is via an engineered cysteine residue at amino acid position R108C, or following a 5 amino acid (GGGGSC) or 6 amino acid (TVAAPSC) spacer engineered at the end of the AlbudAb. Briefly, the AlbudAb was reduced with TCEP (Pierce, Catalogue Number 77720), desalted using a PD10 column (GE healthcare) into 25 mM Bis-Tris, 5 mM EDTA, 10% (v/v) glycerol pH6.5. A 5 fold molar excess of maleimide activated NCE was added in DMSO not to exceed 10% (V/V) final concentration. The reaction was incubated over night at room temperature and dialysed extensively into 20 mM Tris pH7.4

PEG Linker:

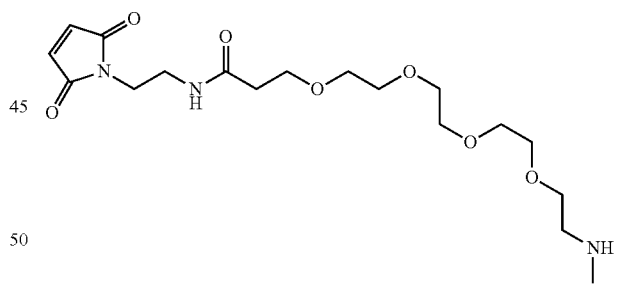

Sequences:
DOM7h-14 R108C:

(SEQ ID NO: 69)
DIQMTQSPSSLSASVGDRVTITCRASQWIGSQLSWYQQKPGKAPKLLIMWRSSLQSGVPS

RFSGSGSGTDFTLTISSLQPEDFATYYCAQGLRHPKTFGQGTKVEIKC (SEQ ID NO: 70)
Nucleotide:
GACATCCAGATGACCCAGTCTCCATCCTCCCTGTCTGCATCTGTAGGAGACCGTGTCA

CCATCACTTGCCGGGCAAGTCAGTGGATTGGGTCTCAGTTATCTTGGTACCAGCAGAA

ACCAGGGAAAGCCCCTAAGCTCCTGATCATGTGGCGTTCCTCGTTGCAAAGTGGGGT

-continued

```
CCCATCACGTTTCAGTGGCAGTGGATCTGGGACAGATTTCACTCTCACCATCAGCAGT

CTGCAACCTGAAGATTTTGCTACGTACTACTGTGCTCAGGGTTTGAGGCATCCTAAGA

CGTTCGGCCAAGGGACCAAGGTGGAAATCAAATGC
```

See table 5 for the sequences of DOM7h-14-10/TVAAPSC and DOM7h-14-10/GGGGSC (ie, DOM7h-14-10/G4SC).

NCE-AlbudAbs DOM7h-14-10 GGGGSC and DOM7h14-10 TVAAPSC, exhibit a 5 to 10 fold decrease in in vitro affinity ($K_D$) to RSA as determined by BIAcore when fused to the chemical entity.

dAb-Albudab fusion: the 2 DOM7h-11 AlbudAbs with the highest affinity to RSA experience a 2-fold decrease in affinity to RSA as on BIAcore when fused to a therapeutic domain antibody (DOM1m-21-23) compared to the unfused AlbudAb. The DOM7h-11 clone shows a micromolar $K_D$ when fused (2.8 uM) as well as when unfused (~5 uM).

Exendin 4-AlbudAb fusion: the effect of fusing the Albud-Abs to a peptide on the binding ability to RSA is about 10-fold, apart from DOM7h-14-10, which only shows a 4-fold decrease in binding. The effect, however, is more pronounced for the DOM7h-14 series (except DOM7h-14-10) than it appears to be for the DOM7h-11 series.

For all the above data, the T½ of the fusion increased with improved affinity to the species' SA.

We generally classify Albudab-therapeutics as being therapeutically amenable (for treatment and/or prophylaxis of diseases, conditions or indications) when the AlbudAb-drug fusions show an affinity range ($K_D$) of from 0.1 nM to 10 mM for serum albumin binding.

We define the therapeutic ranges of AlbudAbs and AlbudAb fusions (Protein-AlbudAbs for example IFNα2b-DOM7h-14-10; Peptide-AlbudAbs for example Exendin-4-DOM7h-14-10; dAb-AlbudAbs for example DOM1m21-23-DOM7h11-15; NCE-AlbudAb for example ADAMTS-4-DOM7h-14-10) as follows: Affinity ($K_D$) ranges that are useful for therapy of chronic or acute conditions, diseases or indications are shown. Also shown are affinity ranges marked as "intermediate". AlbudAbs and fusions in this range have utility for chronic or acute diseases, conditions or indications. In this way, the affinity of the AlbudAb or fusion for serum albumin can be tailored or chosen according to the disease, condition or indication to be addressed. As described above, the invention provides AlbudAbs with affinities that allow for each AlbudAb to be categorised as "high affinity", "medium affinity" or "low affinity", thus enabling the skilled person to select the appropriate AlbudAb of the invention according to the therapy at hand. See FIG. 2.

Example 9

PCT/EP2010/060112 describes $V_H$ AlbudAbs and affinity matured derivatives thereof. $V_H$ AlbudAb sequences are as follows:

```
DOM7r31 amino acid
                                     SEQ ID NO: 71
EVQLLESGGGLVQPGGSLRLSCTASGFTFRHYRMGWVRQAPGKGLEWVSWIRPDGTFT

YYADSVKGRFTISRDNSKNTLYLQMNSLRAEDTAVYYCAKSYMGDRFDYWGQGTLVTVS

S

DOM7r31 nucleic acid
                                     SEQ ID NO: 72
GAGGTGCAGCTGTTGGAGTCTGGGGGAGGCTTGGTACAGCCTGGGGGGTCCCTGCG

TCTCTCCTGTACAGCCTCCGGATTCACCTTTAGGCATTATCGTATGGGTTGGGTCCGC

CAGGCTCCAGGGAAGGGTCTAGAGTGGGTCTCATGGATTCGTCCGGATGGTACGTTT

ACATACTACGCAGACTCCGTGAAGGGCCGGTTCACCATCTCCCGCGACAATTCCAAG

AACACGCTGTATCTGCAAATGAACAGCCTGCGTGCCGAGGACACCGCGGTATATTACT

GTGCGAAATCTTATATGGGTGATAGGTTTGACTACTGGGGTCAGGGAACCCTGGTCAC

CGTCTCGAGCG

DOM7r-31-14 amino acid
                                     SEQ ID NO: 73
EVQLLESGGGLVQPGGSLRLSCTASGFTFRHYRMGWVRQAPGKGLEWVSWIRPDGTFT

YYADSVKGRFTISRDNSKNTLYLQMNSLRAEDTAVYYCAKSYMADRFDYWGQGTLVTVS

S

DOM7r-31-14 nucleic acid
                                     SEQ ID NO: 74
GAGGTGCAGCTGTTGGAGTCTGGGGGAGGCTTGGTACAGCCTGGGGGGTCCCTGCG

TCTCTCCTGTACAGCCTCCGGATTCACCTTTAGGCATTATCGTATGGGTTGGGTCCGC

CAGGCTCCAGGGAAGGGTCTAGAGTGGGTCTCATGGATTCGTCCGGATGGTACGTTT
```

-continued
```
ACATACTACGCAGACTCCGTGAAGGGCCGGTTCACCATCTCCCGCGACAATTCCAAG

AACACGCTGTATCTGCAAATGAACAGCCTGCGTGCCGAGGACACCGCGGTATATTACT

GTGCGAAATCTTATATGGCTGATAGGTTTGACTACTGGGGTCAGGGAACCCTGGTCAC

CGTCTC

GAGC
```

DOM7h-92 amino acid
SEQ ID NO: 75
```
EVQLLESGGGLVQPGGSLRLSCAASGFTFANATMSWVRQAPGKGLEWVSDIDQVGHAT

YYADSVKGRFTISRDNSKNTLYLQMNSLRAEDTAVYYCAKYSWHPDLFDYWGQGTLVTV

SS
```

DOM7r-92 nucleic acid
SEQ ID NO: 76
```
GAGGTGCAGCTGTTGGAGTCTGGGGGAGGCTTGGTACAGCCTGGGGGGTCCCTGCG

TCTCTCCTGTGCAGCCTCCGGATTCACCTTTGGGAATTATAGGATGACTTGGGTCCGC

CAGGCTCCAGGGAAGGGTCTAGAGTGGGTCTCAACTATTTCTCCTTTGGGTACGTATA

CATACTACGCAGACTCCGTGAAGGGCCGGTTCACCATCTCCCGCGACAATTCCAAGA

ACACGCTGTATCTGCAAATGAACAGCCTGCGTGCCGAGGACACCGCGGTATATTACT

GTGCGAAAGGGCGTTGGTCGATTTTTGACTACTGGGGTCAGGGAACCCTGGTCACCG

TCTCGAGC
```

DOM7r-92-4 amino acid
SEQ ID NO: 77
```
EVQLLESGGGLVQPGGSLRLSCAASGFTFDTSSMLWVRQAPGKGLEWVSVIHQSGTPTY

YADSVKGRFTISRDNSKNTLYLQMNSLRAEDTAVYYCAKFPSTHGKFDYWGQGTLVTVSS
```

DOM7r-92-4 nucleic acid
SEQ ID NO: 78
```
GAGGTGCAGCTGTTGGAGTCTGGGGGAGGCTTGGTACAGCCTGGGGGGTCCCTGCG

TCTCTCCTGTGCAGCCTCCGGATTCACCTTTGATACGAGTAGTATGTTGTGGGTCCGC

CAGGCTCCAGGGAAGGGTCTAGAGTGGGTCTCAGTTATTCATCAGAGTGGTACGCCT

ACATACTACGCAGACTCCGTGAAGGGCCGGTTCACCATCTCCCGCGACAATTCCAAG

AACACGCTGTATCTGCAAATGAACAGCCTGCGTGCCGAGGACACCGCGGTATATTACT

GTGCGAAATTTCCGTCTACTCATGGTAAGTTTGACTACTGGGGTCAGGGAACCCTGGT

CACCGT

CTCGAGC
```

Affinity Determination:

To determine the binding affinity ($K_D$) of the VH AlbudAbs to each serum albumin; purified fusion proteins were analysed by BIAcore over albumin (immobilised by primary-amine coupling onto CM5 chips; BIAcore) using fusion protein concentrations from 5000 nM to 39 nM (5000 nM, 2500 nM, 1250 nM, 625 nM, 312 nM, 156 nM, 78 nM, 39 nM) in HBS-EP BIAcore buffer, as described above. MALLS data were obtained as described above.

Results are shown in the following tables:

TABLE 16A

|  | RSA KD (M) | HSA KD (M) | CSA KD (M) | MSA* KD (M) |
|---|---|---|---|---|
| DOM7r-92-4 | 2.6E-07 | 1.3E-07 | 9.8E-08 | 1.1E-07 |

TABLE 16B

|  | HSA | CSA | RSA | MSA | MALLS |
|---|---|---|---|---|---|
| DOM7r-92 FLAG OD | 200 nM | 170 nM | 500 nM | 2000 nM | 13 + 22 kDa dimer |

TABLE 16 C

|  | HSA KD (nM) KD | RSA KD (nM) KD | CSA KD (nM) KD | MSA KD (nM) KD | MALLS |
|---|---|---|---|---|---|
| 7r-31 | fast on/off | fast on/off | fast on/off | fast on/off | M |
| 7r31-14 | 208, 360, 1330, 1950 | 103, 90.2, 370 | no binding | 6, 12, 12 14.2 | M |

Values above represent multiple, independent measurements.

Example 10

Summary of HSA Epitope Mapping with AlbudAbs

The epitopes of AlbudAb Vk molecules on HSA were determined using three orthogonal techniques: hydrogen deuterium exchange mass spectrometry, site directed mutagenesis and structure determination by x-ray crystallography.

1.0 EPITOPE MAPPING BY HYDROGEN DEUTERIUM (H/D) EXCHANGE 1.1 Protein Preparation Domain 2 of HSA (defined as amino acid residues 188-384 of HSA; SEQ ID NO: 79 and 80 for amino acid and DNA sequences for HSA Domain 2 respectively; SEQ ID NO: 81 and 82 for amino acid and DNA sequence of full length HSA respectively) were expressed in *Pichia* using the pPICZα expression system (Invitrogen) and purified using Prometic Technologies Mimetic Blue™ according to the manufacturer's instructions. DOM7h-11-3, DOM7h-14-10 and DOM7r-92-4 (SEQ ID NOs: 2, 45, 46 for amino acid and 4, 47, 48 for DNA sequences respectively). was expressed in *E. coli* strain HB2151 using an auto-induction expression system. In some instances, the cloning strategy resulted in additional N and C terminal residues (see SEQ ID NOs: 121 and 122, for example). The expressed AlbudAbs were purified from clarified supernatants by Protein-L (DOM7h-11-3 and DOM7h-14-10) or Protein-A (DOM7h-92-4) affinity chromatography using established protocols.

Expression and purification of final protein preparations of HSA Domain 2 and AlbudAbs were confirmed by SDS-PAGE analysis.

1.2 Experimental Method and General Principles

Methods and principles on using H/D exchange perturbation for epitope mapping are discussed in a review by Hamuro et al (2003), J. Biomol. Tech. 2003, 14, 171-182; and Coales et al (2009), Rapid Communications in Mass Spectrometry 2009 March; 23(5):639-47. For the epitope mapping of HSA, H/D exchange analysis of the antigen in the presence and absence of AlbudAb was carried out. The regions of HSA which exchange slower in the presence of each AlbudAb compared to speed of exchange when the AlbudAb is absent is considered to define the epitope on HSA. To identify the epitope one requires firstly the identification of proteolytic fragments of the antigen and secondly the determination of the perturbation of the H/D exchange reaction. Suitable methods are described, for example, in U.S. Pat. No. 6,291,189, U.S. Pat. No. 6,331,400 and U.S. Pat. No. 7,280,923.

After each H/D exchange reaction HSA was digested with pepsin. The digested mixture was separated by HPLC. Each HSA peptic fragment was then analyzed by mass spectrometry to determine the degree of deuterium incorporation upon the H/D exchange reaction. To obtain optimal coverage of the HSA sequence a maximum possible number of peptic fragments were followed. For the H/D exchange experiments in the presence of AlbudAb, the mixture of antigen and antibody was digested together. The peptic digest fragment mixture of the complex contained both AlbudAb and HSA fragments.

As an excess amount of an AlbudAb over HSA was used, a large amount of AlbudAb originated peptides may interfere with the mass detection of antigen originated peptides by ion competition. For this reason the least possible amount of excess antibody was used Stock solutions of 199 µM DOM7h-11-3, 199 µM DOM7h-14-10, 547 µM DOM7r-92-4 and 45 µM HSA were used in the H/D exchange experiments. 24 µl of HSA stock+ 36 µl of DOM7h-11-3; 49.5 µl of HSA stock+10.5 µl of DOM7r-92-4; 74 µl of HSA stock+20 µl of DOM7h-14-10 were used to make a complexation mixtures (final concentrations of HSA:DOM7h-11-3=17.9 µM:119.4 µM; HSA:DOM7h-14-10=35.0 µM:42.0 µM; HSA:DOM7r-92-4=37.1 µM:95.7 µM equivalent to 1:6.7, 1:1.2, 1:2.6 ratio respectively). For the control reactions either HSA or AlbudAb were replaced with PBS.

10 µl of HSA+DOM7h-11-3 complexation mixture was added to 10 µl of PBS made with $D_2O$; 5 or 8 µl of HSA:DOM7h-14-10 complexation mixture was added to 12 or 15 µl of PBS made with $D_2O$; 5 µl of HSA+DOM7r-92-4 complexation mixture was added to 15 µl of PBS made with $D_2O$. All deuteration reactions were incubated for 500 seconds at 0° C. After incubation all 20 µl of the complexation mixture was mixed with 30 µl of quenching solution (2M Urea, 1M TCEP pH3.0). 45 µl of the quenched reaction mixture was injected onto a proprietary proteolysis/HPLC system and fragments analysed by mass spectrometry 1.3 Perturbation Results Fragments were identified, data deconvoluted and visualized using proprietary software (ExSAR). A summary of epitope hits based on H/D exchange perturbation data are highlighted in Table 17 below.

Based on data summarized in Table 17(A), (B) and (C) it was concluded that segments which showed significant perturbation (on average>20%) of deuteration could define the epitope. The sequence segments identified are highlighted in FIG. 3.

2.0 ALANINE SCANNING SITE DIRECTED MUTAGENESIS (SDM)

Target residues for SDM for Alanine scanning were selected based on 3 criteria: (1) H/D exchange perturbation data above, (2) surface accessibility of side chains based on a previously published crystal structure of HSA (1 BKE.pdb (RCSB Protein DataBank)) and (3) charge or size of side chains.

2.1 Cloning and Expression of Alanine Mutants

The wild type template of HSA was PCR-cloned into a mammalian expression vector using standard molecular biology protocols. A 6-Histidine tag was fused to the C-terminus of the sequence (SEQ ID NOS: 25 and 34 for amino acid and DNA sequences respectively for the WT HSA-$His_6$ construct) for nickel affinity purification. Primer pairs used for PCR amplification to make the WT expression construct were TB147 and TB148 (SEQ ID NOS: 85 and 86 respectively).

Mutants were made following standard molecular biology protocols using the WT HSA-$His_s$ construct as a template for mutagenesis. The list of Alanine mutants and mutagenesis oligo pairs used to construct them are listed in Table 18 below.

TABLE 18

Primers pairs for making HSA mutants.

| | | | | |
|---|---|---|---|---|
| K225A | TB153 | GAGCCAGAGATTTCCCGCCGCTGAGTTT GCAGAAG | sense | SEQ ID NO: 87 |
| | TB154 | CTTCTGCAAACTCAGCGGCGGGAAATCT CTGGCTC | anti-sense | SEQ ID NO: 88 |
| E227A | TB155 | GAGATTTCCCAAAGCTGCCTTTGCAGAA GTTTCCAAG | sense | SEQ ID NO: 89 |
| | TB156 | CTTGGAAACTTCTGCAAAGGCAGCTTTG GGAAATCTC | anti-sense | SEQ ID NO: 90 |
| E230A | TB157 | CCAAAGCTGAGTTTGCAGCCGTTTCCAA GTTAGTGAC | sense | SEQ ID NO: 91 |
| | TB158 | GTCACTAACTTGGAAACGGCTGCAAACT CAGCTTTGG | anti-sense | SEQ ID NO: 92 |
| D314A | TB159 | GATTTTGTTGAAAGTAAGGCCGTTTGCA AAAACTATG | sense | SEQ ID NO: 93 |
| | TB160 | CATAGTTTTTGCAAACGGCCTTACTTTCA ACAAAATC | anti-sense | SEQ ID NO: 94 |
| K317A | TB161 | GAAAGTAAGGATGTTTGCGCCAACTATG CTGAGGCAAAGG | sense | SEQ ID NO: 95 |
| | TB162 | CCTTTGCCTCAGCATAGTTGGCGCAAAC ATCCTTACTTTC | anti-sense | SEQ ID NO: 96 |
| V325A | TB163 | GCTGAGGCAAAGGATGCCTTCCTGGGC ATGTTTTTG | sense | SEQ ID NO: 97 |
| | TB164 | CAAAAACATGCCCAGGAAGGCATCCTTT GCCTCAGC | anti-sense | SEQ ID NO: 98 |
| M329A | TB165 | GGATGTCTTCCTGGGCGCCTTTTTGTAT GAATATG | sense | SEQ ID NO: 99 |
| | TB166 | CATATTCATACAAAAAGGCGCCCAGGAA GACATCC | anti-sense | SEQ ID NO: 100 |
| K351A | TB167 | GCTGCTGCTGAGACTTGCCGCCACATAT GAAACCACTCTAG | sense | SEQ ID NO: 101 |
| | TB168 | CTAGAGTGGTTTCATATGTGGCGGCAAG TCTCAGCAGCAGC | anti-sense | SEQ ID NO: 102 |

Sequence verified clones were selected from plasmid DNA minipreps made using Millipore Montage kits following the manufacturers protocols. Amino acid and DNA sequences of constructs are summarized in Table 19 below.

TABLE 19

List of HSA mutants made

| HSA-His6 | Amino Acid | DNA |
|---|---|---|
| WT | SEQ ID 103 | SEQ ID 112 |
| K225A | SEQ ID 104 | SEQ ID 113 |
| E227A | SEQ ID 105 | SEQ ID 114 |
| E230A | SEQ ID 106 | SEQ ID 115 |
| D314A | SEQ ID 107 | SEQ ID 116 |
| K317A | SEQ ID 108 | SEQ ID 117 |
| V325A | SEQ ID 109 | SEQ ID 118 |
| M329A | SEQ ID 110 | SEQ ID 119 |
| K351A | SEQ ID 111 | SEQ ID 120 |

His$_6$-tagged WT HSA and mutants were expressed in mammalian HEK293-6E cells using transient transfection techniques. Mutants and WT HSA were purified from clarified expression supernatants using nickel affinity chromatography according to established protocols. SDS-PAGE analysis of the purified mutants showed >95% purity.

2.2 BIAcore Analysis of Alanine Mutants
2.2.1 Experimental Method for BIAcore

Briefly, WT HSA and mutants were immobilised onto CM5 Biacore chips on a Biacore 3000 (GE Healthcare). This was performed by first activating all four flow cells with EDC/NHS and then injecting WT HSA or mutants in acetate buffer pH 4.5. Any free sites on the chip were then blocked with an injection of ethanolamine across all four flow cells. Levels of immobilization are for each sample are summarized in Table 20 below.

TABLE 20

BIAcore CM5 chip preparation.

| | | | |
|---|---|---|---|
| Chip1 | Fc2 | E227A HSA | 312RUs |
| | Fc4 | WT HSA | 293RUs |
| Chip2 | Fc2 | D314A HSA | 369RU |
| | Fc3 | K225A HSA | 143RU |
| | Fc4 | E230A HSA | 339RU |
| Chip3 | Fc2 | M324A HSA | 167RU |
| | Fc3 | V325A HSA | 147RU |
| | Fc4 | WT HSA | 304RU |

TABLE 20-continued

| BIAcore CM5 chip preparation. | | | |
|---|---|---|---|
| Chip4 | Fc2 | K317A HSA | 305RU |
| | Fc3 | K351A HSA | 165RU |
| | Fc4 | WT HSA | 223RU |

2.2.2 BIAcore Data

Flow rate using HBS-EP buffer was 40 uL/min and the purified dAb proteins were injected for 1 minute at concentrations 5000 nM followed by 7 further injections at a sequential 1:2 dilution in mobile phase.

Analysis and determination of equilibrium binding constants (KD) was performed using standard procedures.

TABLE 21 A

| | DOM7h-14-10myc | | DOM7h-11-15myc | | DOM7h-11-3myc | |
|---|---|---|---|---|---|---|
| HSA mutant | nM | x-fold decrease in binding | nM | x-fold decrease in binding | nM | x-fold decrease in binding |
| K225A | 2.34E-09 | 0.31 | 1.17E-09 | 0.53 | 2.41E-08 | 0.90375 |
| E227A | 3.33E-08 | 4.44 | 7.91 E-09 | 3.58 | 1.46E-07 | 5.475 |
| E230A | 1.50E-08 | 2.00 | 2.45E-08 | 11.09 | 8.00E-07 | 30 |
| D314A | 5.35E-09 | 0.71 | 4.45E-09 | 2.01 | 1.78E-08 | 0.6675 |
| M329A | 5.65E-09 | 0.75 | 5.72 E-09 | 2.59 | 6.52E-07 | 24.45 |
| WT | 7.5E-09 | | 2.21E-09 | | 2.66667E-08 | |

TABLE 21B

| | DOM7r92-4myc | | DOM7r31-14myc | |
|---|---|---|---|---|
| HSA mutant | nM | x-fold decrease in binding | nM | x-fold decrease in binding |
| K225A | 3.49E-08 | 0.71 | 2.49E-08 | 0.44 |
| E227A | 1.28E-07 | 2.62 | no binding | 88.81 |
| E230A | 4.06E-06 | 83.03 | 3.97E-07 | 7.05 |
| D314A | 3.45E-08 | 0.71 | 5.20E-08 | 0.92 |
| M329A | 2.75E-08 | 0.56 | 4.93E-07 | 8.76 |
| WT | 4.89E-08 | | 5.63E-08 | |

2.2.3 BIAcore Analysis and Conclusions

DOM7h-14-10: No significant decrease in binding was observed upon mutagenesis of any of the above residues in isolation.

DOM7h-11-15: Some significant decrease in binding of DOM7h-11-15 to E230A is observed (11-fold decrease in binding over WT). This suggests that residue 230 on HSA plays a significant contribution in the specific binding to human serum albumin.

DOM7h-11-3: A significant decrease in binding was observed for two residues (E230 and M324) upon mutagenesis to alanine. This suggests that these two residues play an important contribution to the Antibody/Antigen interaction.

DOM7r92-4: A significant decrease in binding for E230A was observed.

DOM7r31-14: A significant decrease in binding for E227A was observed.

3 CRYSTAL STRUCTURE OF THE DOM7H-11-15/HSA COMPLEX 3.1 Protein Preparation

Fatty acid free HSA from a commercial source was purified by size exclusion chromatography to >95% purity as judged by SDS-PAGE.

DOM7h-11-15 (SEQ ID NO: 1 and SEQ ID NO: 2 for amino acid and DNA sequences respectively) was expressed in E. coli strain BL21DE3 using an auto-induction expression system. DOM7h-11-15 was purified from clarified supernatants by Protein-L affinity chromatography using established protocols. It was further purified by ion exchange chromatography using a Hi-Trap SP column using established protocols.

HSA was mixed with DOM7h-11-15 and the complex purified by size exclusion chromatography. Protein was concentrated in 20 mM Tris-Cl pH 8.0 prior to crystallization screening.

3.2 Crystallization

The HSA/DOM7h-11-15 complex was put into a crystallization screen with approximately 1200 conditions using the sitting drop method.

3.3 X-Ray Diffraction Data Collection and Processing

HSA/DOM7h-11-15 crystals were flash frozen in liquid nitrogen after cryoprotection. The crystal was maintained at 100K during data collection. X-ray diffraction data were collected at the SWISS LIGHT SOURCE (SLS, Villigen, Switzerland).

Data were processed using XDS and XSCALE (Kabsch) reviewed, for example, in Acta Crystallogr D Biol Crystallogr. 2010 Feb. 1; 66(Pt 2): 125-132). The crystals belonged to the space group $P2_12_12_1$ with two complexes HSA/DOM7h-11-15 in the asymmetric unit.

Data collection statistics are summarised in Table 22 below.

TABLE 22

| Data Collection and Processing Statistics for HSA/DOM7h-11-15 complex Crystal | |
|---|---|
| Complex | HSA-DOM7h11-15 |
| X-ray source | PX1/X056A (SLS[1]) |
| Wavelength [Å] | 1.0000 |
| Detector | PILATUS 5M |
| Temperature [K] | 100 |
| Space group | $P 2_1 2_1 2_1$ |
| Cell: a; b; c [Å] | 102.15; 110.00; 141.34 |
| A; β; γ [°] | 90.0; 90.0; 90.0 |
| Resolution [Å] [2] | 2.50 (2.91-2.66) |
| Unique reflections [2] | 55.052 (10.796) |
| Multiplicity [2] | 5.3 (5.5) |
| Completeness [%] [2] | 98.7 (100.0) |
| $R_{sym}$ [%] [2, 3] | 10.0 (43.9) |
| $R_{meas}$ [%] [2, 4] | 11.1 (48.3) |
| mean(I)/sigma [2,5] | 12.17 (4.63) |

[1]SWISS LIGHT SOURCE (SLS, Villigen, Switzerland)
[2] Numbers in brackets correspond to the resolution bin with $R_{sym}$ = 43.9%.
[3]

$$R_{sym} = \frac{\sum_h \sum_i^{n_h} |\hat{I}_{h} - I_{h,i}|}{\sum_h^{n_h} I_{h,i}} \text{ with } \hat{I}_h = \frac{1}{n_h} \sum_i^{n_k} I_{h,i}$$

Where $I_{h,i}$ is the intensity value of the ith measurement of h

[4]

TABLE 22-continued

Data Collection and Processing Statistics for
HSA/DOM7h-11-15 complex Crystal

| Complex | HSA-DOM7h11-15 |
|---|---|

$$R_{meas} = \frac{\sum_h \sqrt{\frac{n_h}{n_h-1}} \sum_i^{n_h} |\hat{I}_h - I_{h,i}|}{\sum_h \sum_i^{n_h} I_{h,i}} \text{ with } \hat{I}_h = \frac{1}{n_h} \sum_i^{n_h} I_{h,i}$$

Where $I_{h,i}$ is the intensity value of the ith measurement of h
[5] Calculated from independent reflections

3.4 Structure Determination and Model Refinement

Structure determination and model refinement was carried out to generate a representation of HSA in complex with DOM 7h-11-15.

The structure of the complex was determined by molecular replacement. DOM7h11-15 bound to HSA showed clear electron density in the initial maps from phases determined from the HSA molecules only and allowed unambiguous placement of the antibody domain using a difference maps. Subsequent model building and refinement was performed according to standard protocols with the software packages in CCP4 and COOT (see Collaborative Computational Project, Number 4. 1994.

"The CCP4 Suite: Programs for Protein Crystallography". Acta Cryst. D50, 760-763; and "Coot: model-building tools for molecular graphics" Emsley P, Cowtan K Acta Crystallographica Section D-Biological Crystallography 60: 2126-2132 Part 12 Sp. Iss. 1 Dec. 2004, for example). Refinement statistics are summarized in Table 23

The Ramachandran Plot of the final model shows 91.5% of all residues in the most favoured region, 8.1% in the additionally allowed region, 0.4% of the residues in the generously allowed, and no residues in the disallowed regions (Modelling statistics are summarized in Table 23).

TABLE 23

Refinement and Modelling Statistics for the HSA/DOM7h-11-15 Structure

| Complex | HSA-DOM7h11-15 |
|---|---|
| Resolution [Å] | 86.71-2.50 |
| Number of reflections (working/test) | 54,062/989 |
| $R_{cryst}$[%] | 23.8 |
| $R_{free}$[2] [%] | 28.5 |
| Total number of atoms: | |
| Protein | 10,881 |
| Water | 103 |
| Ligand | — |
| Sulphate | 60 |
| 1,2-Ethanediol | 16 |
| Deviation from ideal geometry:[3] | |
| Bond lengths [Å] | 0.008 |
| Bond angles [°] | 1.06 |
| Bonded B's[4][Å$^2$] | 1.7 |
| Ramachandran Plot:[5] | |
| Most favoured regions | 92.0 |
| Additional allowed regions | 7.7 |
| Generously allowed regions | 0.3 |
| Disallowed regions | 0.0 |

[1]Values as defined in REFMAC5, without sigma cut-off
[2]Test-set contains 1.8% of measured reflections
[3]Root mean square deviations from geometric target values
[4]Calculated with programme MOLEMAN
[5]Calculated with programme PROCHECK

3.5 Structure Analysis
3.5.1 Overall Structure

Figure 4A:
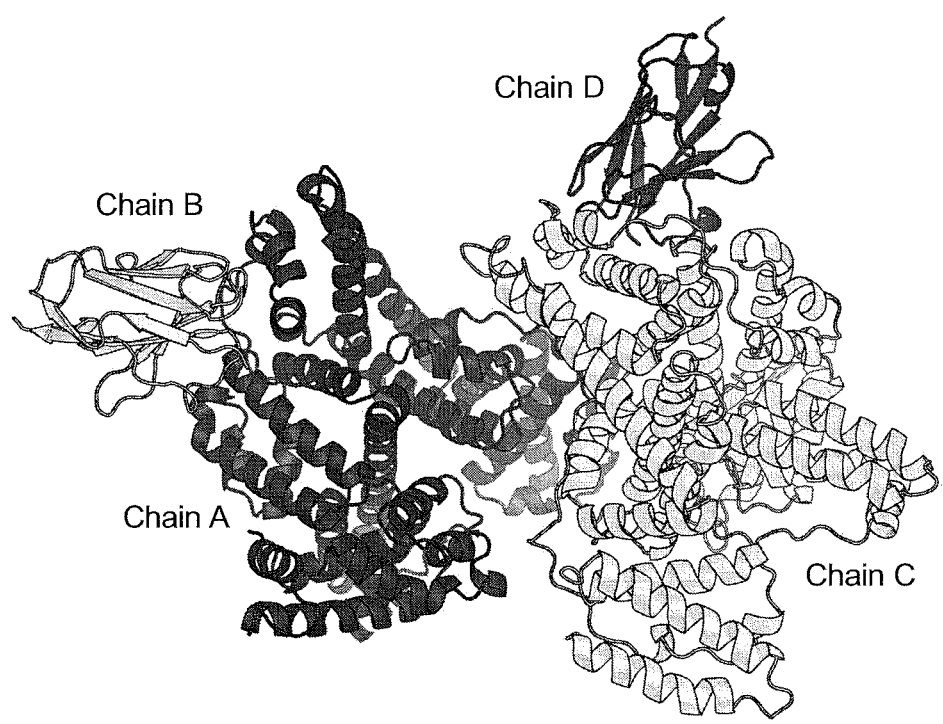
FIG. 4A shows the asymmetric unit.
Figure 4B:
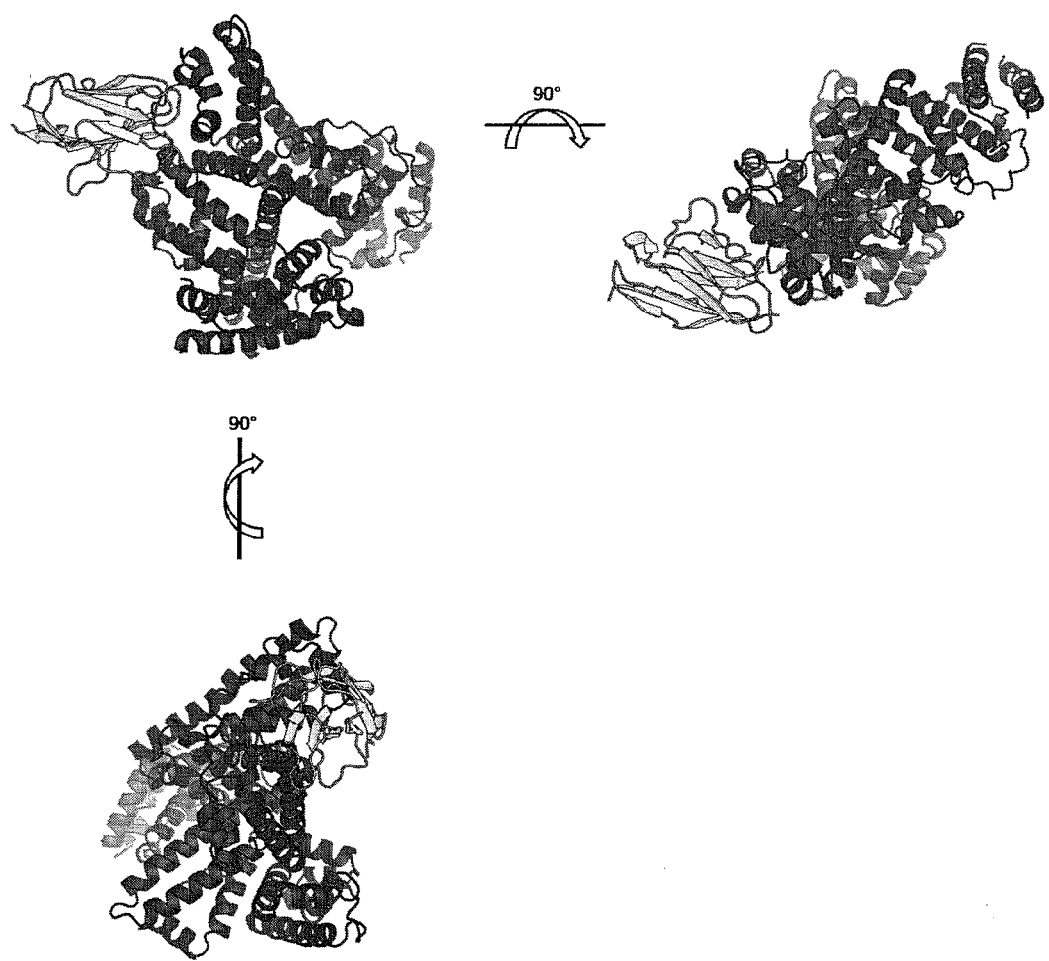
FIG. 4B shows biologically relevant complex in 3 different orientations.
Figure 4C:
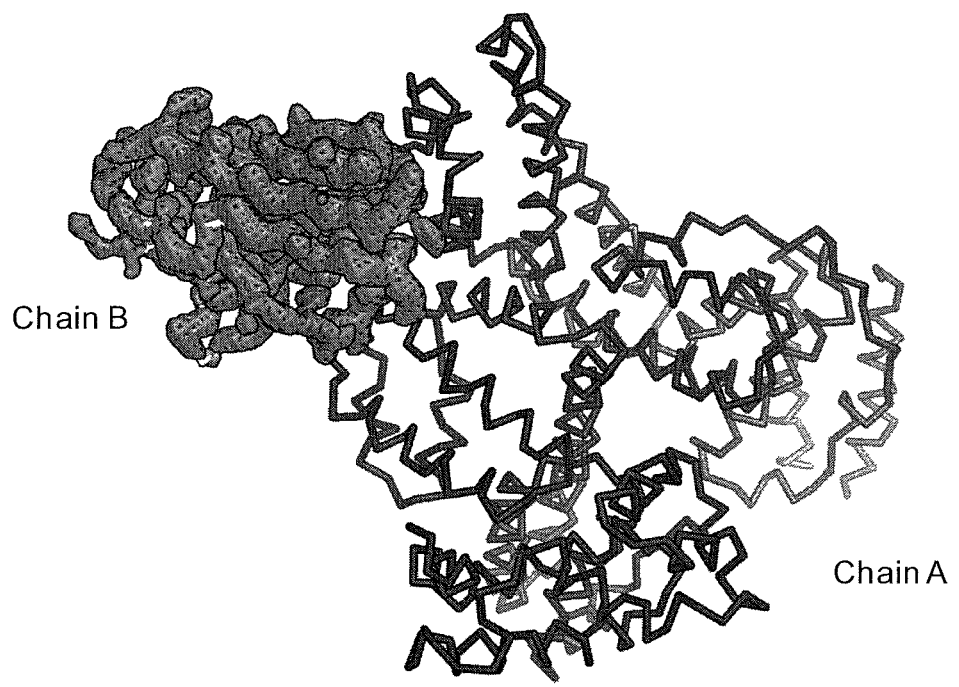
FIG. 4C shows electron density map for DOM7h-11-15 calculated from phases from the final model contoured at 2.06.

The structure of HSA in complex with DOM7h11-15 is represented in FIG. 4. FIG. 4A shows the asymmetric unit containing 2 copies each of HSA and DOM7h-11-15. The biologically relevant unit which consists of one molecule each of HSA and DOM7h-11-15 is shown in two orientations in FIG. 4B.

3.5.2 The Epitope and Paratope

Figure 5:
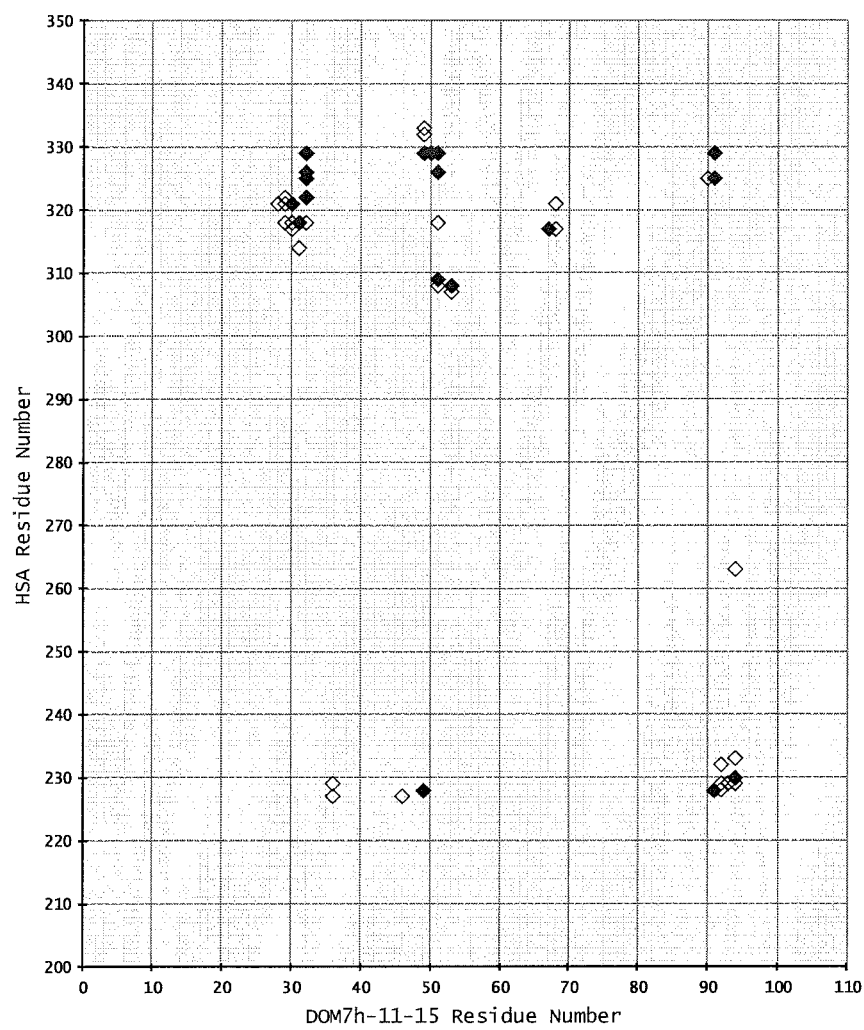
FIG. 5: Grid showing contacting residues between HSA and DOM7h-11-15.
Figure 7A:
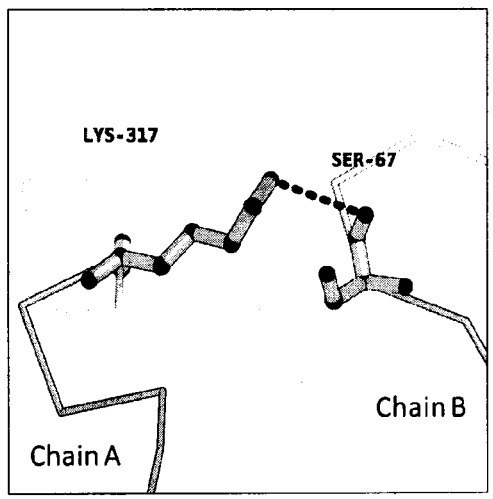
FIG. 7: Detail of interactions between HSA and DOM7h-11-15.
Figure 7B:
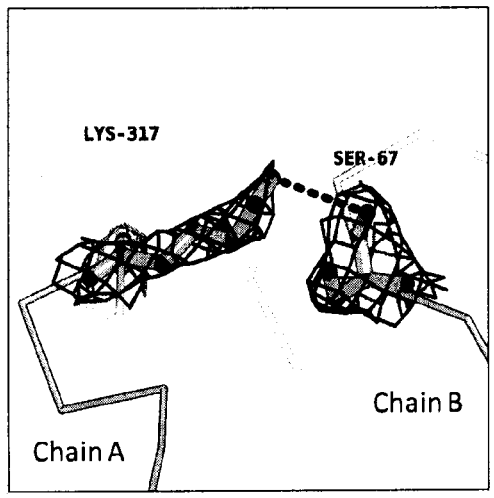
Figure 7C:
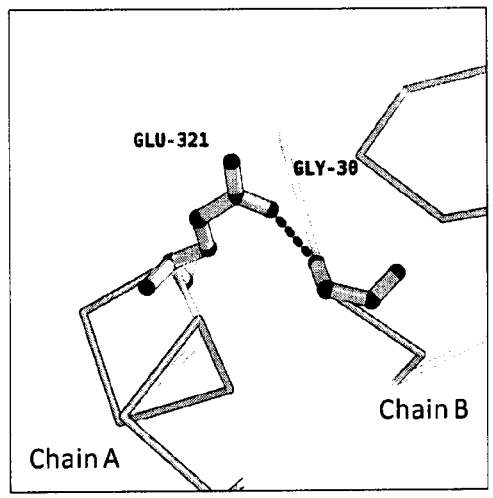
Figure 7D:
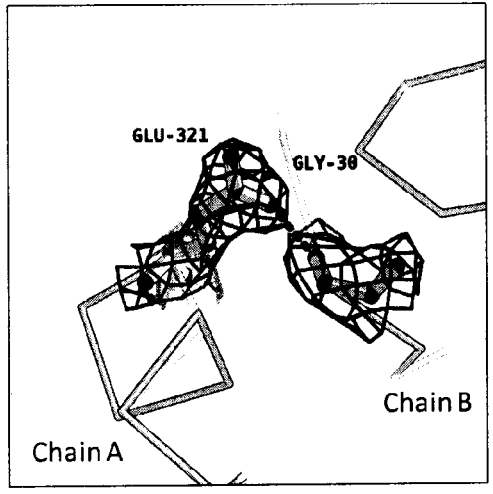
Figure 7E:
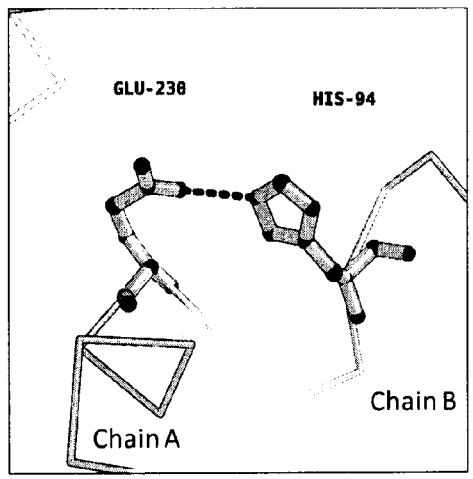
Figure 7F:
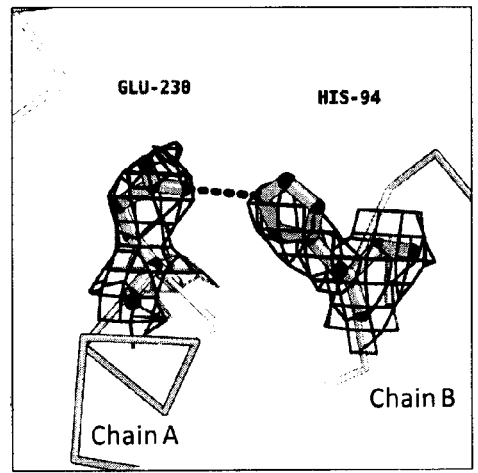
Figure 7G:
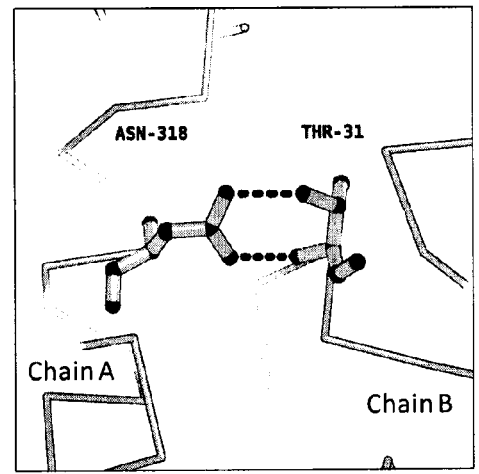
Figure 7H:
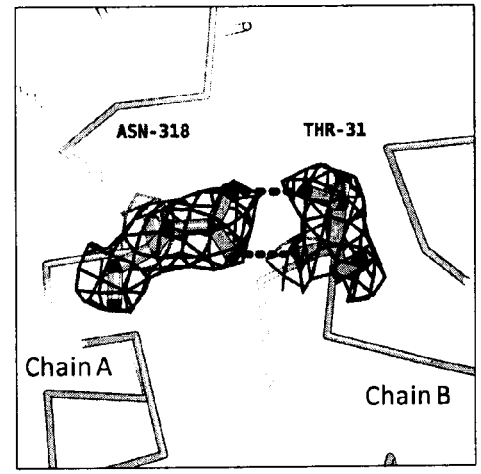
Figure 7I:
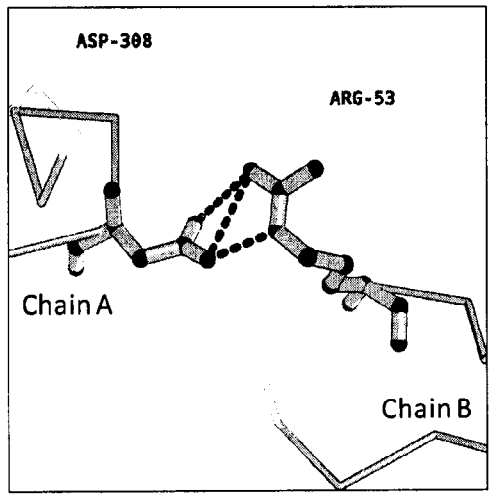
Figure 7J:
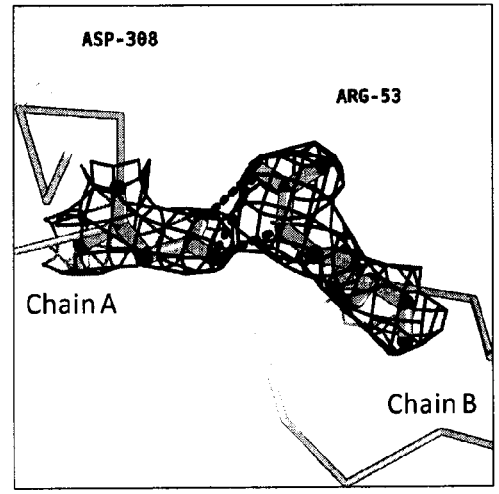
Figure 7K:
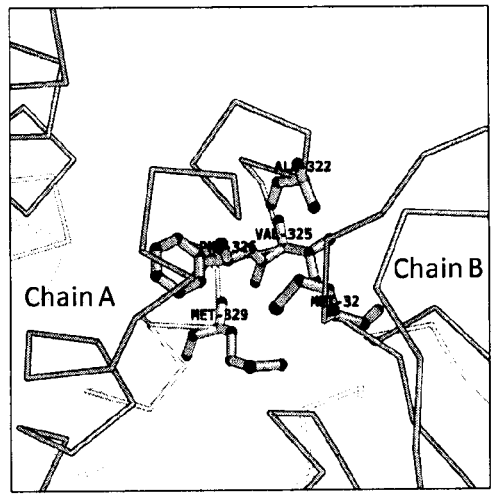
Figure 7L:
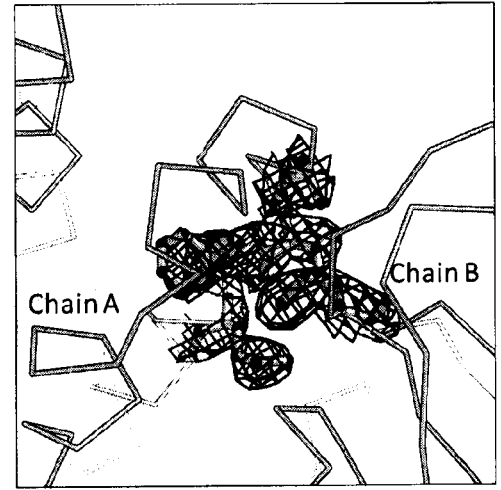
Figure 7M:
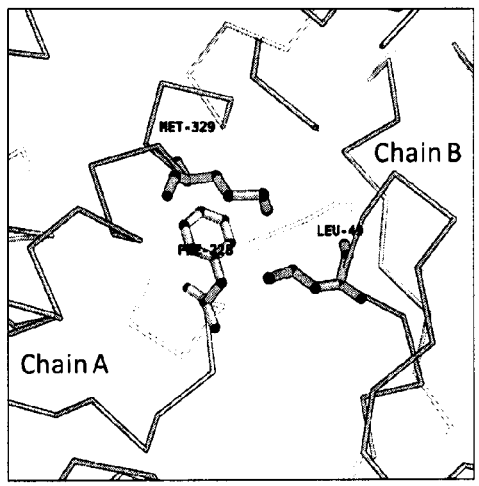
Figure 7N:
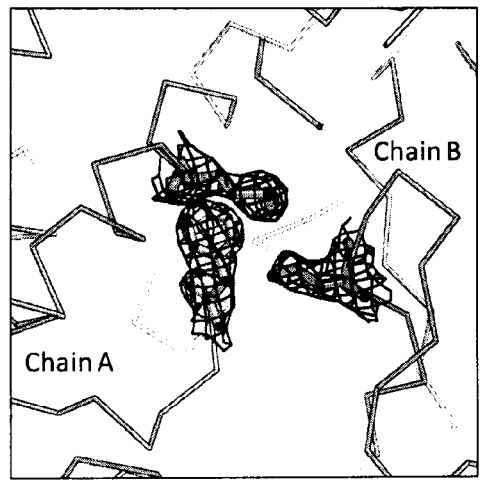
Figure 7O:
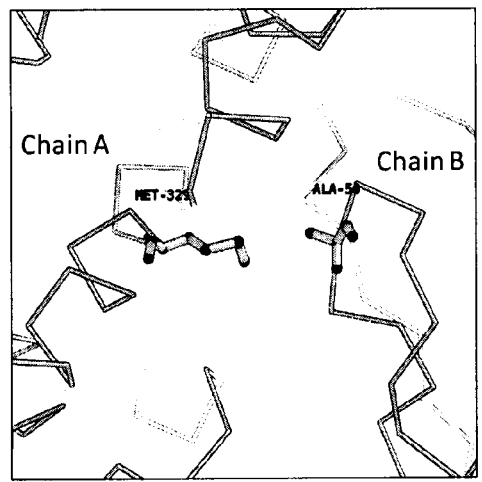
Figure 7P:
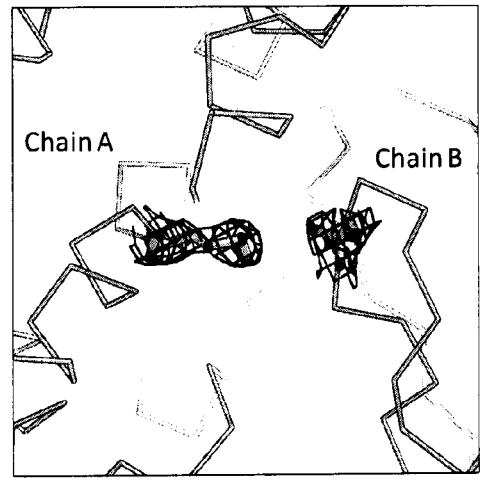
Figure 7Q:
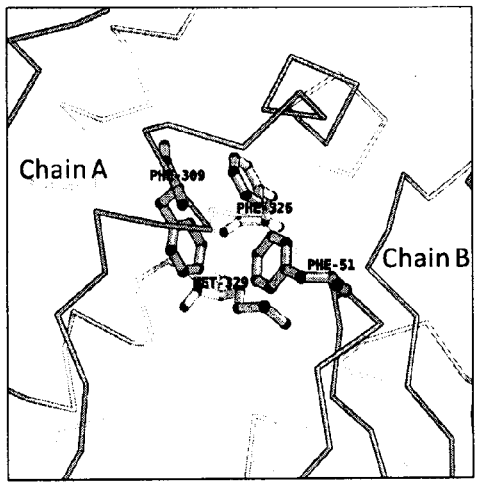
Figure 7R:
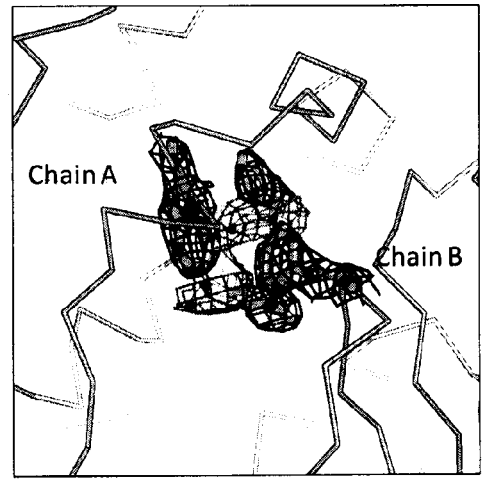
Figure 7S:
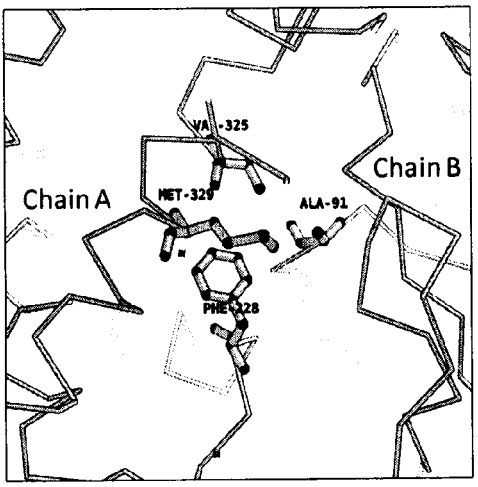
Figure 7T:
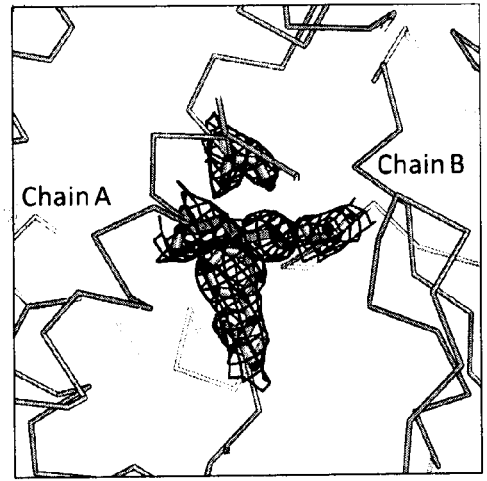

Residues on the HSA-Albudab binding interface are displayed in a format by residue number in FIG. 5 (this figure lists all residue to residue contacts within 4.5 Å between chains A (HSA) and chain B (DOM7h-11-15)). All significant interaction pairs are marked as solid diamonds. Types of interactions for those considered to significant are listed in Table 22.

TABLE 22A

List of interactions between HSA and DOM7h-11-15

| HSA | | | DOM7h-11-15 | | |
|---|---|---|---|---|---|
| Chain | Residue Number | Residue Type | Chain | Residue Number | Residue Type | Interaction |
| A | 228 | (PHE) | B | 49 | (LEU) | hydrophobic |
| A | 228 | (PHE) | B | 91 | (ALA) | hydrophobic |
| A | 230 | (GLU) | B | 94 | (HIS) | 1 H-bond SC-SC |
| A | 308 | (ASP) | B | 53 | (ARG) | 3 H-bonds all SC-SC |
| A | 309 | (PHE) | B | 51 | (PHE) | hydrophobic |
| A | 317 | (LYS) | B | 67 | (SER) | 1 H-bond SC-MC |
| A | 318 | (ASN) | B | 31 | (THR) | 2 H-bond MC-SC,SC-SC |
| A | 321 | (GLU) | B | 30 | (GLY) | 1 H-bond MC-SC |
| A | 322 | (ALA) | B | 32 | (MET) | hydrophobic |
| A | 325 | (VAL) | B | 32 | (MET) | hydrophobic |
| A | 325 | (VAL) | B | 91 | (ALA) | hydrophobic |
| A | 326 | (PHE) | B | 32 | (MET) | hydrophobic |
| A | 326 | (PHE) | B | 51 | (PHE) | hydrophobic |
| A | 329 | (MET) | B | 32 | (MET) | hydrophobic |
| A | 329 | (MET) | B | 49 | (LEU) | hydrophobic |
| A | 329 | (MET) | B | 50 | (ALA) | hydrophobic |
| A | 329 | (MET) | B | 51 | (PHE) | hydrophobic |
| A | 329 | (MET) | B | 91 | (ALA) | hydrophobic |

All but two DOM7h-11-15 residues binding HSA are from CDR1, 2 and 3. Residues forming the paratope are showing in the alignment in FIG. 6 below where DOM7h-11-3, DOM7h11-15 are aligned against Vk dummy (VKDUM-1). Table 22B below lists additional residues on the AlbudAb-HSA interface within 4.5 Å.

TABLE 22B

Table of additional residues on interface

| HSA | | | DOM7h-11-15 | | |
|---|---|---|---|---|---|
| Chain | Residue number | Residue number | Chain | Residue number | Residue number |
| A | 227 | (GLU) | B | 36 | (TYR) |
| A | 227 | (GLU) | B | 46 | (LEU) |
| A | 228 | (PHE) | B | 92 | (GLY) |
| A | 229 | (ALA) | B | 36 | (TYR) |
| A | 229 | (ALA) | B | 92 | (GLY) |
| A | 229 | (ALA) | B | 93 | (THR) |
| A | 229 | (ALA) | B | 94 | (HIS) |
| A | 232 | (SER) | B | 92 | (GLY) |
| A | 233 | (LYS) | B | 94 | (HIS) |

TABLE 22B-continued

Table of additional residues on interface

| HSA | | | DOM7h-11-15 | | |
|---|---|---|---|---|---|
| Chain | Residue number | Residue number | Chain | Residue number | Residue number |
| A | 263 | (TYR) | B | 94 | (HIS) |
| A | 307 | (ALA) | B | 53 | (ARG) |
| A | 308 | (ASP) | B | 51 | (PHE) |
| A | 314 | (ASP) | B | 31 | (THR) |
| A | 317 | (LYS) | B | 30 | (GLY) |
| A | 317 | (LYS) | B | 68 | (GLY) |
| A | 318 | (ASN) | B | 29 | (ILE) |
| A | 318 | (ASN) | B | 30 | (GLY) |
| A | 318 | (ASN) | B | 32 | (MET) |
| A | 318 | (ASN) | B | 51 | (PHE) |
| A | 321 | (GLU) | B | 28 | (PRO) |
| A | 321 | (GLU) | B | 29 | (ILE) |
| A | 321 | (GLU) | B | 68 | (GLY) |
| A | 322 | (ALA) | B | 29 | (ILE) |
| A | 325 | (VAL) | B | 90 | (GLN) |
| A | 332 | (TYR) | B | 49 | (LEU) |
| A | 333 | (GLU) | B | 49 | (LEU) |

Significant interactions listed in Table 22 are detailed further in FIG. 7 and panels within. In these figures, interacting residues are drawn in stick representation with any hydrogen bonds drawn as dashed lines. Corresponding electron density for those interacting side chains are also show depicted in mesh (contoured at 1.5σ).

4.0 CONCLUSIONS

Figure 8:
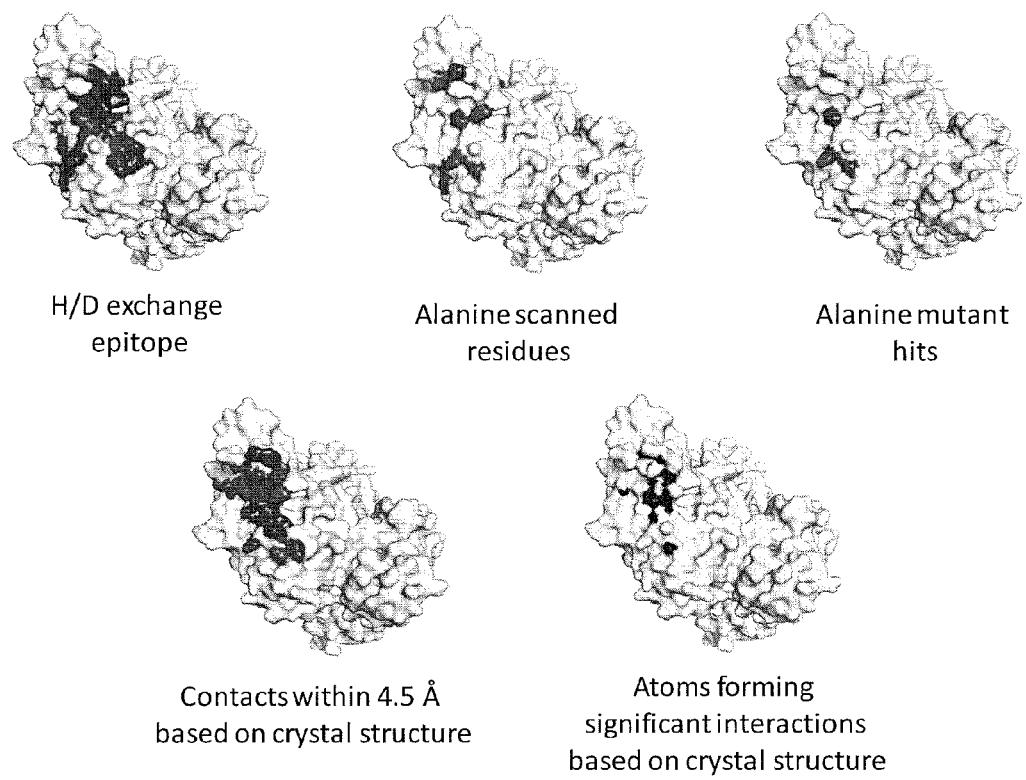
FIG. 8: Comparison of epitope data from orthogonal techniques. HSA is rendered in surface representation and dark patches depict epitope regions identified using each technique.

Three orthogonal techniques have been used to determine the epitope of the DOM7h-11 lineage on HSA. The results from all techniques provide information about the region of HSA which forms the epitope. Whilst H/D exchange perturbation data give a range of possible residues, Alanine scanning data and the crystal structure provide more detailed information on a single residue level. FIG. 8 below summarizes level of detail and specificity the data from each technique has provided.

Figure 9:
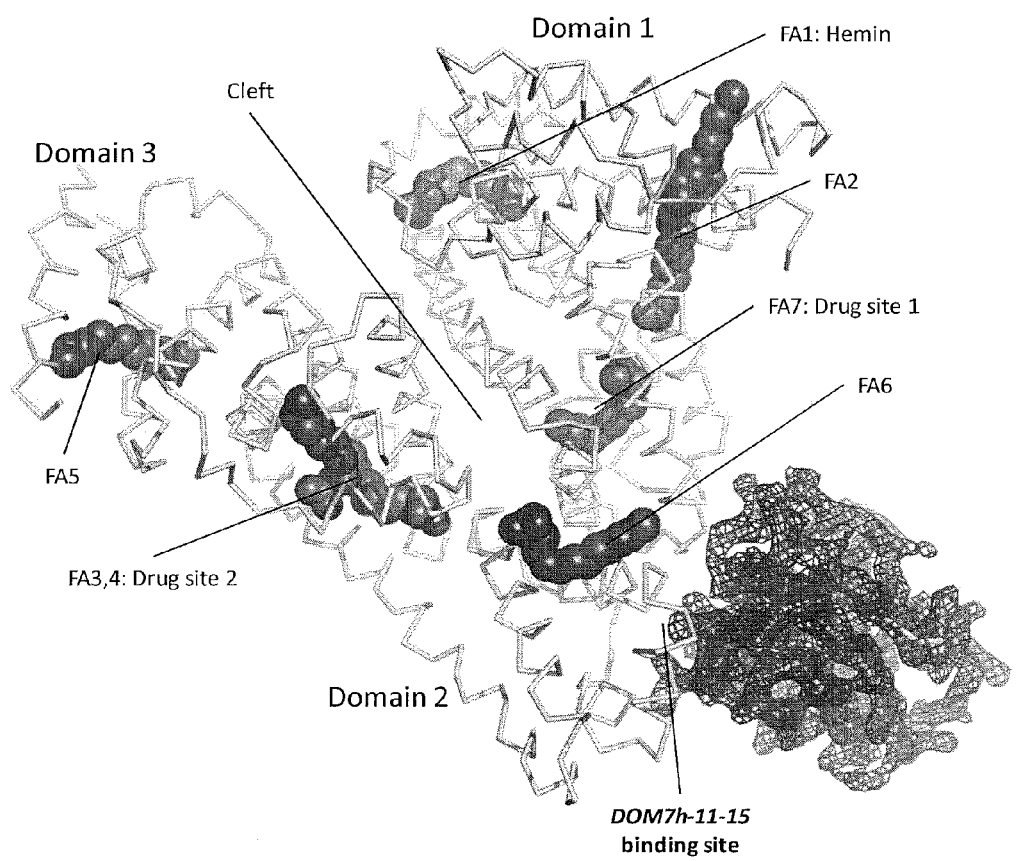
FIG. 9: Positions of lipid carrier pockets relative to DOM7h-11-15 binding site. The HSA backbone is drawn in tube representation; lipid molecules are dark spheres; electron density for DOM7h-11-15 is drawn in dark mesh. 1E7G.pdb was structurally aligned to the peptide backbone of the HSA/DOM7h-11-15 crystal structure to superimpose lipid moieties to carrier pockets (FA1-FA7: fatty acid binding sites).

Based on the crystal structure, it is also possible to state that the bind of DOM7h-11-15 to HSA does not block or obstruct any lipid carrier pockets on HSA. This is particularly relevant for therapeutic applications since these binding pockets are utilized by a number of therapeutic compounds for systemic transport. Therefore any potential biopharmaceutical formatted with DOM7h-11-15 would not be expected to interfere with HSA-drug interactions and transport. Drug/lipid carrier pocket positions relative to the DOM7h-11-15 epitope are detailed in FIG. 9. Based on the similar epitope observed with DOM7h-14-10 and DOM7r-92-4 H/D exchange perturbation data, these AlbudAbs™ would also not be expected to interfere with HSA-drug interactions and transport.

TABLE OF SEQUENCES

| | SEQ ID NO: | |
|---|---|---|
| IDENTIFIER | Amino acid | Nucleic acid |
| DOM7h-11-15 | 1 | 3 |
| DOM7h-11-3 | 2 | 4 |
| DOM7h-14/Exendin-4 fusion | 5 | 6 |
| DOM7h-14-10/Exendin-4 fusion | 7 | 8 |
| DOM7h-11/Exendin-4 fusion | 9 | 10 |
| DOM7h-11-15/Exendin-4 fusion | 11 | 12 |
| DOM7h14-10/G4SC-NCE fusion | 13 | 14 |
| DOM7h14-10/TVAAPSC fusion | 15 | 16 |
| DOM7h-11/DOM1m-21-23 fusion | 17 | 19 |
| DOM7h-11/DOM1m-21-23 fusion + myc tag | 18 | 20 |
| DOM7h-11-15/DOM1m-21-23 fusion | 21 | 23 |
| DOM7h-11-15/DOM1m-21-23 fusion + myc tag | 22 | 24 |
| DPK9 Vk dummy CDRs 1-3 | 25-27 | — |
| DOM7h-11 CDRs 1-3 | 28-30 | — |
| DOM 7h-11-15 CDRs 1-3 | 31-33 | — |
| DOM 7h-11-3 CDRs 1-3 | 34-36 | — |
| DOM 7h-14 CDRs 1-3 | 37-39 | — |
| DOM 7h-14-10 CDRs 1-3 | 40-42 | — |
| Interferon alpha 2b | 43 | 44 |
| IFNα2b SOE fragment 5' | — | 45 |
| IFNα2b SOE fragment 3' | — | 46 |
| Vk SOE fragment 5' | — | 47 |
| Vk SOE fragment 3' to also introduce a myc tag | — | 48 |
| IFNα2b SOE fragment 5' | — | 49 |
| Vk SOE fragment 3' to also introduce a myc tag | — | 50 |
| Leader sequence | 51 | 52 |
| DMS7321 (IFNα2b-DOM7h-14) + myc | 53 | 54 |
| DMS7321 (IFNα2b-DOM7h-14) no tag | 55 | 56 |
| DMS732 (IFNα2b-DOM7h-14-10) + myc | 57 | 58 |
| DMS732 (IFNα2b-DOM7h-14-10) no tag | 59 | 60 |
| DMS 7325 (IFNα2b-DOM7h-11) + myc | 61 | 62 |
| DMS 7325 (IFNα2b-DOM7h-11) no tag | 63 | 64 |
| DMS 7327 (IFNα2b-DOM7h-11-15) + myc | 65 | 66 |
| DMS 7327 (IFNα2b-DOM7h-11-15) no tag | 67 | 68 |
| DOM7h-14 R108C | 69 | 70 |
| DOM7r31 | 71 | 72 |
| DOM7r-31-14 | 73 | 74 |
| DOM7h-94 | 75 | 76 |
| DOM7r-92-4 | 77 | 78 |
| DOMAIN 2 OF HSA | 79 | 80 |
| FULL LENGTH HSA | 81 | 82 |
| DOM 7H-14-10 | 83 | 84 |
| PRIMER TB147 | — | 85 |
| PRIMER TB148 | — | 86 |
| TB153 | — | 87 |
| TB154 | — | 88 |
| TB155 | — | 89 |
| TB156 | — | 90 |
| TB157 | — | 91 |
| TB158 | — | 92 |
| TB159 | — | 93 |
| TB160 | — | 94 |
| TB161 | — | 95 |
| TB162 | — | 96 |
| TB163 | — | 97 |
| TB164 | — | 98 |
| TB165 | — | 99 |
| TB166 | — | 100 |
| TB167 | — | 101 |
| TB168 | — | 102 |
| HSA-His6 WT | 103 | 112 |
| HSA-His6 K225A | 104 | 113 |
| HSA-His6 E227A | 105 | 114 |
| HSA-His6 E230A | 106 | 115 |
| HSA-His6 D314A | 107 | 116 |
| HSA-His6 K317A | 108 | 117 |
| HSA-His6 V325A | 109 | 118 |
| HSA-His6 M329A | 110 | 119 |
| HSA-His6 K351A | 111 | 120 |
| DOM 7h-11-13 | 121 | 122 |
| DOM7H-14 | 123 | 124 |
| DOM7H-11 | 125 | 126 |

Example 11

Sequences of DOM7h-14-10 Variants

In another embodiment of the invention, listed below are the amino acid and nucleotide sequences for some variants of the anti-serum albumin immunoglobulin single variable domain DOM7h-14.

DOM7h-14-56.
(SEQ ID NO: 127)
DIQMTQSPSSLSASVGDRVTITCRASQWIGSQLSWYQQKPGKAPMLLIMW
SSSLQSGVPSRFSGSGSGTDFTLTISSLQPEDFATYYCAQGLRHPKTFGQ
GTKVEIKW

DOM7h-14-65.
(SEQ ID NO: 128)
DIQMTQSPSSLSASVGDRVTITCRASQWIGSQLSWYQQKPGKAPKLLIMW
RSALQSGVPSRFSGSGSGTDFTLTISSLQPEDFATYYCAQGLRHPKTFGQ
GTKVEIKW

DOM7h-14-74.
(SEQ ID NO: 129)
DIQMTQSPSSLSASVGDRVTITCRASQWIGSQLSWYQQKPGKAPKLLIMW
RSSLQSGVPSRFSGSGSGTDFTLTISSLQPEDFATYYCAQGLRHPKTYGK
GTKVENKW

DOM7h-14-76.
(SEQ ID NO: 130)
DIQMTQSPSSLSASVGDRVTITCRASQWIGSQLSWYQQKPGKAPKLLIMW
RSSLQSGVPSRFSGSGSGTDFTLTISSLQPEDFATYYCAQGLKHPKTYGQ
GTKVEIKW

DOM7h-14-82.
(SEQ ID NO: 131)
DIQMTQSPSSLSASVGDRVTITCRASQWIGSQLSWYQQKPGKAPKLLIMW
RSSLQSGVPSRFSGSGSGTDFTLTISSLQPEDFATYYCAQGMRHPKTFGQ
GTKVEIKW

DOM7h-14-100.
(SEQ ID NO: 132)
DIQMTQSPSSLSASVGDRVTITCRASQWIGSQLSWYQQKPGKAPKLLIMW
RSSLQSGVPSRFSGSGSGTDFTLTISSLQPEDFATYYCAQGLRHPKTYGQ
GTKVENKW

DOM7h-14-101.
(SEQ ID NO: 133)
DIQMTQSPSSLSASVGDRVTITCRASQWIGSQLSWYQQKPGKAPKLLIMW
RSALQNGVPSRFSGSGSGTDFTLTISSLQPEDFATYYCAQGLRHPKTFGQ
GTKVEIKW

DOM7h-14-109.
(SEQ ID NO: 134)
DIQMTQSPSSLFASVGDRVTITCRASQWIGSQLSWYQQKPGKAPKLLIMW
RSSLQSGVPSRFSGSGSGTDFTLTISSLQPEDFATYYCAQGLRKPKTFGQ
GTKVKIKW

DOM7h-14-115.
(SEQ ID NO: 135)
DIQMTQSPSSLSASVGDRVTITCRASQWIGSQLSWYQQKPGKAPKLLIMW
RSALQSGVPSRFSGSGSGTDFTLTISSLQPEDFATYYCAQGLRHPKTYGQ
GTKVEIKW

DOM7h-14-116.
(SEQ ID NO: 136)
DIQMTQSPSSLSASVGDRVTITCRASQWIGSQLSWYQQKPGKAPKLLIMW
RSALQSGVPSRFSGSGSGTDFTLTISSLQPEDFATYYCAQGLRYPKTFGQ
GTKVEIKW

DOM7h-14-119.
(SEQ ID NO: 137)
DIQMTQSPSSLSASVGDRVTITCRASQWIGSQLSWYQQKPGKAPKLLIMW
RSSLQSGVPSRFSGSGSGTDFTLTISSLQPEDFATYYCAQGLRHPKTYGQ
GTKVEIKR

DOM7h-14-120.
(SEQ ID NO: 138)
DIQMTQSPSSLSASVGDRVTITCRASQWIGSQLSWYQQKPGKAPKLLIMW
RSSLQSGVPSRFSGSGSGTDFTLTISSLQPEDFATYYCAQGLRHPKTYGQ
GTKVENKR

DOM7h-14-121.
(SEQ ID NO: 139)
DIQMTQSPSSLSASVGDRVTITCRASQWIGSQLSWYQQKPGKAPKLLIMW
RSALQSGVPSRFSGSGSGTDFTLTISSLQPEDFATYYCAQGLRHPKTFGQ
GTKVEIKR

DOM7h-14-122.
(SEQ ID NO: 140)
DIQMTQSPSSLSASVGDRVTITCRASQWIGSQLSWYQQKPGKAPKLLIMW
RSSLQSGVPSRFSGSGSGTDFTLTISSLQPEDFATYYCAQGLRHPKTYGK
GTKVEIKR

DOM7h-14-123.
(SEQ ID NO: 141)
DIQMTQSPSSLSASVGDRVTITCRASQWIGSQLSWYQQKPGKAPKLLIMW
RSSLQSGVPSRFSGSGSGTDFTLTISSLQPEDFATYYCAQGLRHPKTYGK
GTKVENKR

DOM7h-14-56.
(SEQ ID NO: 142)
GACATCCAGATGACCCAGTCTCCATCCTCCCTGTCTGCATCTGTAGGAGA
CCGTGTCACCATCACTTGCCGGGCAAGTCAGTGGATTGGGTCTCAGTTAT
CTTGGTACCAGCAGAAACCAGGGAAAGCCCCTATGCTCCTGATCATGTGG
AGTTCCTCGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCTCAGGGTTTGAGGCATCCTAAGACGTTCGGCCAA
GGGACCAAGGTGGAAATCAAATGG

DOM7h-14-65.
(SEQ ID NO: 143)
GACATCCAGATGACCCAGTCTCCATCCTCCCTGTCTGCATCTGTAGGAGA
CCGTGTCACCATCACTTGCCGGGCAAGTCAGTGGATTGGGTCTCAGTTAT
CTTGGTACCAGCAGAAACCAGGGAAAGCCCCTAAGCTCCTGATCATGTGG
CGTTCCGCGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCTCAGGGTTTGAGGCATCCTAAGACGTTCGGCCAA
GGGACCAAGGTGGAAATCAAATGG

DOM7h-14-74.
(SEQ ID NO: 144)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGCATCCTAAGACGTACGGCAAA

GGGACCAAGGTGGAAAACAAATGG

DOM7h-14-76.
(SEQ ID NO: 145)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAAGCATCCTAAGACGTACGGCCAA

GGGACCAAGGTGGAAATCAAATGG

DOM7h-14-82.
(SEQ ID NO: 146)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTATGAGGCATCCTAAGACGTTCGGCCAA

GGGACCAAGGTGGAAATCAAATGG

DOM7h-14-100.
(SEQ ID NO: 147)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGCGGCATCCTAAGACGTACGGCCAA

GGGACCAAGGTGGAAAACAAATGG

DOM7h-14-101.
(SEQ ID NO: 148)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCGCGTTACAAAATGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGCATCCTAAGACGTTCGGCCAA

GGGACCAAGGTGGAAATCAAATGG

DOM7h-14-109.
(SEQ ID NO: 149)
GACATCCAGATGACCCAGTCTCCATCCTCCCTGTTTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGAAACCTAAGACTTTCGGCCAA

GGGACCAAGGTGAAATCAAATGG

DOM7h-14-115.
(SEQ ID NO: 150)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCGCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGCATCCTAAAACGTACGGCCAA

GGGACCAAGGTGGAAATCAAATGG

DOM7h-14-116.
(SEQ ID NO: 151)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCGCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGTATCCTAAGACGTTCGGCCAA

GGGACCAAGGTGGAAATCAAATGG

DOM7h-14-119.
(SEQ ID NO: 152)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGCGGCATCCTAAGACGTACGGCCAA

GGGACCAAGGTGGAAATCAAACGG

DOM7h-14-120.
(SEQ ID NO: 153)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGCGGCATCCTAAGACGTACGGCCAA

GGGACCAAGGTGGAAAACAAACGG

DOM7h-14-121.

(SEQ ID NO: 154)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCGCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGCATCCTAAGACGTTCGGCCAA

GGGACCAAGGTGGAAATCAAACGG

DOM7h-14-122.

(SEQ ID NO: 155)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGCATCCTAAGACGTACGGCAAA

GGGACCAAGGTGGAAATCAAACGG

DOM7h-14-123.

(SEQ ID NO: 156)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGCATCCTAAGACGTACGGCAAA

GGGACCAAGGTGGAAAACAAACGG

---

The invention claimed is:

1. An anti-serum albumin (SA) immunoglobulin single variable domain variant of DOM7h-11-15 (SEQ ID NO: 1), wherein the variant comprises an amino acid substitution in at least one position selected from the group consisting of:
Met32, Leu49, Ala50, and Phe51,
wherein position Met32 is changed to Leu, Phe, or Ile,
position Leu49 is changed to Ile, Val, or Met,
position Ala50 is changed to Val, Leu, or Ile, and/or
position Phe51 is changed to Leu, Val, Ile, Ala, or Tyr.

2. The anti-serum albumin (SA) immunoglobulin single variable domain variant as claimed in claim 1, wherein
position Met32 is changed to Leu,
position Leu49 is changed to Ile,
position Ala50 is changed to Val, and/or
position Phe51 is changed to Leu.

3. The variant as claimed in claim 1, comprising a binding site that specifically binds human SA with a dissociation constant (KD) of from about 0.1 to about 10000 nM as determined by surface plasmon resonance.

4. The variant as claimed in claim 1, comprising a binding site that specifically binds human SA with an off-rate constant ($K_d$) of from about $1.5 \times 10^{-4}$ to about $0.1\ sec^{-1}$ as determined by surface plasmon resonance.

5. The variant as claimed in claim 1, comprising a binding site that specifically binds human SA with an on-rate constant ($K_a$) of from about $2 \times 10^6$ to about $1 \times 10^4 M^{-1}\ sec^{-1}$ as determined by surface plasmon resonance.

6. The variant as claimed in claim 1, comprising a binding site that specifically binds Cynomolgus monkey SA with a dissociation constant (KD) of from about 0.1 to about 10000 nM as determined by surface plasmon resonance.

7. The variant as claimed in claim 1, comprising a binding site that specifically binds Cynomolgus monkey SA with an off-rate constant ($K_d$) of from about $1.5 \times 10^{-4}$ to about $0.1\ sec^{-1}$ as determined by surface plasmon resonance.

8. The variant as claimed in claim 1, comprising a binding site that specifically binds Cynomolgus monkey SA with an on-rate constant ($K_a$) of from about $2 \times 10^6$ to about $1 \times 10^4 M^{-1}\ sec^{-1}$ as determined by surface plasmon resonance.

9. A multispecific ligand comprising the anti-SA variant as claimed in claim 1, and a binding moiety that specifically binds a target antigen other than SA.

10. A composition comprising the variant as claimed in claim 1, and a pharmaceutically acceptable diluent, carrier, excipient or vehicle.

11. A multispecific ligand comprising the anti-SA variant as claimed in claim 1, and a binding moiety that specifically binds a target antigen other than SA, wherein the target antigen is selected from the group consisting of: IFNα2b and exendin-4.

12. The variant as claimed in claim 3, wherein the dissociation constant (KD) is from about 1 to about 6000 nM, as determined by surface plasmon resonance.

13. The variant as claimed in claim 4, wherein the off-rate constant ($K_d$) is from about $3 \times 10^{-4}$ to about $0.1\ sec^{-1}$ as determined by surface plasmon resonance.

14. The variant as claimed in claim 5, wherein the on-rate constant ($K_a$) is from about $1 \times 10^6$ to about $2 \times 10^4 M^{-1}\ sec^{-1}$ as determined by surface plasmon resonance.

15. The variant as claimed in claim 6, wherein the dissociation constant (KD) is from about 1 to about 6000 nM, as determined by surface plasmon resonance.

16. The variant as claimed in claim 7, wherein the off-rate constant ($K_d$) is from about $3 \times 10^{-4}$ to about $0.1\ sec^{-1}$ as determined by surface plasmon resonance.

17. The variant as claimed in claim 9, wherein the on-rate constant ($K_a$) is from about $1 \times 10^6$ to about $5 \times 10^3 M^{-1}\ sec^{-1}$ as determined by surface plasmon resonance.

* * * * *